(12) United States Patent
Hickman et al.

(10) Patent No.: US 11,554,373 B2
(45) Date of Patent: Jan. 17, 2023

(54) PUMPLESS MICROFLUIDIC ORGAN-ON-A-CHIP SYSTEM INCLUDING A FUNCTIONAL IMMUNE SYSTEM

(71) Applicants: UNIVERSITY OF CENTRAL FLORIDA RESEARCH FOUNDATION, INC., Orlando, FL (US); HESPEROS, INC., Orlando, FL (US)

(72) Inventors: James Hickman, Orlando, FL (US); Alisha Colon, Orlando, FL (US); Christopher McAleer, Orlando, FL (US); Trevor Sasserath, Orlando, FL (US); John Rumsey, Orlando, FL (US); Daniel Elbrecht, Orlando, FL (US)

(73) Assignees: University of Central Florida Research Foundation, Inc., Orlando, FL (US); Hesperos, Inc., Orlando, FL (US)

( * ) Notice: Subject to any disclaimer, the term of this patent is extended or adjusted under 35 U.S.C. 154(b) by 627 days.

(21) Appl. No.: 16/474,768

(22) PCT Filed: Dec. 29, 2017

(86) PCT No.: PCT/US2017/068952
§ 371 (c)(1),
(2) Date: Jun. 28, 2019

(87) PCT Pub. No.: WO2018/126131
PCT Pub. Date: Jul. 5, 2018

(65) Prior Publication Data
US 2020/0001297 A1    Jan. 2, 2020

Related U.S. Application Data

(60) Provisional application No. 62/440,968, filed on Dec. 30, 2016.

(51) Int. Cl.
*B01L 3/00* (2006.01)
*C12M 1/32* (2006.01)
(Continued)

(52) U.S. Cl.
CPC ....... *B01L 3/502753* (2013.01); *C12M 23/12* (2013.01); *C12M 23/16* (2013.01);
(Continued)

(58) Field of Classification Search
None
See application file for complete search history.

(56) References Cited

U.S. PATENT DOCUMENTS

| 8,748,180 B2 | 6/2014 | Shuler et al. |
| 8,815,584 B1 | 8/2014 | Hickman et al. |

(Continued)

FOREIGN PATENT DOCUMENTS

WO    2016100227 A1    6/2016

OTHER PUBLICATIONS

Agarwal, Ashutosh, et al. Microfluidic heart on a chip for higher throughput pharmacological studies. Lab on a Chip 13.18 (2013): 3599-3608.
(Continued)

*Primary Examiner* — William H. Beisner
(74) *Attorney, Agent, or Firm* — Meunier Carlin & Curfman LLC

(57) ABSTRACT

A pumpless microfluidic system is disclosed that can be used to mimic the interaction of organ systems with the immune system. Also disclosed is a method for mimicking an immune system, comprising culturing a plurality of organ cells and at least one population of immune cells in the disclosed pumpless microfluidic system under physiological conditions. The method can further comprise activating an immune reaction in the pumpless microfluidic system, con-
(Continued)

tinuing the culture for a defined period, collecting a sample of culture medium from the system, and assaying the sample for one or more indicators of an immune response.

18 Claims, 46 Drawing Sheets

(51) Int. Cl.
  *C12M 3/06* (2006.01)
  *G01N 33/50* (2006.01)
  *G01N 33/68* (2006.01)
(52) U.S. Cl.
  CPC ..... *G01N 33/5005* (2013.01); *G01N 33/6863* (2013.01); *B01L 2300/0627* (2013.01); *B01L 2300/0877* (2013.01)

(56) References Cited

U.S. PATENT DOCUMENTS

| | | |
|---|---|---|
| 8,828,721 B1 | 9/2014 | Hickman et al. |
| 8,835,168 B2 | 9/2014 | Hickman et al. |
| 9,163,216 B1 | 10/2015 | Hickman et al. |
| 9,404,140 B1 | 8/2016 | Molnar et al. |
| 9,489,474 B2 | 11/2016 | Hickman et al. |
| 9,952,204 B2 | 4/2018 | Hickman et al. |
| 2012/0135452 A1* | 5/2012 | Shuler .................... C12M 29/00 435/395 |
| 2015/0219622 A1 | 8/2015 | Hickman et al. |
| 2015/0369791 A1 | 12/2015 | Hickman et al. |
| 2016/0313306 A1* | 10/2016 | Ingber .................... C12M 23/16 |
| 2018/0355298 A1* | 12/2018 | Loskill ................... C12M 29/00 |

OTHER PUBLICATIONS

Bellas E, et al. In vitro 3D full-thickness skin-equivalent tissue model using silk and collagen biomaterials. Macromolecular bioscience 12, 1627-1636 (2012).
Bers D M. Cardiac excitation-contraction coupling. Nature 2002; 415(6868): 198-205.
Carlsson L. In vitro and in vivo models for testing arrhythmogenesis in drugs. Journal of Internal Medicine 2006; 259(1): 70-80.
Dakhel Y, et al. Erythomycin potentiates pr interval prolonging effect of verapamil in the rat: A pharmacodynamic drug interaction. Toxicol Appl Phamacol 2006; 214:24-29.
Das M, et al. A defined long-term in vitro tissue engineered model of neuromuscular junctions. Biomaterials 2010; 31: 4880-4888.
Das M, et al. Differentiation of skeletal muscle and integration of myotubes with silicon microstructures using serum-free medium and a synthetic silane substrate. Nature Protocols 2007; 2(7): 1795-1801.
Das M, et al. Embryonic motor neuron-skeletal muscle co-culture in a defined system. Neuroscience 2007; 146: 481-488.
Das M, et al. Long-term culture of embyonic rat cardiomyocytes on an organosilane surface in a serum free medium. Biomaterials 2004; 25(25): 5643-5647.
Das M, et al. Skeletal muscle tissue engineering: A maturation model promoting long-term survival of myotubes, structural development of the excitationcontraction coupling apparatus and neonatal myosin heavy chain expression. Biomaterials 30, 5392-5402 (2009).
Das M, et al. Temporal neurotransmitter conditioning restores the functional activity of adult spinal cord neurons in long-term culture. Experimental Neurology 2008; 209: 171-180.
Das, M. et al. A defined system to allow skeletal muscle differentiation and subsequent integration with silicon microstructures. Biomaterials 27, 4374-4380 (2006).
Das M, et al. Electrophysiological and morphological characterization of rat embryonic motoneurons in a defined system. Biotechnology progress 19, 1756-1761, (2003).

Davis, H. et al. Rat Cortical Oligodendrocyte-Embryonic Motoneuron Co-Culture: An Axon-Oligodendrocyte Interaction Model. Journal biomaterials tissue engin 2, 206-214 (2012).
Dhir V, et al. Patterning of diverse mammalian cell types in serum free medium with photoablation. Biotechnol Prog 2009; 25(2): 594-603.
Edwards D, et al. Addition of glutamate to serum-free culture promotes recovery of electrical activity in adult hippocampal neurons in vitro. J Neuroscience meth 190, 155-163 (2010).
Guo X F, et al. Characterization of a human fetal spinal cord stem cell line nsi-566rsc and its induction to functional motoneurons. Tissue Engineering and Regenerative Medicine 2010; 4: 181-193.
Guo X F, et al. Nmj formation between human stem cell derived motoneurons and Yat skeletal muscle in a defined system. Tissue Engineering: Part C 2010; 16(6):1347-1355.
Guo X, et al. Neuromuscular junction formation between human stem cell-derived motoneurons and human skeletal muscle in a defined system. Biomaterials 32, 9602-9611 (2011).
Guo X, et al. Derivation of sensory neurons and neural crest stem cells from human neural progenitor hNP1. Biomaterials 34, 4418-4427 (2013).
Hughes B. 2007 fda drug approvals: A year of flux specialty products dominate innovative drug approvals—a trend that looks set to continue. Nature Reviews Drug Discovery 2008; 7: 107-109.
Huh, D et al. Reconstituting organ-level lung functions on a chip. Science 328, 1662-1668 (2010).
Jung D R, et al. Cell-based sensor microelectrode array characterized by imaging x-ray photoelectron spectroscopy, scanning electron microscopy, impedance measurements, and extracellular recordings. J VacSciTechnol A 1998; 16(3): 1183-1188.
Kang J H, et al. In vitro 3D model for human vascularized adipose tissue. Tissue Eng Part A 15, 2227-2236 (2009).
Kim C, et al. Non-cardiomyocytes influence the electrophysiological maturation of human embryonic stem cell-derived cardiomyocytes during differentiation. Stem cells and development 2010; 19(6): 783-795.
Kita-Matsuo H, et al. Lentiviral vectors and protocols for creation of stable hesc Tines for fluorescent tracking and drug resistance selection of cardiomyocytes. PLoS ONE 2009; 4(4): e5046.
Lawrence C L, et al. Nonclinical proarrhythmia models: Predicting torsades de pointes. Journal of Pharmacological and Toxicological Methods 2005; 52(1): 46-59.
Lipsett M A, et al. Acinar plasticity: development of a novel in vitro model to study human acinar-to-duct-to-islet differentiation. Pancreas 34, 452-457 (2007).
Liu W P, et al. Enantioselectivity in environmental safety of current chiral insecticides. Proc Natl Acad Sci USA 2005; 102(3): 701-706.
Lund A E, et al. Dose-dependent interaction of the pyrethroid isomers with sodium-channels of squid axon-membranes. Neuro toxicology 1982; 3(1): 11-24.
Maduell F. Hemodiafiltration. Hemodial Int 2005; 9(1): 47-55.
Mahler G J, et al. Characterization of a gastrointestinal tract microscale cell culture analog used to predict drug toxicity. Biotechnol Bioeng 2009; 104(1): 193-205.
Mahler G J, et al. Characterization of caco-2 and ht29-mtx co-cultures in an in vitro digestion/cell culture model used to predict iron bioavailability. J Nutr Biochem 2009; 20(7): 494-502.
Marona H R N, et al. Determination of sparfloxcin and its degradation products by hplc-pda. J Antimicrob Chemother 1999; 44: 301-302.
McAleer CW, et al. Functional myotube formation from adult rat satellite cells in a defined serum-free system. Biotechnol Prog. 2015; 31(4):997-1003.
McAleer CW, et al. Mechanistic investigation of adult myotube response to exercise and drug treatment in vitro using a multiplexed functional assay system. J Appl Physiol (1985). 2014; 117(11):1398-405.
McAuliffe G J, et al. Development of a gastrointestinal tract microscale cell culture analog to predict drug transport. Mol Cell Bioengr 2008; 5(2): 119-132.
Meyer T, et al. Qt-screen: High-throughput cardiac safety pharmacology by extracellular electrophysiology on primary cardiac myocytes. Assay and Drug Development Technologies 2004; 2(5): 507-514.

(56) References Cited

OTHER PUBLICATIONS

Mohan D K, et al. Toxin detection based on action potential shape analysis using a realistic mathematical model of differentiated ng108-15 cells. Biosens Bioelectron 2006; 21: 1804-1811.

Molnar P, et al. Photolithographic patterning of c2c12 myotubes using vitronectin as growth substrate in serum-free medium. Biotechnol Prog 2007; 23(1): 265-268.

Molnar P, et al. Synaptic connectivity in engineered neuronal networks, in Patch-clamp methods and protocols, Molnar P and Hickman J J, Editors. 2007, Humana Press: New York. 9 pages.

Mufti N A, et al. Different in vitro systems affect cyp1a1 activity in response to 2,3,7,8-tetrachlorodibenzo-p-dioxin. Toxicol in vitro 1998; 12: 259-272.

Nakamura Y, et al. The in vitro metabolism of a pyrethroid insecticide, permethrin, and its hydrolysis products in rats. Toxicol Appl Pharmacol 2007; 235: 176-184.

Natarajan A, et al. Engineered In Vitro Feed-Forward Networks. J Biotechnol Biomater 3, 2:1 (2013).

Natarajan A, et al. Multielectrode recordings of cardiac action potentials as a high throughput method to evaluate pesticide toxicity. Toxicol In Vitro 2006; 20(3):375-381.

Natarajan A, et al. Patterned cardiomyocytes on microelectrode arrays as a functional, high information content drug screening platform. Biomaterials 2011, 32(18), 4267-4274.

Oh T-i, et al. Real-time fluorescence detection of multiple microscale cell culture analog devices in situ. Cytometry Part A 2007; 71A: 857-865.

Oleaga C, et al. Multi-Organ toxicity demonstration in a functional human in vitro system composed of four organs. Sci Rep. 2016; 6:20030.

Pirozzi KL, et al. Correlation of embryonic skeletal muscle myotube physical characteristics with contractile force generation on an atomic force microscope-based bio-microelectromechanical systems device. Appl Phys Lett. 2013; 103(8):83108.

Pointer C, P et al. Ht29-mtx and caco-21tc7 monolayers as predictive models for human intestinal absorption: Role of mucus layer. J Pharm Sci 2001; 90: 1608-1619.

Rumsey J W, et al. Node of ranvier formation on motoneurons in vitro. Biomaterials 2009; 30: 3567-3572.

Rumsey J W, et al. Tissue engineering the mechanosensory circuit of the stretch reflex arc: Sensory neuron innervation of intrafusal muscle fibers. Biomaterials 31, 8218-8227 (2010).

Schaffner A E, et al. Investigation of the factors necessary for growth of hippocampal neurons in a defined system. J Neurosci Methods 1995; 62(1-2): 111-9.

Scollon E J, et al. In vitro metabolism of pyrethroid pesticides by rat and human hepatic microsomes and cytochrome p450 isoforms. Drug Metabolism and Disposition 2009; 37(1): 221-228.

Selivanova O M, et al. Compact globular structure of thermos thermophilus ribosomal protein s1 in solution. J Biol Chem 2003; 278(38): 36311-36314.

Sin A, et al. The design and fabrication of three-chamber microscale cell culture analog devices with integrated dissolved oxygen sensors. Biotechnol Prog 2004; 20:338-345.

Smith AS, et al. A multiplexed chip-based assay system for investigating the functional development of human skeletal myotubes in vitro. J Biotechnol. 2014;185:15-8.

Smith AS, et al. Utilization of microscale silicon cantilevers to assess cellular contractile function in vitro. J Vis Exp. 2014; (92):e51866.

Stancescu M, et al. A phenotypic in vitro model for the main determinants of human whole heart function. Biomaterials. 2015; 60:20-30.

Subramanian, B. et al. Tissue-engineered three-dimensional in vitro models for normal and diseased kidney. Tissue Eng Part A 16, 2821-2831 (2010).

Sung J H, et al. A micro cell culture analog with 3-d hydrogel culture of multiple cell lines to assess metabolism-dependent cytotoxicity of anti-cancer drugs. Lab Chip 2009; 9(10): 1385-1394.

Sung J H, et al. A microfluidic device for a pharmacokinetic-pharmacodynamic (pk-pd) model on a chip. Lab Chip 2010; 10: 446-455.

Sung J H, et al. Fluorescence optical detection in situ for real time monitoring of enzymatic activity of liver cells in multiple microfludic devices. Biotechnol Bioeng 2009; 104: 516-525.

Sung J H, et al. Prevention of air bubble formation in a microfluidic perfusion cell culture system using a microscale bubble trap. Biomed Microdevices 2009; 11:731-738.

Sung J H, et al. Microfabricated mammalian organ systems and their integration into models of whole animals and humans. Lab on a chip 13, 1201-1212 (2013).

Suter W. Predictive value of in vitro safety studies. Current Opinion in Chemical Biology 2006; 10(4): 362-366.

Sutton N M, et al. Clinical effects and outcome of feline permethrin spot-on poisonings reported to the veterinary poisons information service (vpis), london. J Feline Med & Surgery 2007; 9: 335-339.

Swynghedauw B. Molecular mechanisms of myocardial remodeling. Physiol Rev 1999; 79(1): 215-262.

Takagishi Y, et al. Species-specific difference in distribution of voltage-gated 1-type ca2+ channels of cardiac myocytes. Am J Physiol Cell Physiol 2000; 279(6):C1963-1969.

Tatosian D A, et al. A novel system for evaluation of drug mixtures for potential efficacy in treating multidrug resistant cancers. Biotechnol Bioeng 2009; 103(1):187-198.

Van der Valk J, et al. Optimization of chemically defined cell culture media—replacing fetal bovine serum in mammalian in vitro methods. Toxicology in vitro: an international journal published in association with BIBRA 24, 1053-1063 (2010).

Varghese K, et al. A new target for amyloid beta toxicity validated by standard and high-throughput electrophysiology. PLoS One 2010; 5(1): e8643.

Varghese K, et al. Regeneration and characterization of adult mouse hippocampal neurons in a defined in vitro system. J Neurosci Methods 2009; 177: 51-59.

Viravaidya K, et al. Incorporation of 3t3-l1 cells to mimic bioaccumulation in a microscale cell culture analog device for toxicity studies. Biotechnol Prog 2004; 20:590-597.

Wagner I, et al. A dynamic multi-organ-chip for long-term cultivation and substance testing proven by 3D human liver and skin tissue co-culture. Lab on a chip (2013), 3538.

Wilson K, et al. Direct patterning of coplanar polyethylene glycol alkylsilane monolayers by deep-ultraviolet photolithography as a general method for high fidelity, long-term cell patterning and culture. JUST B 2011, 021020.

Wilson K, et al. Integration of functional myotubes with a bio-mems device for non-invasive interrogation. Lab Chip 2007; 7: 920-922.

Wilson K, et al. Measurement of contractile stress generated by cultured muscle on silicon cantilevers. PLoS One 2010; 5(6): e11042.

Xu H, et al. Development of a stable dual cell-line gfp expression system to study estrogenic endocrine disruptors. Biotechnol Bioeng 2008; 101(6): 1276-1287.

Zimmermann W H, et al. Tissue engineering of a differentiated cardiac muscle construct. Circulation Research 2002; 90(2): 223-230.

International Preliminary Report on Patentability issued for Application No. PCT/US2017/068952, dated Jul. 11, 2019.

International Search Report and Written Opinion issued in PCT/US2017/068952 dated Feb. 26, 2018 (8 pages).

Supplementary European Search Report dated Jul. 20, 2020 for EP Application No. 17885858.

\* cited by examiner

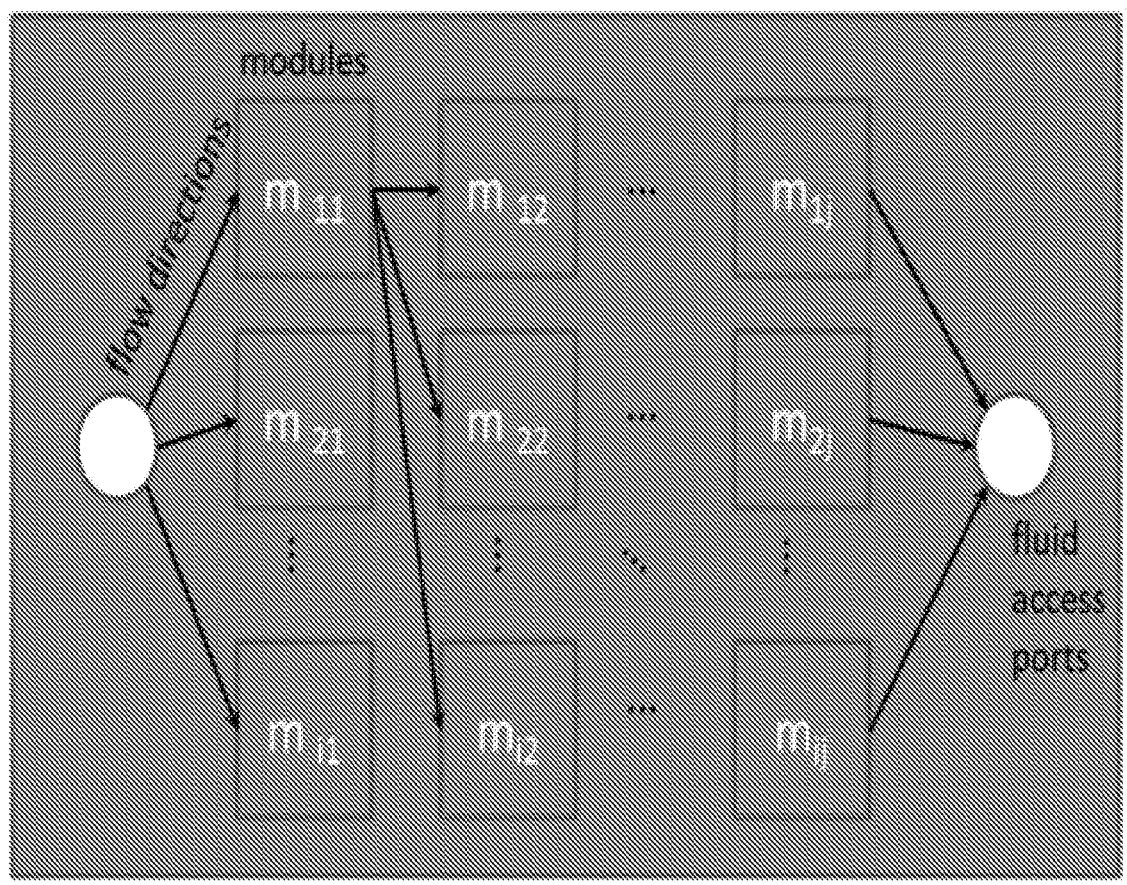
FIG. 1A
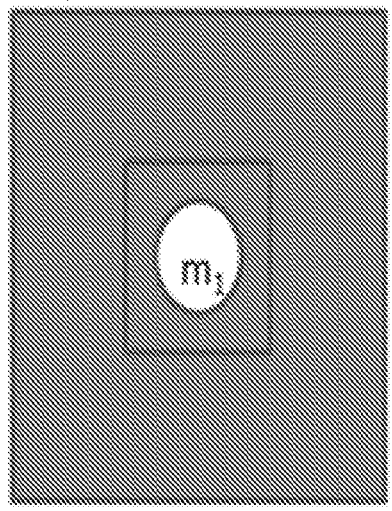 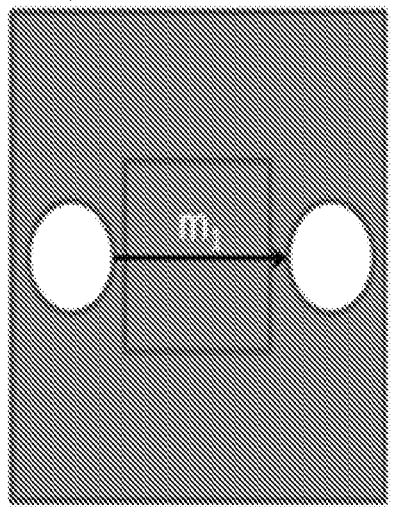
FIG. 1B     FIG. 1C

PUMPLESS MICROFLUIDIC ORGAN-ON-A-CHIP SYSTEM INCLUDING A FUNCTIONAL IMMUNE SYSTEM

CROSS-REFERENCE TO RELATED APPLICATIONS

This application is a national stage application filed under 35 U.S.C. 0371 of PCT/US2017/068952 filed Dec. 29, 2017, which claims the benefit of U.S. Provisional Patent Application No. 62/440,968, filed on Dec. 30, 2016, entitled "PUMPLESS MICROFLUIDIC ORGAN-ON-A-CHIP SYSTEM INCLUDING A FUNCTIONAL IMMUNE SYSTEM," the disclosures of which are expressly incorporated herein by reference in their entireties.

BACKGROUND

The major research uses of animals are both in assessing potential toxicity of chemicals and in drug testing. Animal tests often are long in duration, expensive, and raise ethical issues. Further, animal tests are not always predictive of human response. This fact is easily demonstrated in drug development where only 11% of chemicals exiting animal trials are successful in humans. In terms of human response to environmental toxicants, it is not ethically possible to conduct direct tests on humans, and extrapolation of animal results to human response is problematic. Over-regulation results in unnecessary expense; under-regulation endangers human health and the environment, so better testing systems are necessary.

In vitro tests can supplement and may reduce dependency on animal tests. However, current in vitro tests fail to capture many important aspects of human and mammalian response to chemicals. Most in vitro tests are based on the use of multi-well plates where isolated cells or tissues are placed in medium spiked with a bolus dose of the test chemical. Such systems miss key aspects of physiological response. For example, the dose dynamics in the body differ considerably from static systems as time-dependent changes in chemical concentration occur in the body at a tissue site due to the processes controlling absorption, distribution, metabolism and excretion of a compound. Further, static well systems typically use a single cell or tissue type; in the body, metabolites are exchanged between different tissue/organ compartments. Even if multiple tissue types were represented in a single well, the ratio of one tissue to another and the nature of the circuits connecting them can alter the time-dependent concentration of the metabolites. In addition to these factors, single cells in a well, in most cases, do not represent functional tissues or subsystems of the body, nor experience the mechanical forces the cells in the body do, particularly those associated with fluid flow, and these mechanical forces are known to alter gene expression and metabolism of many chemicals.

Immune responses to treatments in vivo can range from mild inflammation to extreme cytokine storm induction to immunosuppression. These responses are not easily predicted by outcomes of in vitro testing. Thus, the immune system presents an additional confounding variable that obscures data obtained during in vitro testing.

SUMMARY

A pumpless microfluidic system is disclosed that can be used to mimic the interaction of organ systems with the immune system. The system comprises a first chamber containing a first plurality of organ cells attached to at least a portion of a cell attachment surface of the first chamber, wherein the first plurality of organ cells mimic a function of a first organ; and at least one population of immune cells, including at least one population of leukocytes, circulating through the first chamber in a serum free culture medium under conditions suitable for survival of the at least one population of leukocytes for at least 2, 3, 4, 5, 6, 7, or more days without activation. Immune cell activation can be detected using routine methods. For example, when an immune cell is activated, it expresses a subset of surface receptors that are upregulated/expressed during an immune response, e.g. CCR5, CD11b, CD69, and CD86.

The immune cells are in some embodiments circulating in the pumpless microfluidic system at a static flow rate. For example, the flow can be about 100 µL/min to 8000 µL/min. In some embodiments, the immune cells are circulating in the pumpless microfluidic system at about 100, 200, 300, 400, 500, 600, 700, 800, 900, 1,000, 2,000, 3,000, 4,000, 5,000, 6,000, 7,000, or 8,000 µL/min.

In some embodiments, flow is set so that about 5% to about 400% of the medium recirculates every minute. In some embodiments, about 5, 6, 7, 8, 9, 10, 11, 12, 13, 14, 15, 16, 17, 18, 19, 20, 25, 30, 35, 40, 45, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, or 400% of the medium recirculates every minute.

In some embodiments, the immune cells are circulating in the pumpless microfluidic system by unidirectional flow. For example, in some cases, the rate of flow is constant for a portion of time, stops while the liquid returns to the injection port, and then is constant again. This kind of flow can have a square wave pattern.

In other embodiments, the immune cells are circulating in the pumpless microfluidic system by bidirectional flow. For example, flow can be constant in one direction and then be constant in the opposite direction, which can also have a square wave pattern. Alternatively, flow can be time-dependent, e.g., having a sinusoidal or sawtooth pattern.

In some embodiments, the pumpless microfluidic system further comprises a second chamber in fluid connection with the first chamber containing a second plurality of organ cells attached to at least a portion of a cell attachment surface of the second chamber, wherein the second plurality of organ cells mimic a function of a second organ.

In some embodiments, the pumpless microfluidic system further comprises a third chamber in fluid connection with the first and second chambers containing a third plurality of organ cells attached to at least a portion of a cell attachment surface of the third chamber, wherein the third plurality of organ cells mimic a function of a third organ.

In some embodiments, the pumpless microfluidic system further comprises additional chambers in fluid connection with the first, second, and third chambers containing additional organ cells that mimic a function of additional organs.

The disclosed system can be used with any combination of organ cells needed to mimic the organ systems of interested. For example, the organ cells of the disclosed pumpless microfluidic system can in some embodiments include cardiomyocytes, skeletal muscle myotubes, hepatocytes, kidney cells, neurons, epithelial cells, astrocytes, Schwann cells, bone marrow cells, cancer cells lines (drug-resistant and non-drug resistant), blood vessel endothelial cells, pancreatic islet cells, oligodendrocytes, synoviocytes, fibroblasts, or any combination thereof.

The pumpless microfluidic system can further comprise a sensor configured to non-invasively measure a function of the cells. As an example, cardiac cells can be monitored for beat frequency, conduction velocity, and/or contractile force. The sensor can therefore be a microcantilever, a microelectrode array (MEA), a light sensor, or any combination thereof. The pumpless microfluidic system can also further comprise a recording device operably connected to the sensor, wherein the recording device is configured to record data from the sensor.

In preferred embodiments, at least one chamber and sensor of the system are arranged on a chip. In particular, the pumpless microfluidic system can comprise an organ-on-a-chip (OC), which, as used herein, is a microfluidic cell culture chip that stimulates the activities, mechanics and physiological response of entire organs and organ systems. Therefore, the pumpless microfluidic system can comprise one or more microfluidic channels interconnecting the plurality of chambers.

Materials for producing the chip include SiO2, glass, and synthetic polymers. Synthetic polymers can, for example, comprise polystyrol (PS), polycarbonate (PC), polyamide (PA), polyimide (PI), polyetheretherketone (PEEK), polyphenylenesulfide (PPSE), epoxide resin (EP), unsaturated polyester (UP), phenol resin (PF), polysiloxane, e.g. polydimethylsiloxane (PDMS), melamine resin (MF), cyanate ester (CA), polytetrafluoroethylene (PTFE) and mixtures thereof. The synthetic polymers are optically transparent and can include, for example, polystyrol (PS), polycarbonate (PC), and polysiloxane, e.g. polydimethylsiloxane (PDMS).

In some embodiment, the at least one population of immune cells comprise peripheral blood mononuclear cells (PBMCs). In some embodiment, the at least one population of immune cells comprises granulocytes, such as neutrophils, eosinophils, basophils, and mast cells. In some embodiment, the at least one population of immune cells comprises agranulocytes, such as monocytes, macrophages, lymphocytes, and natural killer (NK) cells.

The pumpless microfluidic system can also further comprise at least one agonist or antagonist of an innate immune response. The innate immune system, also known as the non-specific immune system or in-born immunity system, is an important subsystem of the overall immune system that recognizes and responds to pathogens in a generic way, but, unlike the adaptive immune system, the system does not confer long-lasting or protective immunity to the host.

For example, the agonist of the innate immune response can comprise a complement protein and/or be an agent that activates a complement cascade. The complement system is a part of the immune system that enhances (complements) the ability of antibodies and phagocytic cells to clear microbes and damaged cells from an organism, promotes inflammation, and attacks the pathogen's plasma membrane. The complement system consists of a number of small proteins found in the blood that are normally circulating as inactive precursors (pro-proteins). Over 30 proteins and protein fragments make up the complement system, including serum proteins, serosal proteins, and cell membrane receptors. They account for about 10% of the globulin fraction of blood serum and can serve as opsonins. When stimulated by one of several triggers, proteases in the system cleave specific complement proteins to release cytokines and initiate an amplifying cascade of further cleavages. Therefore, in some embodiments, the agonist is an activated complement protein. In some embodiments, the agonist promotes cleavage of one or more complement pro-proteins. The complement system includes a classical complement pathway, an alternative complement pathway, and a lectin pathway, and the disclosed system can comprise agonists of one or more of these pathways to activate an innate immune response in the system.

As another example, the agonist of the innate immune response can comprise an interferon. Type I interferons (IFN), secreted mainly by dendritic cells, play the central role in antiviral host defense and creation of an effective antiviral state in a cell. IFN binds to the IFN receptors, inducing expression of hundreds of interferon-stimulated genes. This leads to production of proteins with antiviral properties, such as protein kinase R, which inhibits viral protein synthesis, or the 2',5'-oligoadenylate synthetase family, which degrades viral RNA. These molecules can establish an antiviral state in cells.

For example, innate immunity antagonists could be used to study the effects of viral proteins in a body-on-a-chip system. Specifically, viral proteins VP24, VP35 and VP40 (produced by Ebola virus and Marburg virus) inhibit interferon alpha and beta production and block the activation of the antiviral protein kinase R. As another example, toll-like receptors have been implicated in the pathogenesis of cardiovascular diseases including atherosclerosis, thrombosis, and myocardial remodeling. Therefore, antagonists to TLRs have been proposed as therapeutics to treat cardiovascular disease, which can be tested in the disclosed system.

The pumpless microfluidic system can also further comprise at least one agonist or antagonist of an adaptive immune response. The adaptive immune system, also known as the acquired immune system or, is a subsystem of the overall immune system that is composed of highly specialized, systemic cells and processes that eliminate pathogens or prevent their growth. Adaptive immune responses are elicited by antigens. The cells that carry out the adaptive immune response are white blood cells known as lymphocytes. There are two main broad classes adaptive immune response antibody responses and cell mediated immune response, which are carried by two different lymphocytes (B cells and T cells).

The agonist of the adaptive immune response can therefore comprise antibodies, or a B cells capable of producing antibodies. The agonist of the adaptive immune response can also comprise T cells as discussed above. In addition, activation of T cells by antigens on antigen producing cells results in the release of cytokines. Cytokines are low molecular weight, soluble proteins that are produced in response to an antigen and function as chemical messengers for regulating the innate and adaptive immune systems. They are produced by virtually all cells involved in innate and adaptive immunity, but especially by T helper (Tx) lymphocytes. The activation of cytokine-producing cells triggers them to synthesize and secrete their cytokines. The cytokines, in turn, are then able to bind to specific cytokine receptors on other cells of the immune system and influence their activity in some manner.

As one example, auto-antibodies against pancreatic beta cells can be used to target immune cells to attack the beta cells, thereby mimicking type I diabetes.

In some embodiments, the agonist or antagonist of the adaptive immune response comprises a cytokine. Some cytokines are antagonistic in that one cytokine stimulates a particular defense function while another cytokine inhibits that function. Other cytokines are synergistic wherein two different cytokines have a greater effect in combination than either of the two would by themselves. Cytokines that regulate innate immunity are produced primarily by mononuclear phagocytes such as macrophages and dendritic cell, although they can also be produced by T-lymphocytes, NK cells, endothelial cells, and mucosal epithelial cells. They are produced primarily in response to pathogen-associated molecular patterns (PAMPs) such as LPS, peptidoglycan monomers, teichoic acids, unmethylated cytosine-guanine dinucleotide or CpG sequences in bacterial and viral genomes, and double-stranded viral RNA. Cytokines produced in response to PRRs on cell surfaces, such as the inflammatory cytokines IL-1, IL-6, IL-8, and TNF-alpha, mainly act on leukocytes and the endothelial cells that form blood vessels in order to promote and control early inflammatory responses. Cytokines produced in response to PRRs that recognize viral nucleic acids, such as type I interferons, primarily block viral replication within infected host cells.

Cytokines that regulate adaptive immunity are produced primarily by T-lymphocytes that have recognized an antigen specific for that cell. These cytokines function in the proliferation and differentiation of B-lymphocytes and T-lymphocytes after antigen recognition and in the activation of effector cells.

Example agents that can be used to active the immune cells in the disclosed system include phorbol 12-myristate 13-acetate (PMA), lipopolysaccharide (LPS), interferons (e.g. IFN-γ), interleukins (e.g. IL-β (pro-inflammatory), IL-2 (pro-inflammatory), IL-4 (anti-inflammatory), IL-6 (pro-inflammatory), IL-8 (pro-inflammatory), IL-10 (anti-inflammatory), IL-13 (anti-inflammatory), TNF-α (pro-inflammatory), and any combination thereof.

The disclosed pumpless microfluidic system comprises a serum free medium suitable for the survival of the at least one population of leukocytes in the system for at least two days without activation. In some embodiments, the serum free medium comprises Neurobasal A™ medium, B27 Supplement™, Glutamax™, GDNF, BDNF, CNTF, NT3, NT4, vitronectin, agrin, sonic hedgehog, laminin, cAMP, retinoic acid, IGF-1, and NaCl. For example, the serum-free medium can be prepared by mixing growth factor and hormone supplement compositions of medium 1 in Table 1 and medium 2 in Table 2 in a 1:1 v/v ratio.

Also disclosed is a method for mimicking an immune system, comprising culturing the first plurality of organ cells, the second plurality of organ cells, and the at least one population of immune cells in the disclosed pumpless microfluidic system under physiological conditions. By mimicking an immune system and its interaction with other organ cells, the disclosed system can be used to evaluate organ damage, drug toxicities, drug efficacy, and drug mechanism, just to name a few.

The disclosed method can be used, for example, to study off-target responses of immune drugs and their metabolites. In these embodiments, the system can comprise, for example, immune cells, liver cells, cardiomyocytes, skeletal muscle cells, and neurons.

The disclosed method can be used, for example, to study neuromuscular immune diseases, such as Myasthenia gravis. In these embodiments, the system can comprise, for example, immune cells, liver cells, skeletal muscle cells, neurons, complement proteins, and auto-antibodies.

The disclosed method can be used, for example, to study leukemia. In these embodiments, the system can comprise, for example, immune cells, bone marrow cells lines, liver cells, and cardiac cells (i.e., for off-target effects).

The disclosed method can be used, for example, to study cancer. In these embodiments, the system can comprise, for example, immune cells, cancer cells (e.g., cancer cell line of interest), liver cells, and cardiac cells (i.e., for off-target effects).

The disclosed method can be used, for example, to study vasculitis. In these embodiments, the system can comprise, for example, immune cells, endothelial cells, liver cells, complement proteins, and auto-antibodies.

The disclosed method can be used, for example, to study type I diabetes. In these embodiments, the system can comprise, for example, immune cells, pancreatic islet cells, liver cells, complement proteins, and auto-antibodies.

The disclosed method can be used, for example, to study rheumatoid arthritis. In these embodiments, the system can comprise, for example, immune cells, liver cells, fibroblasts, synoviocytes, complement proteins, and auto-antibodies.

The method can therefore further comprise evaluating the system for an immune response. In some embodiments, the immune response is evaluated by monitoring the first plurality of organ cells, the second plurality of organ cells, or any combination thereof, for immune cell infiltration. For example, immune cell infiltration can be monitored using phase microscopy and immunocytochemistry In some embodiments, the immune response is evaluated by collecting a sample of culture medium from the system, and assaying the sample for one or more biomarkers indicative of an immune response.

In some embodiments, the one or more indicators of an immune response comprise cytokines. Examples of cytokines that are indicators of an immune response include, but are not limited to, CXCL8/IL-8, GM-CSF, IFN-gamma, IL-1 beta/IL-1F2, IL-2, IL-4, IL-5, IL-6, IL-10, IL-12 p70, TNF-alpha, VEGF, GM-CSF, IFN-gamma, IL-1 beta/IL-1F2, IL-2, IL-5, IL-6, IL-7, IL-13, IL-15, IL-17A, IL-17F, IL-22, IL-23, IL-31, IL-33, IL-36 beta, and TNF-alpha.

In some embodiments, the one or more indicators of an immune response comprise kidney biomarkers. Kidney biomarkers that are indicative of an immune response include Clusterin, Cystatin C, CXCL10/IP-10, Osteopontin (OPN), RBP4, TFF3, and TIM-1/KIM-1/HAVCR.

In some embodiments, the one or more indicators of an immune response comprise cardiac biomarkers. Cardiac biomarkers that are indicative of an immune response include CD40 Ligand/TNFSF5, GDF-15, Pappalysin-1/PAPP-A, PCSK9, ST2/IL-33 R, TNF RII/TNFRSF1B, C-Reactive Protein/CRP, Cystatin C, Myeloperoxidase/MPO, P-Selectin/CD62P, Serpin E1/PAI-1, and TIMP-1.

In some cases, the source of organ cells causes the immune reaction. For example, organ cells from a diseased subject can be used. In some cases, the organ cells have genetic defects that cause disease or dysfunction. In some cases, the organ cells are not autologous to mimic organ transplantation.

The disclosed method can also further comprising activating an immune reaction in the pumpless microfluidic system and continuing the culture for a defined period prior to evaluating the system for an immune response. For example, an immune reaction can be activated using agonists of an innate or adaptive immune response as discussed above. In addition, or as an alternative, the immune reaction can be activated by a physical insult to one or more of the plurality of organ cells. The immune reaction can also be activated adding one or more chemical or biological agents to the culture medium. For example, the immune reaction can also be activated adding phorbol 12-myristate 13-acetate (PMA), lipopolysaccharide (LPS), interferons (e.g. IFN-γ), interleukins (e.g. IL-β (pro-inflammatory), IL-2 (pro-inflammatory), IL-4 (anti-inflammatory), IL-6 (pro-inflammatory), IL-8 (pro-inflammatory), IL-10 (anti-inflammatory), IL-13 (anti-inflammatory)), TNF-α (pro-inflammatory), or any combination thereof.

In some embodiments of the disclosed method, at least one of the plurality of organ cells mimics a diseased organ. For example, the disease can be an autoimmune disease selected from the group consisting of myasthenia gravis, rheumatoid arthritis, lupus, multiple sclerosis, type I diabetes, vasculitis, or any combination thereof. In the case of autoimmune diseases, the method can also involve the addition of complement, autoantibodies, or combinations thereof to provide an innate immune response. For example, neuromuscular cells can be treated with antibodies and complement proteins to mimic myasthenia gravis. In some cases, the cells mimic damaged cardiac tissue. For example, cardiac cells can be treated with amiodarone to damage cardiac tissue and mimic myocardial infarction.

The disclosed system and method also provides a unique ability to study combinations of diseases involving an immune response, so the system can comprise any combination of cells, agonists, and insults needed to mimic combinations of diseases, insults, and cross-reactions that might occur in vivo.

In some embodiments, the method further involves measuring a functional readout of tissue damage. For example, in cases where the mimicked tissue is cardiac tissue, the function readout can be selected from the group consisting of beat frequency, conduction velocity, and contractile force. In cases where the mimicked tissue is liver tissue, the function readout can be selected from the group consisting of CYP enzyme activity, urea levels, and albumin levels.

In a particular embodiment, the system comprises at least cardiac cells and immune cells, and the method involves mimicking damage to the cardiac cells, e.g. to mimic heart failure or infarction, monitoring the cardiac cells for immune cell infiltration, measuring cytokine levels, measuring beat frequency, measuring conduction velocity, and measuring contractile forces. Cardiac damage can be mimicked physically or chemically using known or candidate methods.

In another particular embodiment, the system comprises at least liver cells, immune cells, and organ cells that are the target of a candidate drug, and the method involves adding a candidate drug(s) to the system with possible-off target toxicity, monitoring the liver cells for immune cell infiltration, measuring cytokines, measuring CYP enzyme activity, measuring urea, measuring albumin production, or any combination thereof.

In another particular embodiment, the system comprises at least immune cells and at least one plurality of organ cells, and the method involves adding an agent(s) to the system to activate the immune system and induce a pro-inflammatory state in the organ cells, and monitoring the organ cells for immune cell infiltration, measuring cytokine levels, assaying the immune cells for surface marker expression, assaying the organ cells for function, or any combination thereof. For example, obesity is known to cause a pro-inflammatory state, and certain infections, e.g. sepsis, are known to cause a general pro-inflammatory state.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

DESCRIPTION OF DRAWINGS

The components in the drawings are not necessarily to scale relative to each other. Like reference numerals designate corresponding parts throughout the several views.

FIGS. 1A to 1D show example pumpless microfluidic organ-on-a-chip systems for inclusion of a functional immune system. FIG. 1A shows possible flow directions with different modules.

FIG. 1B shows a single module with no flow. FIG. 1C shows a single module with flow. FIG. 1D shows three modules with flow.

FIGS. 3A and 3B show phase contrast images of THP-1 cells at different magnifications. FIG. 3C shows cell viability after 7 days in culture. FIG. 3D shows the number of THP-1 cells circulating after 7 days in culture. FIG. 3E shows immunohistochemical staining of THP-1 cells expressing CD14, CD16, and CD69. FIG. 3F shows flow cytometry of THP-1 cells expressing CD14, CD16, and CD69.

FIG. 4A shows the HPLC determined amiodarone concentration vs. standard curve (left graph) and the amiodarone concentration in 3-O systems+THP-1 cells 24 hours after the addition of the compound. FIG. 4B shows normalized cardiac contractile force up to four days after the addition of amiodarone, in the presence or and absence of THP. FIG. 4C shows the normalized cardiac conduction velocity up to four days after the addition of amiodarone and in the presence or absence of THP. FIG. 4D shows the normalized cardiac beat frequency up to four days after the addition of amiodarone and in the presence or absence of THP. FIG. 4E shows the normalized skeletal muscle force up to four days after the addition of amiodarone, in the presence or absence of THP. FIG. 4F shows immunocytochemistry of liver cells in systems with recirculating THP macrophages and treated with amiodarone. The increase in CD11b and CD86 staining compared to controls indicates infiltration of THP macrophages into the liver tissue module.

FIG. 5A shows cardiac cell metabolic function and viability as measured by an Alamar Blue test. FIG. 5B shows skeletal cell metabolic function and viability as measured by an Alamar Blue test. FIG. 5C shows phase contrast images of THP-1 cell infiltration into a cardiac MEA chip at days 3, 5, and 7. FIG. 5D (left image) shows THP-1 cells loaded with CellTracker Red dye and infiltrating a cardiac MEA at day 3 (phase contrast image shown at right for comparison).

FIG. 6A is a graph of CYP enzyme activity, indicating a reduction in CYP3A4 in systems dosed with amiodarone. FIG. 6B is a graph of urea production throughout the seven-day testing period. FIG. 6C is a graph of albumin production at days 5 and 7, indicating a reduction for systems treated with amiodarone. FIG. 6D is a graph of liver viability at day 7. N=4 systems. Data points are mean±SEM.

FIG. 7A shows selected cytokine expression profiles analyzed throughout the 7-day experimental time course. FIG. 7B shows flow cytometry quantification of THP-1 cells expressing CCR5, CD11b and CD86 pre- and post-direct PMA, or amiodarone treatment.

FIG. 7C shows flow cytometry quantification of THP-1 cells removed from 3-O systems that included the THP-1 cells. The THP-1 cells expressed CCR5, CD11b and CD86 pre- and post-amiodarone treatment. Data points are mean±SEM.

FIG. 8A is a graph showing normalized cardiac force measurements from cantilevers. FIG. 8B is a graph showing normalized cardiac conduction velocity measurements from MEAs. FIG. 8C is a graph showing normalized beat frequency measurements from cantilevers. FIG. 8D is a graph showing normalized skeletal muscle force measurements from cantilevers. N=3 systems. Data points are mean±SEM.

FIG. 9A shows a graph of Cyp activity for 3A4, 2C9, and 1A isoforms normalized to the 3-O control. FIG. 9B shows a graph of urea production by liver cells. FIG. 9C shows a graph of albumin production by liver cells. FIG. 9D shows CD11b staining in liver tissue, indicating THP-1 cell infiltration into systems treated with LPS+ IFNγ.

FIG. 10B shows CCR5, CD11b, and CD86 expression before and after dosing with LPS+ IFNγ.

FIGS. 11A and 11B show phase contrast images of PBMCs. FIG. 11C demonstrates that cell viability in the systems is similar to that found under static conditions on days 1 and 2. FIGS. 11D and 11E show that the PBMCs stain positively for the surface marker CD14. Further analysis of patient PBMCs by flow cytometry (FIG. 11F) indicates populations of cells express the CD14, CD16, and CD69. These data indicate the intrinsic population variability in patient-derived PBMCs, and illustrate the system's ability to evaluate patient-specific treatment programs, as indicated by FIG. 11F.

FIG. 12A shows tilt direction and flow path options may produce two or more separate fows of compositions, such as media, and the flows may have the same or different flow rates or ratios of mixing. FIG. 12B1 (left) and FIG. 12B2 (right) shows particular flow paths. FIG. 12C1 (left) and FIG. 12C2 (right) shows mixing ratios for mixing two compositions.

FIG. 13A shows a stacked embodiment comprising a plurality of components in a three-dimensional relationship with one another. FIG. 13B shows a cell culture analog system comprising a planar relationship of a plurality of components in fluid connection that is formed within a planar rectangular form. FIG. 13C shows a cell culture analog system comprising a planar relationship of a plurality of components in fluid connection. FIG. 13D shows a cell culture analog system comprising a planar relationship of a plurality of components in fluid connection that is formed within a planar rectangular form.

DETAILED DESCRIPTION

Figure 1D:
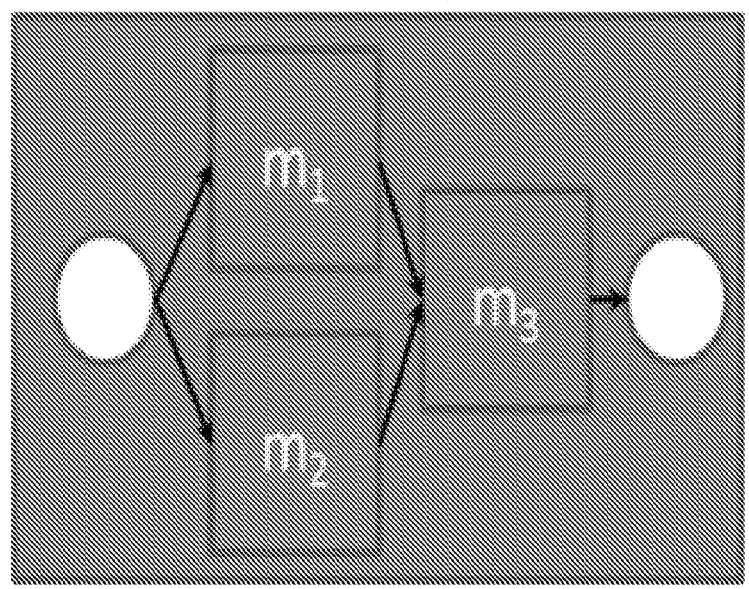

The pharmaceutical industry faces growing challenges in the area of drug discovery. Specifically, extended timeframes combined with low success rates from phase I trials has led to skyrocketing costs. Furthermore, many novel drugs are affected by post-market safety events, indicating a need for more robust efficacy and toxicity data to be generated during the drug discovery process. Paralleling the rising cost of discovery and poor performance of drug development, advances in the biomimetic qualities, and robustness of data readouts in human-on-a-chip systems has led to a growing interest in their use as model systems for drug discovery, including pharmacodynamics and pharmacokinetics with the aspirations of reduced cost and increased efficiency.

One current limitation of in vitro drug discovery platforms is the absence of an immune system component. These systems fail to address the potential immune disrupting effects of novel drug compounds. These effects could range from mild inflammation to extreme cytokine storm induction to immunosuppression. An integrated immune component i facilitates seamless extraction of immune-related data with functional and biomarker data generated by other "chips" of an in vitro system. Collecting immune response data in parallel with functional and biomarker data sets significantly enhances the horizontal scalability of biomimetic human-on-a-chip systems enhancing their application for both broad-based and targeted drug discovery programs.

The immune system is a complex collection of cells and molecules responsible for returning homeostatic balance to the body in response to minor perturbations from physiological stress to combating major dysfunction ranging from tumorigenic cells to circulating pathogens. The immune system coordinates with several other organ systems to orchestrate the activities necessary to combat infection, eliminate damaged cells, and return to basal physiology, thereby maintaining homeostasis. Complicating matters, the immune system responds uniquely to different pathological conditions. Coordination of the insult-specific responses is mediated by a suite of immune system signaling molecules collectively called cytokines, and by direct cell-cell interactions.

One important immune system cell for both cytokine production, and cell-cell interaction is the monocyte/macrophage. Monocytes/macrophages are ubiquitous sentry immune cells involved in a range of immune activities including wound healing, pathogen elimination and activating the adaptive immune response. Moreover, monocytes/macrophages sit at the crossroads of two general immune response paradigms. On one hand, pro-inflammatory stimulation by molecules like TNF-a, LPS, IFN-g leads to a classical activation of macrophages resulting in pathogen and/or tumor cell elimination. At the other end of the spectrum, is an immunoregulating, tissue remodeling phenotype driven largely by damaged tissues and IL-10. In both cases, circulating monocytes are activated by cytokines and other signaling molecules, extravasate from the bloodstream, migrate to sites of infection, or tissue damage and begin the process of pathogen removal or tissue repair.

While primary activation of macrophages in response to cytokines or drug compounds, or secondarily as a result of molecules produced by tissues affected by the circulating compound will result in some similar immune responses, macrophage interaction with target tissues will vary according to the activation program and tissue damaged. For example, classical activation, readying the macrophages to eliminate pathogens, will produce a cytokine profile that enhances the immune system's capabilities for pathogen removal and chemotaxis of leukocytes to sites of infection, whereas an immunoregulating phenotype will produce a different cytokine profile, and chemotaxis of macrophages to sites of tissue damage.

The examples below disclose an immune human-on-a-chip model containing leukocytes capable of responding to indirect activation resulting from cytokines produced by damaged tissue and directly responding signaling molecules. These different approaches to monocyte/macrophage activation lead to distinct responses by the system in terms of cytokine production and cell-cell interactions while also facilitating interrogation of interacting tissues in the recirculating system using functional and biomarker readouts. This system could find broad application in drug discovery for systemic diseases, including cancer and inflammatory disorders where the complex interaction of drugs, immune system and other organ systems is of great importance. Furthermore, the system has targeted applications for improving drug discovery for autoimmune diseases and to enhance studies of autoimmune disease treatment for precision medicine. Moreover, the ability of this human-on-a-chip model to recreate a subset of the diverse and dynamic interactions between immune cells and their organ system counterparts and the responses of those cells to novel drug compounds increases the sophistication of the human-on-a-chip systems and brings patient healthcare one step closer to realizing personalized medicine.

Over time, cell culture medium has evolved from a simple salt solution to preserve tissue to more complex compositions, which can be used to maintain cells and tissues for extended periods of time. Human or animal sera, the most commonly used being fetal bovine serum, can be used to supplement basic media since they contain essential compounds for the growth and maintenance of cells.

To improve the quality, consistency and definition of the culture medium, serum free mediums can be used. Variations in mediums are known to affect cell culture maintenance and subsequent experimental data (Van der Valk et al., 2010). Serum-free media formulations can be based on the addition of cell-specific growth factors and supplements to a common base medium in order to facilitate the correct maintenance of specific cell cultures (Edwards et al., 2010). For example, following the first serum-free defined culture system for hippocampal neurons (Schaffner et al., 1995), a defined serum-free medium has been used with cardiomyocytes (Nataraj an et al., 2011), motoneurons (Das et al., 2003), sensory neurons (Rumsey et al., 2010), and skeletal muscle cells (Das et al., 2006). In an aspect, in vitro cell-cultures can be designed to mimic the relevant in vivo environment. For example, a temperature of 37° C., and a controlled humidified gas mixture of 5% $CO_2$ and 95% $O_2$ can be used as the standard physical conditions. A blood surrogate medium with appropriate micro and macronutrients can be used to recreate the chemical milieu.

With respect to the disclosed systems, an advancement in the formulation of serum-free media was needed. These disclosed systems can maintain different cell types in a single housing; thus, it is a challenge to identify a common, serum-free formulation that can preserve functionality and morphological phenotypes of the different cells in co-culture. The need to maintain in vitro models for extended periods is of great importance for drug development applications. Assessment of chronic compound exposure to various tissues, and understanding the effects of prolonged metabolite or waste build-up in specific organ compartments can be essential for obtaining accurate predictions of in vivo responses to drug treatment.

In some embodiments, the serum-free medium can be prepared by mixing growth factor and hormone supplement compositions of medium 1 (Table 1) and medium 2 (Table 2) in a 1:1 v/v ratio.

TABLE 1

Composition of Medium 1

| Component | Amount | Catalogue # | Source |
|---|---|---|---|
| Neurobasal A ™ (see Table 3) | 500 mL | 10888 | Gibco/Invitrogen |
| Antibiotic-Antimycotic | 5 mL | 15240-062 | Gibco/Invitrogen |
| Glutamax ™ (see Table 5) | 5 mL | 35050-061 | Gibco/Invitrogen |
| B27 Supplement ™ (see Table 4) | 10 mL | 17504-044 | Gibco/Invitrogen |
| G5 Supplement (100X) | 5 mL | 17503-012 | Gibco/Invitrogen |
| rhVEGF165 | 10 µg | P2654 | Gibco/Invitrogen |
| Acidic FGF | 12.5 µg | 13241-013 | Gibco/Invitrogen |
| Heparin Sulphate | 50 µg | D9809 | Sigma-Aldrich |
| LIF | 10 µg | L5158 | Sigma-Aldrich |
| Vitronectin | 50 µg | V0132 | Sigma-Aldrich |
| CNTF | 20 µg | CRC 401 | Cell Sciences |
| NT 3 | 10 µg | CRN 500B | Cell Sciences |
| NT 4 | 10 µg | CRN 501B | Cell Sciences |
| GDNF | 10 µg | CRG 400B | Cell Sciences |
| BDNF | 10 µg | CRB 600B | Cell Sciences |
| CT-1 | 10 µg | CRC 700B | Cell Sciences |

TABLE 2

Composition of Medium 2

| Component | Amount | Catalogue # | Source |
|---|---|---|---|
| Neurobasal A ® (see Table 3) | 500 mL | 10888 | Gibco/Invitrogen |
| Glutamax ™ (see Table 5) | 5 mL | 35050-061 | Gibco/Invitrogen |
| Antibiotic-Antimycotic | 5 mL | 15240-062 | Gibco/Invitrogen |
| B27 Supplement ™ (see Table 4) | 10 mL | 17504-044 | Gibco/Invitrogen |
| Cholesterol (250X) | 5 mL | 12531 | Gibco/Invitrogen |
| Human TNF-alpha | 10 µg | T6674 | Sigma-Aldrich |
| PDGF BB | 50 µg | P4056 | Sigma-Aldrich |
| Vasoactive intestinal peptide (VIP) | 250 µg | V6130 | Sigma-Aldrich |
| Insulin-like growth factor | 25 µg | 12656 | Sigma-Aldrich |
| NAP | 1 mg | 61170 | AnaApec. Inc. |
| Recombinant Apolipoprotein E2 | 50 µg | P2002 | Panvera |
| Laminin, mouse purified | 2 mg | 08-125 | Millipore |
| Beta amyloid (1-40) | 1 mg | AG966 | Millipore |
| Human Tenascin-C protein | 100 µg | CC065 | Millipore |
| rr-Sonic hedgehog, Shh N-terminal | 50 µg | 1314-SH | R&D Systems |
| rr (Agrin C terminal) | 50 µg | 550-AG-100 | R&D Systems |

TABLE 3

Composition of Neurobasal ® medium

| Components | Molecular Weight | Concentration (mg/L) | Concentration (mM) |
|---|---|---|---|
| Glycine | 75 | 30 | 4.00E−01 |
| L-Alanine | 89 | 2 | 2.25E−02 |
| L-Arginine hydrochloride | 211 | 84 | 3.98E−01 |
| L-Asparagine-$H_2O$ | 150 | 0.83 | 5.53E−03 |
| L-Cysteine | 121 | 31.5 | 2.60E−01 |
| L-Histidine hydrochloride-$H_2O$ | 210 | 42 | 2.00E−01 |
| L-Isoleucine | 131 | 105 | 8.02E−01 |
| L-Leucine | 131 | 105 | 8.02E−01 |
| L-Lysine hydrochloride | 183 | 146 | 7.98E−01 |
| L-Methionine | 149 | 30 | 2.01E−01 |
| L-Phenylalanine | 165 | 66 | 4.00E−01 |
| L-Proline | 115 | 7.76 | 6.75E−02 |
| L-Serine | 105 | 42 | 4.00E−01 |
| L-Threonine | 119 | 95 | 7.98E−01 |
| L-Tryptophan | 204 | 16 | 7.84E−02 |
| L-Tyrosine | 181 | 72 | 3.98E−01 |
| L-Valine | 117 | 94 | 8.03E−01 |
| Choline chloride | 140 | 4 | 2.86E−02 |
| D-Calcium pantothenate | 477 | 4 | 8.39E−03 |
| Folic Acid | 441 | 4 | 9.07E−03 |
| Niacinamide | 122 | 4 | 3.28E−02 |
| Pyridoxal hydrochloride | 204 | 4 | 1.96E−02 |
| Riboflavin | 376 | 0.4 | 1.06E−03 |
| Thiamine hydrochloride | 337 | 4 | 1.19E−02 |
| Vitamin B12 | 1355 | 0.0068 | 5.02E+06 |
| i-Inositol | 180 | 7.2 | 4.00E−02 |
| Calcium Chloride ($CaCl_2$) (anhyd.) | 111 | 200 | 1.80E+00 |
| Ferric Nitrate (Fe(NO3)3"9H2O) | 404 | 0.1 | 2.48E+04 |
| Magnesium Chloride (anhydrous) | 95 | 77.3 | 8.14E−01 |
| Potassium Chloride (KCl) | 75 | 400 | 5.33E+00 |
| Sodium Bicarbonate ($NaHCO_3$) | 84 | 2200 | 2.62E+01 |
| Sodium Chloride (NaCl) | 58 | 3000 | 5.17E+01 |
| Sodium Phosphate monobasic (NaH2PO4H2O) | 138 | 125 | 9.06E−01 |
| Zinc sulfate (ZnSO47H2O) | 288 | 0.194 | 6.74E+04 |
| D-Glucose (Dextrose) | 180 | 4500 | 2.50E+01 |
| HEPES | 238 | 2600 | 1.09E+01 |
| Phenol Red | 376.4 | 8.1 | 2.15E−02 |
| Sodium Pyruvate | 110 | 25 | 2.27E−01 |

TABLE 4

Composition of B-27 ™

| Component | Concentration (mg/L) |
|---|---|
| L-Alanine | 2.00E+00 |
| L-Glutamate | 3.70E+00 |
| L-Glutamine | 4.41E+02 |
| L-Proline | 7.76E+00 |
| Biotin | 1.00E−01 |
| Vitamin B12 | 3.40E−01 |
| Corticosterone | 2.00E−02 |
| Progesterone | 6.30E−03 |
| Retinol, all trans (Vit. A) | 1.00E−01 |
| Retinol, acetate | 1.00E−01 |
| Insulin | 4.00E+00 |
| T3 (triodo-L-thyronine) | 2.00E−03 |
| Na pyruvate | 2.50E+01 |
| Lipoic acid (thioctic acid) | 4.70E−02 |
| D,L-α-Tocopherol (vit. E) | 1.00E+00 |
| D,L-α-Tocopherol acetate | 1.00E+00 |
| Catalase | 2.50E+00 |
| Glutathione (reduced) | 1.00E+00 |
| Superoxide dismutase | 2.50E+00 |
| L-Carnitine | 2.00E+00 |
| Ethanolamine | 1.00E+00 |
| D(+)-Galactose | 1.50E+01 |
| HEPES | 2.60E+03 |
| Putrescine | 1.61E+01 |
| Penicillin | 50 IU/mL |
| Streptomycin | 5.00E−01 |
| Selenium | 1.60E−02 |
| Zinc sulfate | 1.94E−01 |
| Linoleic acid | 1.00E+00 |
| Linolenic acid | 1.00E+00 |
| Albumin, bovine | 2.50E+03 |
| Transferrin | 5.00E+00 |

TABLE 5

Composition of GlutaMAX ™

| Component | Concentration |
|---|---|
| L-alanyl-L-glutamine dipeptide | 200 mM |
| NaCl | 0.85% |

NbActiv4™ (available from BrainBits LLC) comprises all of the ingredients in Neurobasal™ (Table 3), B27™ (Table 4), and Glutamax™ (Table 5). NbActiv4™ may also comprise creatine, estrogen, and cholesterol. Therefore, in some embodiments, the disclosed serum-free medium comprises the components listed in Table 3, Table 4, and Table 5, along with creatine, estrogen, and cholesterol.

Some embodiments incorporate multi-organ system medium (MOSM), the formulation of which can be found in Table 6. The base medium in the first row of in Table 6 includes at least Neurobasal® or Neurobasal®-A (Invitrogen 10888 or Invitrogen 21103), B-27™ supplement (ThermoFisher Scientific 17504-044, provided as 50× concentrate), and GlutaMAX™ supplement (ThermoFisher Scientific 35050-061, provided as an 100× concentrate). Optionally, antibiotic-antimycotic (ABAM) can be added to the base medium (ThermoFisher Scientific 15240062, provided as an 100× concentrate). Optionally, G-5 supplement can be added to the base medium (ThermoFisher Scientific 17503012, provided as an 100× concentrate). For example, in some embodiments, the base medium can be composed of 95 mL Neurobasal® (or Neurobasal®-A) medium, 2 mL B27™ supplement, 1 mL GlutaMAX™, 1 mL ABAM, and 1 mL G-5 supplement. In some embodiments, the base medium can be composed of 96 mL Neurobasal® (or Neurobasal®-A) medium, 2 mL B27™ supplement, 1 mL GlutaMAX™, and 1 mL G-5 supplement. In some embodiments, the base medium can be composed of 96 mL Neurobasal® (or Neurobasal®-A) medium, 2 mL B27™ supplement, 1 mL GlutaMAX™, and 1 mL ABAM. In some embodiments, the base medium can be composed of 97 mL Neurobasal® (or Neurobasal®-A) medium, 2 mL B27™ supplement, and 1 mL GlutaMAX™. To the base medium are added the additional components at the example concentrations listed in Table 6 below. Cholesterol may also be added to the MOSM medium.

TABLE 6

Composition of Multi-organ system medium (MOSM)

| component | example concentration | manufacturer | product number |
|---|---|---|---|
| Base medium (Neurobasal ® or Neurobasal ® -A, B-27 ™, GlutaMAX ™, and optionally ABAM, and optionally G-5) | | | |
| Glial Derived Neurotrophic Factor (GDNF) | 10 ng/mL | Cell Sciences | CRG400B |
| Brain-derived Neurotrophic Factor (BDNF) | 20 ng/mL | Cell Sciences | CRB600B |
| Ciliary Neurotrophic Factor (CNTF) | 5 ng/mL | Cell Sciences | CRC400A |
| Neurotrophin-3 (NT-3) | 20 ng/mL | Cell Sciences | CRN500B |
| Neurotrophin-4 (NT-4) | 20 ng/mL | Cell Sciences | CRN501B |
| Vitronectin | 100 ng/mL | Sigma | V8379 |
| Insulin-like Growth Factor 1 (IGF-1) | 10 ng/mL | PeproTech | 100-11 |
| Agrin | 100 ng/mL | R&D | 550-AG-100 |
| adenosine 3',5'-cyclic monophosphate (cAMP) | 1 uM | Sigma | A9501 |
| Laminin | 4 ug/mL | Invitrogen | 23017-015 |
| Sonic Hedgehog, N-terminal peptide (Shh) | 50 ng/mL | R&D | 1845-SH-025 |
| RA | 0.1 uM | Sigma | R2625 |

Typical in vitro assessment of cell functionality and maturation within novel microdevices designed for drug development applications takes place over 1 to 2 weeks in culture. Such time frames have been employed for the assessment of a wide variety of in vitro analogues, including cardiac (Natarajan et al., 2011, Agarwal et al., 2013), lung (Huh et al., 2010), kidney (Subramanian et al., 2010), liver (Wagner et al., 2013), pancreas (Lipsett et al., 2007), skin (Bellas et al., 2012), fat (Kang et al., 2009) and neuronal (Natarajan et al., 2013) tissue models, with little information provided regarding more long-term survival. Longer in vitro culture periods tend to lead to cellular senescence or induction of apoptotic pathways, which can confound data analysis. While useful for a wide variety of basic biomolecular research, such timeframes are of more limited value for the study of chronic disease states and long term drug toxicity studies. Furthermore, when designing multi-organ systems for more accurate modeling of whole body responses (Sung et al., 2013), uniformity with regards to cell survival over extended time periods is preferable. An ability to maintain certain cells for 30 days in vitro is immaterial if other cells within the same culture platform begin to die after 14.

Longer culture periods have been established for certain cell types, and assessment of their development and functional maturation over such timeframes has been assessed. For example, skeletal muscle cultures have been shown to survive in vitro for up to 90 days, during which time they promote phenotype maturation, as evidenced by quantifiable changes in Myosin Heavy Chain isoform composition (Das et al., 2009). The systems disclosed herein can promote the long-term (30+ days) co-culture and functional interaction of skeletal muscle myotubes and motoneurons in defined conditions. The data provided herein demonstrate that maintenance of co-cultures is possible over longer periods provided careful consideration is given to culture variables such as surface, media formulation and correct temporal addition of exogenous stimuli.

The present disclosure includes an in vitro model of biological living systems, such as animals or humans, for example, in response to chemicals or chemical mixtures. Such a model that mimics or simulates in vivo living biological systems reduces dependency on animal testing while providing improved predictions of responses of human or other organisms, such as plants, animals or insects. The present disclosure includes micro cell culture analog (μCCA) methods, systems, and devices. These methods, systems and devices comprise microfabrication techniques, cell culture/tissue engineering and microfluidics. A μCCA device, also referred to herein as "a cell culture analog system device," or a "component", is a physical representation of a physiologically-based pharmacokinetic (PBPK) model, and the functional in vitro systems reproduce in vivo effects of living tissues and organs, such as cardiac pacemaking, muscle dynamics, and neuronal information processing.

The present disclosure includes cell culture analog systems comprising one or a plurality of components comprising cells grown in a microscale cell culture device, also referred to as a μCCA device, comprising one or more chambers or regions, wherein a component, along with cells contained therein a chamber or otherwise, and/or other elements, is analogous to a tissue, an organ or organ system. A component comprises a substrate for cells, such as a container for cells, a chamber, in which cells are contained, grown, acted on and/or maintained in the component. For example, a component may comprise, but is not limited to, a cardiac component comprising patterned biologically functional cardiac myocytes on microelectrode arrays. See U.S. patent application Ser. No. 12/938,701, which is incorporated by reference herein in its entirety for disclosing patterned rat cardiomyocyte cultures on microelectrode arrays in a serum-free medium for the study of cardiac physiology and pharmacology, utilizing a high-throughput technique. A disclosed component comprises a support substrate bearing a multielectrode array (MEA) and a negative surface resistant to cell attachment and deposited on the support substrate covering the MEA. The negative surface bears a pattern ablated on it by, for example, laser photolithography. A positive surface promoting cell attachment is deposited on the pattern ablated on the negative surface and cardiomyocytes adherent to the positive surface and growing aligned along the pattern. This application also teaches methods of making the culture of patterned cardiomyocytes. For example, a method comprises preparing a support substrate bearing a MEA, overlaying on the support substrate a negative surface resistant to cell adherence. The surface can comprise polyethylene glycol covering the MEA. Further, the method comprises ablating a pattern on the negative surface, depositing on the ablated pattern a positive surface promoting cell adherence and including fibronectin, adhering cardiomyocytes on the positive surface, and culturing the cardiomyocytes to grow on the positive patterned surface and align with the patterned surface.

A component may comprise more than one type of cell and may simulate organ systems which are comprised of more than one type of cell. Multicellular interactions, such as between the same cells and/or between different types of cells are included in the methods and compositions of the present disclosure. For example, muscle and neurons, which function in communication in a living body, may be provided in a single component and the cells may form neuromuscular junctions between the neurons and the muscle cells. Cells with genetic alterations may be used in methods and compositions of the present disclosure.

In an aspect, a component may comprise a muscular component comprising muscle cells. See U.S. patent application Ser. No. 12/765,399, now U.S. Pat. No. 9,163,216 which is incorporated by reference herein in its entirety for disclosing methods for lengthening the useful life of a culture of muscles cells by using disclosed mixtures of serum-free media, supplemented with growth factors. Tables 1 and 2 of U.S. Pat. No. 9,163,216 show the individual growth factors, hormones, and neurotransmitters that support muscle and neuromuscular junction development. For example, the composition shown in Table 1 is a formulation for a serum-free medium for culturing motor neurons with adult spinal cord neurons. Table 2 lists additional factors identified in muscle development and neuromuscular junction formation. NBactiv4, used for maintenance of the cells, improves the survival of the skeletal muscle cells.

In an aspect, a component can comprise a neural component. See U.S. patent application Ser. No. 12/117,339, which is incorporated by reference herein in its entirety for disclosing a method of culturing adult mammalian spinal cord neurons so that they exhibit electrical functionality. Table 3 of See U.S. patent application Ser. No. 12/117,339, which shows a non-limiting example of a serum-free culture medium used in the disclosed method.

In an aspect, a component can comprise a kidney-like filtering region, an "other tissues" region, and/or other regions analogous to body structures, organs or organ systems.

In an aspect, a cell culture analog system may comprise a hepatic component comprising liver cells, a gastrointestinal component comprising epithelial cells and/or mucus-producing cells.

In an aspect, a cell culture analog system can comprise an immune component. For example, the immune component can comprise immune cells, and one or more agonists or antagonists of the immune response. The cells of the immune component can, in some embodiments, circulate through the larger μCCA device. In some embodiments, the at least one population of immune cells comprise peripheral blood mononuclear cells (PBMCs). In some embodiment, the at least one population of immune cells comprises granulocytes, such as neutrophils, eosinophils, basophils, and mast cells. In some embodiment, the at least one population of immune cells comprises agranulocytes, such as monocytes, macrophages, lymphocytes, and natural killer (NK) cells. The immune component can also further comprise at least one agonist or antagonist of an innate immune response. The innate immune system, also known as the non-specific immune system or in-born immunity system, is an important subsystem of the overall immune system that recognizes and responds to pathogens in a generic way, but, unlike the adaptive immune system, the system does not confer long-lasting or protective immunity to the host. The immune component can also further comprise at least one agonist or antagonist of an adaptive immune response. The adaptive immune system, also known as the acquired immune system or, is a subsystem of the overall immune system that is composed of highly specialized, systemic cells and processes that eliminate pathogens or prevent their growth. Adaptive immune responses are elicited by antigens. The cells that carry out the adaptive immune response are white blood cells known as lymphocytes. There are two main broad classes adaptive immune response—antibody responses and cell mediated immune response, which are carried by two different lymphocytes (B cells and T cells).

The present disclosure includes methods for determining the effect of an input variable on a culture of cells, comprising contacting the cells of one or a plurality of components with an input variable and monitoring at least one output parameter. For example, a cell culture analog system may comprise a plurality of components comprising an hepatic (liver) component, a cardiac component, a motoneuron component, and a muscle component may be used for testing compounds found in compositions that are commercially available, such as personal care compositions.

Also provided is cell culture analog system as disclosed herein, comprising one or a plurality of components, for example, comprising one or more of patterned biologically functional cardiac myocytes on microelectrode arrays, a hepatic component comprising liver cells, a gastrointestinal component comprising epithelial cells and/or mucus-producing cells, a muscular component comprising muscle cells, a kidney-like filtering component, an "other tissues region", a neural component, a neuromuscular component and/or other components analogous to body structures, organs or organ systems, and optionally, further comprising housing for enclosing the components or a board for immobilizing components. A component may comprise a first microscale chamber having a geometry simulating a first in vivo interaction with culture medium, wherein the first chamber comprises a first inlet and a first outlet for flow of the culture medium, and one or more channels coupled to the inlets and outlets of the chamber. An "any other tissues compartment or "other tissues compartment" represents fluid hold-up or retention in non-adsorbing, non-metabolizing tissues which captures the dynamics of exposure to a chemical in the cell culture analog systems.

An aspect of the present disclosure includes a component that mimics or simulates heart function in organisms, such as a human, animal or insect, comprising cardiac myocytes, surface embedded microelectrodes and patterned substrates on the microelectrode array to monitor the condition of the cardiac chamber in the μCCA in real time and detect both acute and chronic functional toxic effects on the system.

Cultured cardiac myocytes are widely used in toxin detection and in drug development to screen for unwanted cardiac side effects [Meyer 2004]. Cardiac myocytes are almost ideal whole-cell biosensors as they are spontaneously active, can be kept in culture in stable conditions for extended periods [Dhir 2009] and they respond to a wide spectrum of known and unknown toxins. Patterning cardiac myocytes on microelectrode arrays allows for the measurement of more advanced parameters, such as reverse use dependence, variability in QT interval and relative refractory periods [Nataraj an 2011].

A cell culture analog system of the present disclosure includes one or a plurality of components, which provide in vitro reproduction or simulation of a living body, with each component representing an organ or tissue in the living body. In a PBPK mathematical model, these chambers are interconnected in a manner analogous to blood flow in the body. In a μCCA or component, the equations representing metabolism or adsorption in these chambers or compartments are replaced by living cells or tissues (e.g. liver, fat, lung, etc. all in the same device). Systems and devices of the present disclosure may be used for research, testing, diagnosis and insight into underlying biochemical mechanisms and how function is affected. By inserting functional tissues into components comprising mammalian cells or tissues, response from exposure to active agents, such as environmental chemicals, can be measured.

Components, systems and methods can be used with both animal cells and human cells, and non-animal cells such as insect or plant cells, and methods may comprise cross-species extrapolation. A basic concept of a μCCA has been demonstrated with studies on naphthalene toxicity (Sin 2004; Viravaidya 2004) on drug combinations to treat multidrug resistant cancer [Tatosain 2009] or colon cancer [Sung 2009] and, in preliminary studies, on hormone disruptors [Xu 2008]. The functional in vitro systems have been demonstrated for cardiac [Natarajan 2011; Natarajan 2006; Das 2004], neuronal [Jung 1998; Mohan 2006], muscle (Das 2007; Wilson 2007; Wilson 2010) and neuromuscular junction [Das 2010, Liu 2005] systems. See U.S. patent application Ser. No. 12/765,996, which is incorporated by reference herein in its entirety for disclosing long term in vitro cultures of tissue engineered functional neuromuscular junctions. Tables 1, 2, and 3 show the serum-free medium used in the disclosed methods. See also U.S. patent application Ser. No. 13/102,672, which is incorporated by reference herein in its entirety for disclosing the formation of neuromuscular junctions in a defined system by co-culturing one or more human motor neuron cells and one or more rat muscle cells in a substantially serum-free medium. Tables 1, 2, and 3 represent non-limiting examples of serum-free media used in the disclosed methods.

Incorporation of a functional cardiac system in component enables the discovery of complex, unknown and unexpected effects of active agents, such as toxicants. Reverse use dependence, variability in QT intervals and relative refractory period (which is related to triangulation) are measured in an in vitro system based on patterned cardiac myocytes. The in vitro electrophysiological measurement parameters are analogous to the parameters used in the SCREENIT scoring system introduced by Hondeghem and coworkers in 1994. In that model, variability in action potential (AP) duration, triangulation of the repolarization phase of the AP and reverse use dependence is measured on female rabbit Langendorff-perfused hearts. This in vitro system does not reproduce the whole complexity of the heart but shows that the measured parameters are able to measure the most important arrhythmogenic mechanisms including rhythm generation (chronotropy, firing frequency dispersion), conduction (conduction velocity, conduction velocity dispersion, frequency dependence of conduction velocity) and re-entry (QT interval, QT interval dispersion, reverse use dependence, absolute and relative refractory period). These parameters have high predictive value for cardiac side effects. In addition, by utilizing a serum-free, defined culture medium, as disclosed herein, one of the major unknown variables in the system would be removed.

As an example of the utility of a functional cardiac system within a component, Example 1 of U.S. application Ser. No. 14/422,082 discloses a system combining liver, cardiac, and "other tissues" components or compartments. For the validation of an integrated cardiac myocyte reporter construct and a μCCA, the effect of metabolism on the functional effects of stereoisomers of permethrin, a pyrethroid and an environmental toxin, was measured. The role of enantioselectivity in environmental safety is poorly understood for pesticides, and the knowledge gap is reflected in that the great majority of chiral pesticides are used and regulated as if they were achiral, that is, single compounds. Stereoisomerism is critically important for pyrethroid toxicity; it determines not only their efficacy on their main target, but more importantly, their metabolic rate. Components, arrays and methods are ideal in vitro systems to study the effect of metabolism on the effect of environmental toxins in a system that is adaptable to a high-throughput format. For example, an in vitro system that allows for the observation of functional units derived from human cells/tissues is advantageous for environmental toxin studies. In a non-limiting example, human stem cells can be used for more authentic constructs leading to human-based components, arrays, and methods. Thus, the systems described in U.S. application Ser. No. 14/422,082 are components, arrays and methods using specific organ systems represented by in vitro models, including, but not limited to, for example, a cardiac analog using patterned cardiac myocytes.

The present disclosure includes cells, including but not limited to, animal, human, plant or insect cells, and provides data that can reduce dependency on animals for testing and provides insights that cannot be obtained from whole animals. The present disclosure can lead to a more accurate and cost-effective assessment of the toxicological potential of environment chemicals or chemical mixtures. Aspects of the present disclosure combine both "cell culture analogs" (CCA) with the development of functional tissue mimics. These approaches are combined to make a realistic in vitro model of a mammal and predict its response from exposure to a chemical or chemical mixture, referred to herein as an active agent, whether particularly active on a cell or not. The present disclosure may comprise systems for functional muscle as well as neuronal systems. The present disclosure may comprise use of human stem cells for more authentic constructs leading to a human based components, systems and methods.

The present disclosure comprises a physical representation of a physiological based pharmacokinetic (PBPK) model. A PBPK model is a mathematical representation of the body, which treats the body as a set of interconnected compartments, each of which describes an organ or tissue. Each compartment is modeled as a chemical reactor, absorber, or surge tank. A set of reactive mass balances on parental compounds and metabolites are written for each compartment. Blood flow in and out of each compartment is simulated to match measured values. The model predicts the time dependent changes in the plasma and tissue compartment concentrations of parental compounds and metabolites. A person of skill would know that these mathematical models have been used in numerous studies on the toxicology of environmental chemicals.

While such computational models have proven to be useful aids in studies of absorption, distribution, metabolism, elimination, and toxicity (ADMET), they are limited. All relevant reactions and physiological responses are identified, particularly molecular mechanisms underlying cell response. For complex systems, such as mammals, it is difficult to capture not only the primary reactions but also all of the secondary responses (e.g., the metabolite of A, made in the liver, circulates to another tissue causing the release of B which then causes other cells to change physiologically). The disclosed components, arrays and methods compensate for this lack of complete knowledge.

In addition to the limitations of current in vitro tests to predict systemic effects, most assays are based on single cell analysis. It is well known that single cells are limited in their ability to mimic in vivo tissue function. Recently, functional cellular models, or multicellular systems that allow evaluation of properties previously only possible in intact animals or organs such as muscle dynamics [Wilson 2010], cardiac pacemaking [Nataraj an 2011], neuronal function [Varghese 2010] and neuromuscular junction (NMJ) function [Guo 2010], have been developed to overcome these limitations but have not as yet been integrated. The disclosed components, arrays and methods provide a combination of these functional in vitro systems into a system that more accurately recapitulates the human response.

Components, systems and methods of the present disclosure comprise physical replicas of a PBPK model with multiple types of mammalian cells cultured in a component instead of a mathematical description of the metabolism or absorption. Thus, the physiology of the cells compensates for lack of prior or incomplete knowledge. In an aspect, the fluid fraction feeding each component functions as the blood fraction received by the corresponding organ in vivo. Fluid is re-circulated just as in the body. Also, the fluid residence time, which describes the duration of cell-compound contact, in each component equals its in vivo value. For well-mixed systems, this residence time controls the amount of reaction. The liquid to cell ratio in each cell culture unit is managed to be as close as possible to its physiological value. Shear stress introduced by the flow is calculated and is kept at the physiological value for that type of tissue. Shuler described and constructed the first CCA and demonstrated its potential usefulness with naphthalene as a model toxicant in 1995. The initial device and several subsequent studies used bench scale systems. In later studies, the CCA's were constructed as microfabricated devices.

An advantage of the components, arrays (systems) and methods of the present disclosure is that they are relatively inexpensive to make and can support high throughput studies. Further, the natural length scale (10 to 100 μnm) is consistent with physiological length scales. Unlike other in vitro systems, such as multi-well plates, the disclosed components, systems and methods provide realistic dose dynamics (similar to what occurs in an animal or human) and allow for the formation and exchange of metabolites between compartments as well as exchange of compounds induced by the presence of the parental compound or metabolites. Coupling of the PBPK to the CCA and then to functional systems, as do the components, arrays (systems) and methods of the present disclosure is straightforward and can be used to test underlying molecular mechanisms.

Shuler has demonstrated the μCCA concept with naphthalene (Sin 2004; Viravaidya 2004), showing that naphthaquinone (rather than naphthalene epoxide) was the reactive metabolite generated in the liver causing gluthathione depletion and loss of viability in the lung compartment. Subsequent studies examined the response to drug combinations. While animal studies are expensive with a single compound, such studies become even more difficult when chemical mixtures are to be tested. The combinations and permutations become large when several compounds are tested, particularly when each compound can involve multiple doses and when the order of exposure may be important. For example, the use of doxorubicin was tested with two multi-drug resistant (MDR) suppressing compounds (cyclosporine and nicardipine) for the treatment of MDR cancer (Tatosian 2009); the action of the two MDR suppressors was found to be synergistic in the μCCA, but this was not observable in multi-well plate assays. The use of Tegafur (a pro-drug for 5-flurouracil (5-FU)) and uracil combination treatment was examined for colon cancer using both a PK-PD model and a μCCA (Sung 2009). As observed in animal trials, the μCCA predicted that a uracil to Tegafur ratio of 4 to 1 was optimal in maximizing the concentration of 5-FU in the tumor relative to that in the blood. Unlike multi-well plates, the system indicated that 5-FU must be produced in the liver and circulate to the tumor to kill cells and that uracil (which inhibits the enzyme dihydroprymidinedehydrogenase) enhances the toxicity of Tegafur.

Technical enhancements to the μCCA system such as bubble traps, use of human reporter cell lines, and techniques to image the system in near real time have been made. A further enhancement involves connecting this model of systemic circulation with a model of a barrier tissue that controls entry into the body. Models of the gastrointestinal (GI) tract to model response to oral absorption of chemicals and drugs have also been constructed.

These initial CCA studies have been done primarily with cell lines either as monolayers or embedded in hydrogels. Such unorganized cell systems often lack key enzymes at realistic levels, and the biological functionality of the tissue is not well represented. Further measurements have been based solely on optically accessible end points such as fluorescence (e.g., dye reaction with gluthathione, uptake of naturally fluorescent compounds, viability stains, or reporter proteins, such as GFP). The addition of biologically functional tissues, such as patterned cardiac myocytes integrated with Microelectrode Arrays (MEAs), increases the information control and allows for the use of electrical measurements to monitor response.

An aspect of the components, arrays and methods of the present disclosure comprises using monitoring methods, which are 1) non-invasive, 2) more high throughput, 3) high information content, 4) functional, 5) able to detect known and unknown effects of active agents at physiological concentrations, 6) appropriate for continuous monitoring, 7) compatible with fluidic systems, and 8) mechanically robust. Hybrid (live-cell/electronic) systems have been developed to overcome several shortcomings of traditional whole-cell biosensors, at the same time preserving their advantageous properties over traditional physico-chemical or biochemical sensing methods.

An aspect of the present disclosure includes a method which utilizes a cellular construct comprising cardiac myocytes, surface embedded microelectrodes and patterned substrates on the microelectrode array to monitor the condition of the cardiac chamber in a device of the present disclosure in real time. Cultured cardiac myocytes are widely used in toxin detection and in drug development to screen for unwanted cardiac side effects (Meyer 2004). It has been shown that pyrethroids (Nataraj an 2006) and heavy metals can be detected, and in some extent classified, based on their physiological effects on the spontaneous activity of cultured cardiac myocytes measured using a non-invasive, high-throughput, chronic protocol with substrate-embedded MEAs.

By using an appropriate double-stimulation protocol and 'collide' action potentials at the intersection of line patterns with variable delay, the measurement of action potential length, the absolute and relative refractory period as well as measurement of the effects of 1-Heptanol can be achieved. This functional assay, combined with components, arrays and method of the present disclosure, allows for the observation of systemic effects of compounds on parameters that are normally used in vivo to monitor human health. This is a major advance for increasing the relevance of in vitro systems to predict effects on a mammal's response to active agents, such as toxins. This patterned cardiac system has also been shown to be responsive to sparfloxacin, an antibiotic known to cause fibrillation as recently shown.

An aspect of the present disclosure includes components, systems and methods comprising a "liver" analog region to mimic metabolism, a patterned cardiac myocyte/MEA functional reporter region, and an "other tissues" region, which is a compartment without any cells that represents the holdup of recirculating fluid in tissues where there is no adsorption or metabolism. For example, the present disclosure allows for the validation of the integrated cardiac myocyte reporter region and the functional effects of stereoisomers of permethrin (a pyrethroid which is an environmental toxin) on the tissues in the system can be measured. Permethrin has four stereospecific isomers: 1R-cis-, 1R-trans-, 1S-cis-, and 1S-trans-. The 1R-cis- and 1R-trans-isomers are active, whereas the other two are not. Moreover, the cis isomers are about ten times more toxic than the trans isomers in vivo. Recent data indicated that the metabolic rate of cis-permethrin is much slower than that of the trans isoform, which could be an explanation for the different in vivo toxicity.

An aspect of the present disclosure includes components, systems and methods that can be used to determine and measure the effect of different enantiomers, for example permethrin, on spontaneous beating and conduction velocity of patterned cardiac myocytes in the presence and absence of one or more chambers of a component representing the major metabolic pathways in the body. The lifetime of components can be extended to examine the effects of a compound in chronic studies.

The present disclosure includes components, arrays and methods comprising patterned biologically functional cardiac myocytes on microelectrode arrays and other chambers comprising cells, structures, factors, co-factors or other elements for constructing analogs of organ tissues or systems that mimic physiological, physical, chemical, and/or electrical conditions of whole organisms.

The present disclosure includes methods for determining the effect of an input variable on components, arrays and methods, comprising contacting cells comprised by one or more components with an input variable and monitoring at least one output parameter. For example, components, arrays and methods may comprise testing of active agents for beneficial or deleterious effects, long-term studies of exposure to active agents, determination of active metabolites or other studies designed by those skilled in the art using the components, arrays and methods of the present disclosure.

An aspect of the present disclosure includes components and/or systems comprising a housing for enclosing a component and/or systems disclosed herein, at least one component, wherein a component may be a microscale chamber having a geometry that simulates an in vivo interaction with culture medium, wherein the chamber comprises a first inlet and a first outlet for flow of the culture medium, and channels coupled to the inlets and outlets of the chamber. A component or system may be held in place or immobilized by attachment to or association with a board, a planar solid, to which the one or more components of a system are attached or associated.

An aspect of the present disclosure includes cell culture analog systems comprising one or a plurality of components, wherein a component comprises a cardiac component, a neural component, a gastrointestinal component, a kidney-like component, an immune component, an other tissues component or a hepatic component. A cell culture analog system comprises a cell culture analog system comprising a cardiac component, an immune component, and a hepatic component. A system comprises a cell culture analog system comprising a plurality of components comprising a cardiac component, a neural component, an immune component, and a hepatic component. A cell culture analog system comprises a cell culture analog system comprising a plurality of components comprising a cardiac component, a neural component, a gastrointestinal component, an immune component, and a hepatic component. A cell culture analog system comprises a cell culture analog system comprising a plurality of components comprising a cardiac component, a neural component, a gastrointestinal component, a kidney-like component, an immune component, and a hepatic component. A cell culture analog system comprises a cell culture analog system comprising a plurality of components comprising a cardiac component, a neural component, a gastrointestinal component, a kidney-like component, an other tissues component, a neuromuscular component, a muscular component, an immune component, and a hepatic component. A cell culture analog system comprises a cell culture analog system comprising a plurality of components comprising a cardiac component, a neural component, a gastrointestinal component, a kidney-like component, an other tissues component, a neuromuscular component, a muscle component, an immune component, and a hepatic component. A cell culture analog system comprises a cell culture analog system comprising a plurality of components comprising a neural component, a gastrointestinal component, a kidney-like component, an other tissues component, an immune component, and a hepatic component. A cell culture analog system comprises a cell culture analog system comprising a plurality of components comprising a gastrointestinal component, a kidney-like component, an other tissues component, an immune component, and a hepatic component. A cell culture analog system comprises a cell culture analog system comprising a plurality of components comprising an other tissues component, an immune component, and a hepatic component. A cell culture analog system comprises a cell culture analog system comprising a plurality of components comprising a cardiac component, a gastrointestinal component, a kidney-like component, an other tissues component, an immune component, and a hepatic component. A cell culture analog system comprises a cell culture analog system comprising a plurality of components comprising a cardiac component, a kidney-like component, an other tissues component, an immune component, and a hepatic component. A cell culture analog system comprises a cell culture analog system comprising a plurality of components comprising a cardiac component, an other tissues component, an immune component, and a hepatic component. A cell culture analog system comprises a cell culture analog system comprising a plurality of components comprising a cardiac component, an immune component, and a gastrointestinal component. A cell culture analog system comprises a cell culture analog system comprising a plurality of components comprising a cardiac component, an immune component, and a kidney-like component. A cell culture analog system comprises a cell culture analog system comprising a plurality of components comprising a cardiac component, a neuromuscular component, a muscle component, an immune component, and a hepatic component. An aspect of the present disclosure includes a cell culture analog system comprising one component, two components, three components, four components, five components, six components, seven components, eight components, or more than eight components.

The present disclosure includes methods, systems and means for dynamically controlling a cell culture analog system, for example, comprising a computer and other elements, such as processors, sensors, actuators, etc., wherein, in an aspect, a method comprises analyzing data from a plurality of sensors to measure physiological events in one or more chambers of one or more components disclosed herein; optionally, regulating a cell culture characteristic such as temperature, light, oxygen, carbon dioxide, and/or fluid flow rates of a culture medium in at least one chamber of a component; and detecting biological or toxicological reactions in the cells or other elements of one or more chambers of a component; and optionally, upon detection, recording the change and/or changing one or more pharmacokinetic parameters of a component.

The present disclosure includes a computer-readable medium having computer-executable instructions stored thereon to perform a method. For example, a method may comprise analyzing data from a plurality of sensors to measure physiological events in one or more chambers of one or more components disclosed herein; optionally, regulating a characteristic such as temperature, light, oxygen, carbon dioxide, and/or fluid flow rates of a culture medium in at least one chamber of a component; and detecting biological or toxicological reactions in the cells or other elements of one or more chambers of a component; and optionally, upon detection, recording the change and/or changing one or more pharmacokinetic parameters of component.

An aspect of a cell culture analog system comprises the arrangement of the components in a system. A component may be in fluid connection with one or more components or conduits for fluid connection. A component may be a defined area in a solid material, such as a chamber formed by removal of a portion of the solid material to form an indentation or well in the solid material, such as the wells connected by fluid connections or channels formed in a solid material. See U.S. application Ser. No. 14/422,082 for examples of wells configured to be in fluid connection via channels connecting the wells. In an aspect, gravity can move fluid from component to component.

An aspect of a system of the present disclosure may comprise placing one or more components or portions of components on a platform that is capable of movement. In an aspect, a movable platform can allow gravity to affect or to drive fluid flow. For example, the component may be tilted. A method of the present disclosure may comprise tilting or moving a component from a position substantially parallel to a particular reference location, such as the earth's surface, or to a position at an angle to the particular reference location, such as the earth's surface. The tilting motion may be a one time, intermittently or constantly occurring for the component and/or system. A system or component of the present disclosure may comprise a movable stage that moves a cell culture analog system or component from a first position relative to a reference point to at least one different position, and may or may not return the system or component to the first position. For example, a system, component or method comprising a system and/or component may comprise a moveable platform on which a system or component is placed such that the system and/or component may be moved from a first position to at least one different position if movement is desired. A portion of a system or component may be configured to be moveable such that the portion may be moved from a first position to at least one different position if movement is desired. As used herein, tilting means moving a system or component of a system or a portion of a system or a component from a first position in three dimensional space to at least one different position in three dimensional space. A tilting action may include, but is not limited to, a one-time tilt wherein the system or component moves from one position to a second position; or may include tilting in a continuous or intermittent pattern between one or more positions other than the first position. Tilting may occur in a smooth, non-liner function. Tilting may be in a step function, for example, the system, component or portion thereof, may be moved from a first position to a one or more other positions, such as a tilt to a 10° position from the first position, pause at the second position, tilt to a 20° position from the first position, pause at the third position, tilt to a 30° position, pause at the fourth position, return tilt to a 20° position from the first position, pause at the third position, return tilt to a 10° position from the first position, pause at the second position, return to the first position, and optionally, repeat one or more times. Tilting may be in a single step function. For example, move the system or component quickly to +30° from the starting position, pause, move quickly to −30°, pause, back to +30°, and optionally, repeat one or more times.

An aspect of movement of a system or component or portion thereof comprises the time the system, component or portion thereof remains in one or more positions. Such time may be brief or long, from seconds to minutes to days to weeks, and may be determined by one of skill in the art, or may be used to mix compositions comprising media, cellular factors, cells, compounds to be tested, or other ingredients in a component or between components in a system. The period of movement of the system may be brief or long-term, and may be for seconds, minutes days or weeks, and may occur continuously from the start-up of a system or component to completion, or for one or more times during the use of the system or component, or may occur intermittently or randomly during the use of the system or component.

The movement of a system, component or portion thereof, may be uniform or non-uniform in any aspect, such as in time at a position, in time between movements, speed of the movement from one position to another, degree of tilt from the horizontal axis, number of cycles of movement from one position to one or more other positions, and combinations of these aspects. The amount and type of movement of a system, component or position thereof may be determined by keeping the flow rate constant to and between one or more components, a need to produce time-dependent flow rates or time dependent shear stresses, and/or to produce flow and movement to and between one or more components to mimic blood flow and conditions found in fluid dynamics in a living organism.

Figures 12A, 12B, 12C:
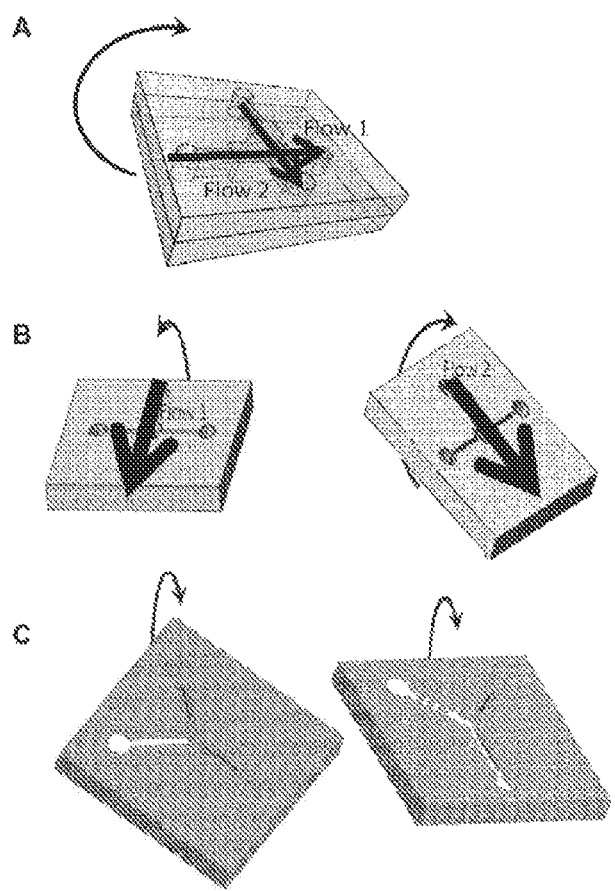
FIGS. 12A-12C show mixing of compositions in components that may be controlled by smooth, non-linear tilting of the component or a portion of the component.

As shown in FIG. 12A, the design of the tilt direction and the flow paths may be used to produce two or more separate flows of liquid compositions in and/or between one or more components. By controlling the orientation of the component in three dimensional space, there may be, for example, two separate flows of liquid in separate components, or intersecting flows between components. As shown in FIG. 12A, a system can comprise two components, wherein the components are in fluid connection with a media well, respectively, through fluid channels. Fluid in a media well can be moved from one media well to a different media well, the media flow Flow 2 traverses a component, and may or may not be mixed with the media from Flow 1. By determining the orientation of the component in three dimensional space, the ratios of mixed fluids may be controlled, for example the ratio of the amount of flow 1 mixed with flow 2 may be controlled by the axis of tilt of the flow paths.

In FIGS. 12B1 and 12B2, and 12C1 and 12C2, only the fluid flow paths are shown, and components are not shown. In 12B1, with a particular tilt or orientation of a system or components (not shown), fluid will flow from well to well and not to the other wells. A mixing well may be located between one or more wells. In 12B2, in a different tilt or orientation of a system or component, fluid flows from media well to media well. Other aspects of moving fluids or mixing fluids are shown in FIGS. 12C1 and 12C2. In FIG. 12C1, fluids move but are not mixed, and in FIG. 12C2, two fluids flow and are mixed.

Figures 13A, 13B, 13C, 13D:
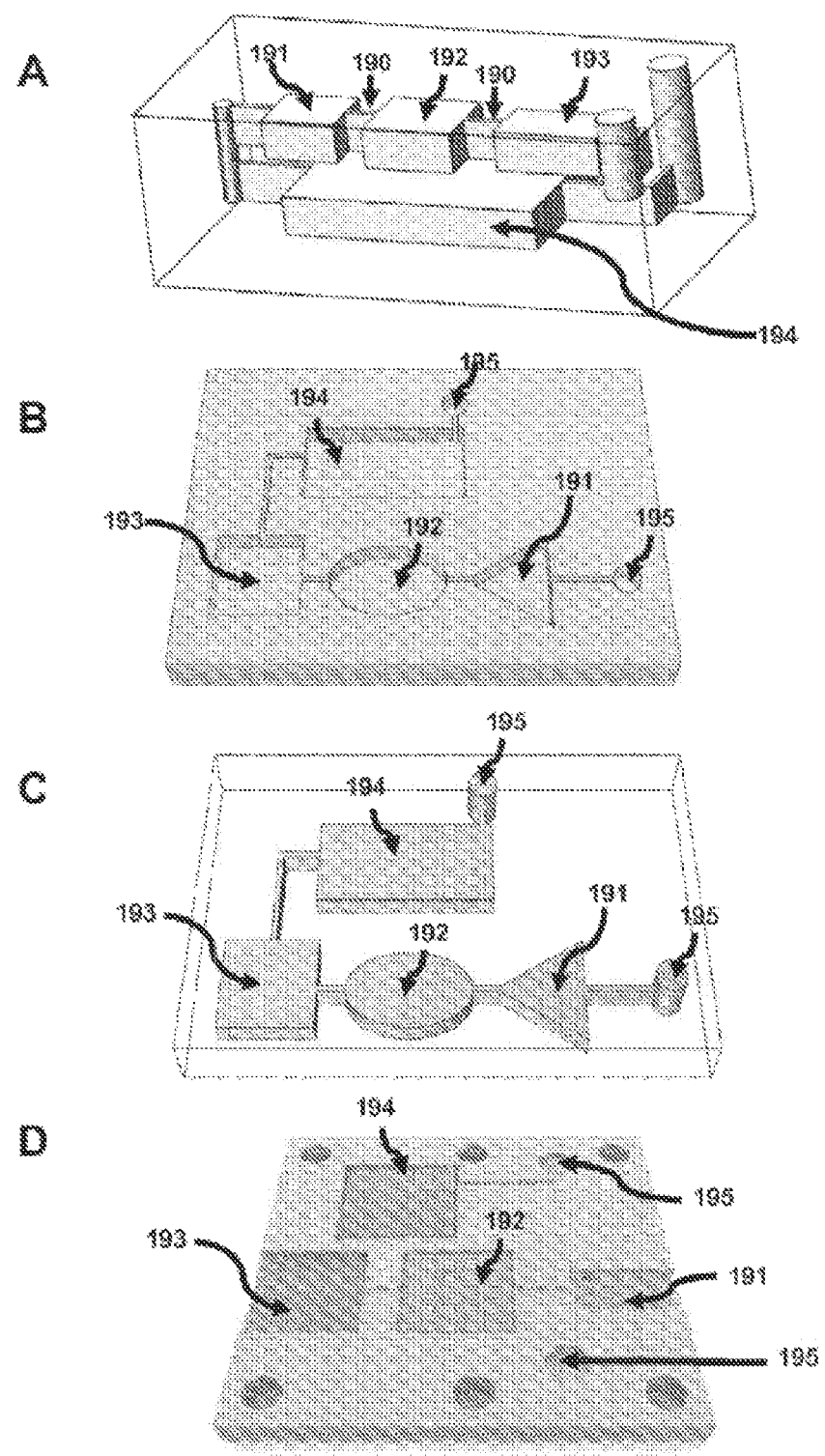
FIGS. 13A-13D shows exemplary embodiments for cell culture analog systems of the present invention.

FIG. 13A shows an arrangement of components wherein the components are in fluid connection with one or more components. For example, component 191 is in fluid connection with component 192 through connection 190, and with component 194. Component 192 is in fluid connection with component 191 through connection 190, with component 193 through connection 190, and component 194. Component 193 is in fluid connection with component 192 through connection 190, and with component 194. Components in a system may be positioned in any physical relationship that is functional for the operation of the system. In FIG. 13B, a system is in a planar sequential arrangement wherein one component is in fluid connection with the adjacent component(s) or a well 193. Components 191-194 are shown in fluid connection by connection 190. The components may be formed in a solid material and individual elements may be added to the indented space(s) in the solid material. See FIG. 13B. The components may be assembled in a planar relationship to one another, see FIG. 13C. A solid planar material may be used to immobilize one or more components, and fluid connections may be channels formed in the solid material to fluidly connect the components. See FIG. 13D where individual components 191, 192, 195, and 194 are placed within shaped wells to hold the components in place and connections 190 fluidly connect wells 193, for example, for containing media, to components arranged in a serial relationship. The present disclosure comprises parallel arrangements of components.

The present disclosure includes in vitro methods and systems for mimicking the in vivo metabolism and response to stimuli of tissues, organs, organ systems of living organisms. A method of the present disclosure determining the effect of an input variable on a simulated multi-organ system, comprising contacting at least one cell in a cell culture analog system which comprises a plurality of components, wherein a component comprises one or more chambers, chips or regions, and optionally, one or more types of cells; and one or more sensing elements, wherein one or more of the plurality of components is in fluid connection with another component, with an input variable and recording at least one output parameter. The method may comprise measuring and recording more than one output parameter, or a plurality of output parameters from a plurality of components. A step of recording at least one output parameter comprises obtaining information from a sensing element in a component.

A system may comprise a plurality of components of which at least one component is a cardiac-simulating component comprising cardiac cells cultured on one or more microcantilevers. A cardiac-simulating component may comprise cardiac cells cultured in a pattern on a microelectrode array with embedded microelectrodes. A system may comprise a plurality of components of which at least one component is a motoneuron component comprising neurons and myotubes forming neuromuscular junctions cultured on microcantilevers. A motoneuron component may comprise neurons and myotubes forming neuromuscular junctions cultured in a pattern on a microelectrode array with embedded microelectrodes. A system may comprise a plurality of components of which at least two component is a cardiac-simulating component and a motoneuron component. A component may comprise a tissue biopsy, such as ex plant tissue from a body, for example a dissected portion of a tissue or organ.

A cell culture analog system may further comprise connection elements, pumps, filters, sensors, alarms, and computer control elements. One or more components may be a microfluidic device. The cells may be derived from a human, an animal, a plant or an insect, or combinations and mixtures thereof. The cell culture analog system may further comprise serum-free culture medium.

A cell culture analog system may comprise at least a first component comprising a microscale chamber containing a first type of cell under conditions where the first type of cell provides at least one pharmacokinetic parameter value comparable to a value obtained for the same type of cell in vivo, wherein the first chamber comprises a first inlet and a first outlet for flow of culture medium; and comprises, a second component comprising a microscale chamber containing a second type of cell under conditions where the second type of cell provides at least one pharmacokinetic parameter value comparable to a value obtained for the same type of cell in vivo, wherein the second chamber comprises a second inlet and a second outlet for flow of culture medium; and a microfluidic channel interconnecting the first and second chambers. At least one component may comprise a first chamber comprising a first cell type maintained under conditions providing at least one pharmacokinetic parameter value comparable to values obtained for the cells in vivo; a second component comprises a second chamber of the same or different geometry than the first chamber comprising a second cell type maintained under conditions providing at least one pharmacokinetic parameter value comparable to values obtained for the cells in vivo; wherein the first and second chambers are interconnected by fluidic channels; and an inlet and outlet for re-circulation of culture medium.

In a method for testing the response(s) of a cell culture analog system to an input variable, an input variable may be an organic or inorganic chemical compound. An input variable may be more than one compound, and may be a mixture of inorganic and organic compounds. An input variable be may a pharmaceutical composition, an environmental sample, a nutritional sample, or a consumer product. An input variable may be a virus, liposome, nanoparticle, biodegradable polymer, radiolabeled particle or toxin, biomolecule, toxin-conjugated particle or biomolecule. The time period for testing the reaction of one or a plurality of components in a cell culture analog system may be for 72 hours, 84 hours, 96 hours, 108 hours, 120 hours, 132 hours, 144 hours, 156 hours, 168 hours, 180 hours, or for days or weeks, or longer, or any amount of time in between.

A cell culture analog system of the present disclosure may comprise a plurality of components, wherein a component comprises one or more chambers, chips or regions, and one or more types of cells; and one or more sensing elements, wherein one or more of the plurality of components is in fluid connection with another component. The system may further comprise connection elements, pumps, filters, sensors, alarms, and computer control elements. A component of the system may be a microfluidic device. The cells of the components of the system may be derived from a human, an animal, a plant or an insect, or combinations and mixtures thereof. At least one component may comprise a chip comprising biological cells on a microelectrode array comprising surface embedded microelectrodes. A cell culture analog system comprises at least one serum-free fluid culture medium.

A cell culture analog system may comprise at least one component comprising at least a first microscale chamber containing a first type of cell under conditions where the first type of cell provides at least one pharmacokinetic parameter value comparable to a value obtained for the same type of cell in vivo, wherein the first chamber comprises a first inlet and a first outlet for flow of culture medium; and optionally comprises, a second component comprising a second microscale chamber containing a second type of cell under conditions where the second type of cell provides at least one pharmacokinetic parameter value comparable to a value obtained for the same type of cell in vivo, wherein the second chamber comprises a second inlet and a second outlet for flow of culture medium; and a microfluidic channel interconnecting the first and second chambers. A cell culture analog system may comprise at least one component comprising a first chamber comprising a first cell type maintained under conditions providing at least one pharmacokinetic parameter value comparable to values obtained for the cells in vivo; and a second component comprising a second chamber of the same or different geometry than the first chamber comprising a second cell type maintained under conditions providing at least one pharmacokinetic parameter value comparable to values obtained for the cells in vivo; wherein the first and second chambers are interconnected by fluidic channels; and an inlet and outlet for re-circulation of culture medium. A cell culture analog system may comprise one or more additional microscale chambers containing the same or different types of cells as in the first or optionally second chambers, under conditions where the additional cell provides at least one pharmacokinetic parameter value comparable to a value obtained for the same type of cell in vivo, wherein the one or more additional chambers comprise an inlet and outlet for flow of culture medium. A cell culture analog system may operate for 72 hours, 84 hours, 96 hours, 108 hours, 120 hours, 132 hours, 144 hours, 156 hours, 168 hours, 180 hours, or for days or weeks, or longer, or any amount of time in between.

A cell analog system may use one or more culture media. For example, the entire system may use one culture media, such as a serum-free media, and that media may be circulated to one or more of the components in fluid connection in the system. Individual media components, such as nutritional compounds or growth cell factors may be added in individual components, and may or may not be circulated to other components of the system. The cells in a component may be grown and develop to the desired stage or number of cells in a component using a particular culture media and then that component may be joined into a cell analog system in which a different culture media, such as a serum-free media, is circulated throughout the entire system. A cell analog system of the present disclosure may comprise use of one culture media in each connected component. A cell analog system of the present disclosure may comprise use of more than one culture media, at different times during the operation of the system, or in different individual components.

It is to be understood that this disclosure is not limited to particular methods, and as such may, of course, vary. It is also to be understood that the terminology used herein is for the purpose of describing particular embodiments only and is not intended to be limiting.

All patents, patent applications, and other referenced articles, journals or references referred to herein are each hereby expressly incorporated in its entirety.

As used in the specification and the appended claims, the singular forms "a," "an" and "the" include plural referents unless the context clearly dictates otherwise. The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not. For example, the phrase "optionally obtained prior to treatment" means obtained before treatment, after treatment, or not at all.

As used throughout, by "subject" is meant an individual. Preferably, the subject is a mammal such as a primate, and, more preferably, a human. Non-human primates include marmosets, monkeys, chimpanzees, gorillas, orangutans, and gibbons, to name a few. The term "subject" includes domesticated animals, such as cats, dogs, etc., livestock (for example, cattle, horses, pigs, sheep, goats, etc.), laboratory animals (for example, ferret, chinchilla, mouse, rabbit, rat, gerbil, guinea pig, etc.) and avian species (for example, chickens, turkeys, ducks, pheasants, pigeons, doves, parrots, cockatoos, geese, etc.). The subjects of the present disclosure can also include, but are not limited to fish (for example, zebrafish, goldfish, tilapia, salmon and trout), amphibians and reptiles.

Throughout this application, various publications and patent applications are referenced. The disclosures of these publications in their entireties are hereby incorporated by reference into this application in order to more fully describe the state of the art to which this disclosure pertains.

It will be apparent to those skilled in the art that various modifications and variations can be made in the present disclosure without departing from the scope or spirit of the disclosure. Other embodiments of the disclosure will be apparent to those skilled in the art from consideration of the specification and practice of the systems and methods disclosed herein. It is intended that the specification and examples be considered as exemplary only, with a true scope and spirit of the disclosure being indicated by the following claims.

The disclosure of each of the following patent applications is herein incorporated by reference in its entirety: U.S. patent application Ser. No. 14/422,082 filed on Feb. 17, 2015 and titled "METHODS, SYSTEMS, AND COMPOSITIONS FOR FUNCTIONAL IN VITRO CELLULAR MODELS OF MAMMALIAN SYSTEMS", (1) U.S. patent application Ser. No. 12/661,323 filed on Mar. 15, 2000 and titled "Bio-Microelectromechanical System Transducer and Associated Methods", (2) U.S. patent application Ser. No. 12/765,399 filed on Apr. 22, 2010 and titled "Method for Culturing Skeletal Muscle for Tissue Engineering", (3) U.S. patent application Ser. No. 12/938,701 filed Nov. 3, 2010 and titled "Patterned Cardiomyocyte Culture on Microelectrode Array", (4) U.S. patent application Ser. No. 13/102,672 filed on May 6, 2011 and titled "Formation of Neuromuscular Junctions in a Defined System", (5) U.S. patent application Ser. No. 12/145,810 filed Jun. 25, 2008 and titled "Cell Culture Media and Process for Differentiation of Human Spinal Cord Stem Cells into Functional Motor Neuron Cells", (6) U.S. patent application Ser. No. 13/576,442 filed Feb. 7, 2011 and titled "Model and Methods for Identifying Points of Action in Electrically Active Cells", (7) U.S. patent application Ser. No. 13/696,396 filed May 6, 2011 and titled "Formation of Neuromuscular Junctions", (8) U.S. patent application Ser. No. 12/117,339 filed May 8, 2008 and titled "Culture of Electrically Functional Adult Spinal Cord Neurons and Associated Methods", (9) U.S. patent application Ser. No. 12/788,732 filed May 27, 2010 and titled "Method of Myelinating Isolated Motoneurons", (10) U.S. patent application Ser. No. 12/765,996 filed Apr. 23, 2010 and titled "Long Term In Vitro Culture of Tissue Engineered Functional Neuromuscular Junctions", (11) U.S. patent application Ser. No. 13/322,903 filed on May 28, 2010 and titled "In Vitro Production of Oligodendrocytes from Human Umbilical Cord Stem Cells", and (12) U.S. patent application Ser. No. 13/322,911 filed May 27, 2010 and titled "Method of Screening Drugs for Reversal of Amyloid Beta Neurotoxicity", U.S. Provisional Patent Application Nos. 61/684,168, filed Aug. 17, 2012; 61/758,628, filed Jan. 30, 2013; 61/732,042, filed Nov. 30, 2012; 61/732,574, filed Dec. 3, 2012; and U.S. Provisional Patent Application Ser. No. 61/784,923, titled "Compositions and Methods for Generating Neural Crest Cells", an inventor James Hickman, filed Mar. 14, 2013; and applications concurrently filed herewith and each incorporated in its entirety, U.S. Provisional Patent Application Ser. No. 61/789,587 titled "Methods, Systems and Compositions for In Vitro Concentric Cell Culture Analog Systems", filed Mar. 15, 2013, an inventor James Hickman; and U.S. Provisional Patent Application Ser. No. 61/790,061 titled "Devices and Systems for Whole Heart Function", filed Mar. 15, 2013, an inventor James Hickman.

A number of embodiments of the invention have been described. Nevertheless, it will be understood that various modifications may be made without departing from the spirit and scope of the invention. Accordingly, other embodiments are within the scope of the following claims.

EXAMPLES

Example 1: System Design

Referring now to FIGS. 1A-1D, pumpless microfluidic systems including one or more modules, components, or chambers are shown. As seen in FIG. 1A, any number of modules can be combined and interconnected. Fluid for the entire system can be added or removed through the fluid access ports, for example when feeding cells or dosing with drugs. Additionally, flow only occurs via exchange between the fluid access ports. Therefore, modules or components with no flow can be made by restricting access to one access port. As seen in FIG. 1B, a single module can be made without flow by removing an access port and co-locating the other inside the module. As seen in FIG. 1C, a single module can be made with flow by adding the second access port. As seen in FIG. 1D, more modules allow more complex arrangements such as this three module network with branching interconnects.

A pumpless microfluidic system can include one or more modules, components, or chambers (e.g., components $m_{11}$, $m_{12}$, ... $m_{ij}$ in FIG. 1A). The pumpless cell culture analog system can include one component, two components, three components, four components, five components, six components, seven components, eight components or more than eight components. A component can include cells that mimic the multicellular architectures of a bodily organ (e.g., heart, liver, kidney, gastrointestinal organ, etc.). It is contemplated that in a plurality of components, each component is different from the other components, for example, different in that each component has one type of cells or has one physiological function. Optionally, each component can include cells that mimic the multicellular architectures of a different bodily organ. For example, a pumpless cell culture analog system can include a plurality of components comprising a cardiac component, a hepatic component, a neural component, a motoneuron component, and a muscle component. This disclosure contemplates that the components can be combined in any desired number and manner to form a cell culture analog system that can mimic or simulate physiological conditions in a living subject such as a human or an animal.

The pumpless microfluidic system can be configured to recirculate a fluid, e.g., a serum free medium as described herein. For example, the fluid can be configured to recirculate through a system including a single component. Alternatively or additionally, the fluid can be configured to recirculate through a plurality of components arranged in fluid connection with one another, e.g., using one or more micro-channels. For example, in FIG. 1A, component $m_{11}$ is in fluid connection with components $m_{12}$, $m_{22}$, ... and $m_{i2}$. It should be understood that this is only one example configuration for the pumpless microfluidic system and that this disclosure contemplates arranging any two or more components in fluid connection. Additionally, fluid can be moved in the pumpless microfluidic system without using any pumps. In other words, the fluid can naturally circulate through the pumpless microfluidic system. Optionally, in some implementations, the pumpless microfluid system can be gravity driven. This disclosure contemplates that the fluid can be circulated by means other than gravity including but not limited to temperature gradients and/or pressure gradients. The pumpless microfluidic system can optionally be one of the μCCAs described herein.

Figure 2A:
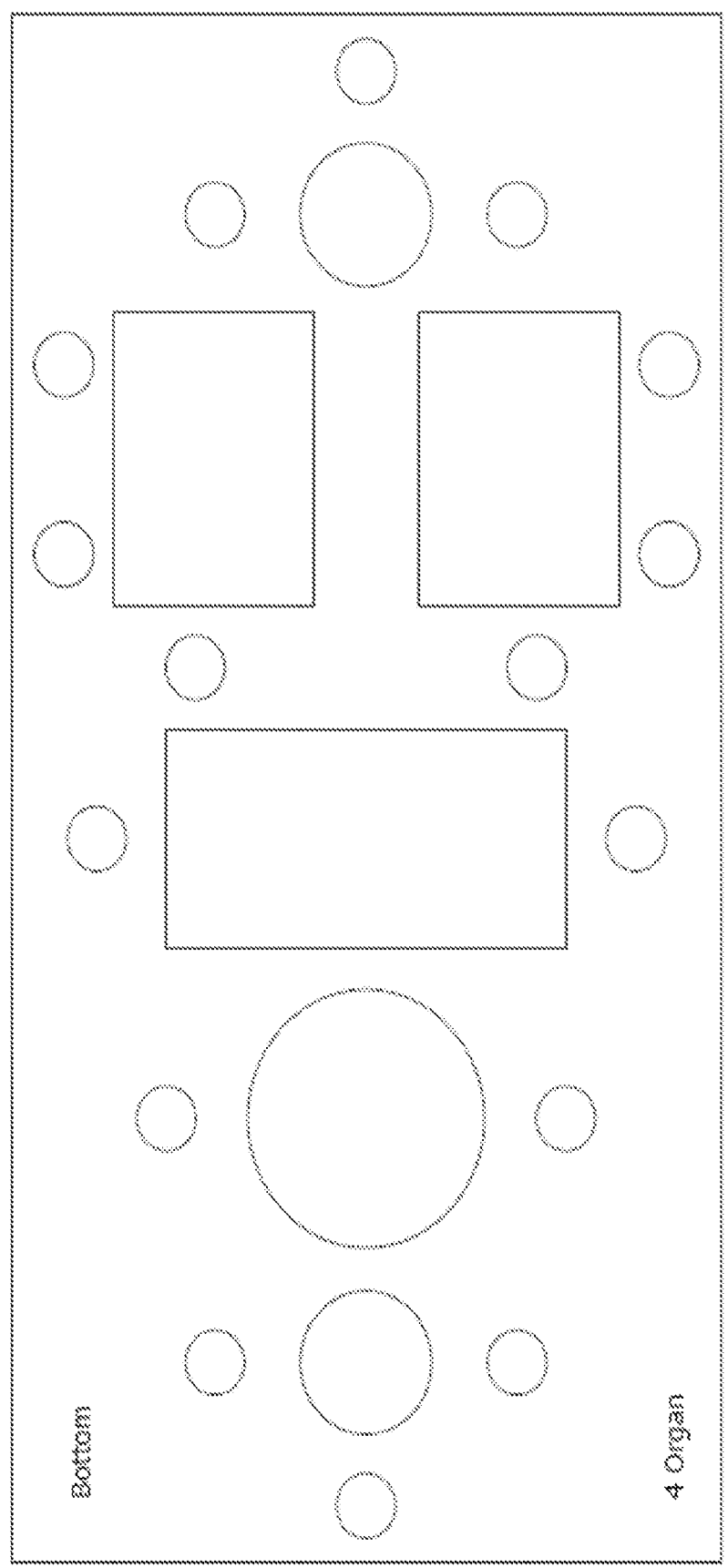
FIGS. 2A and 2B illustrate reconfigurable system gaskets for an example pumpless microfluidic organ-on-a-chip system.
Figure 2B:
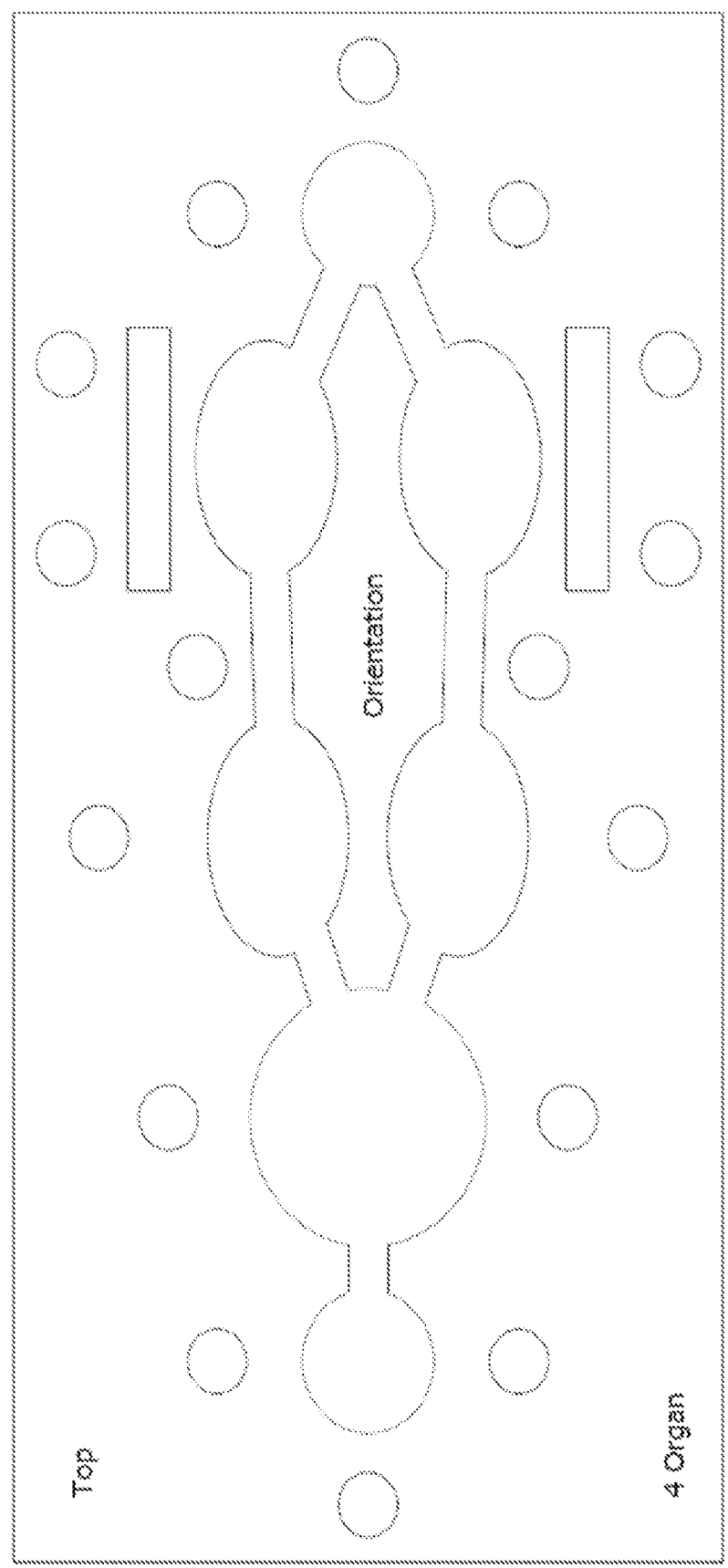
Figure 2C:
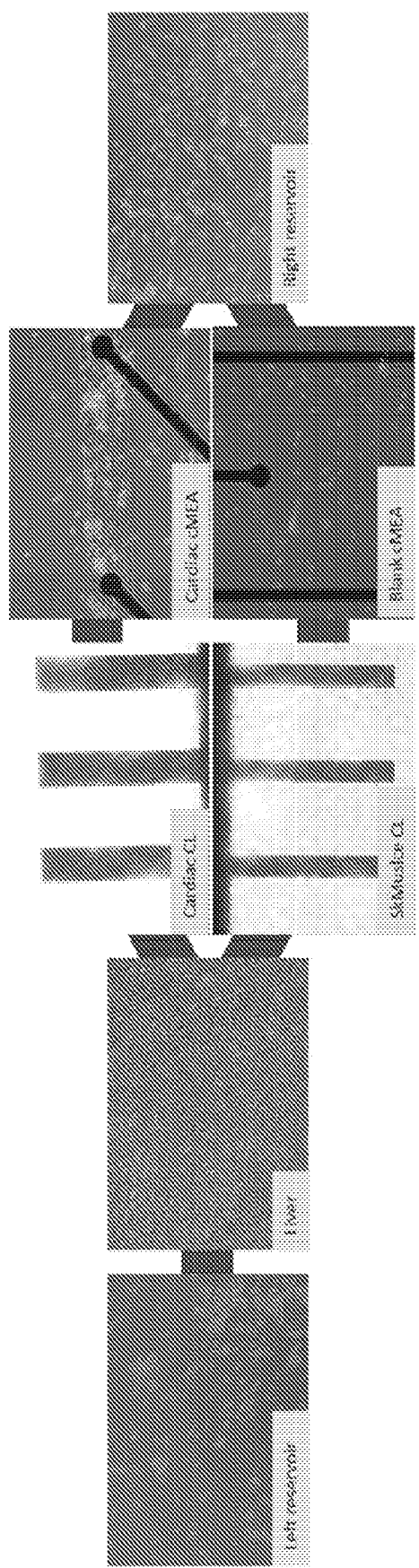
FIG. 2C shows phase images of organs in this system.
Figure 2D:
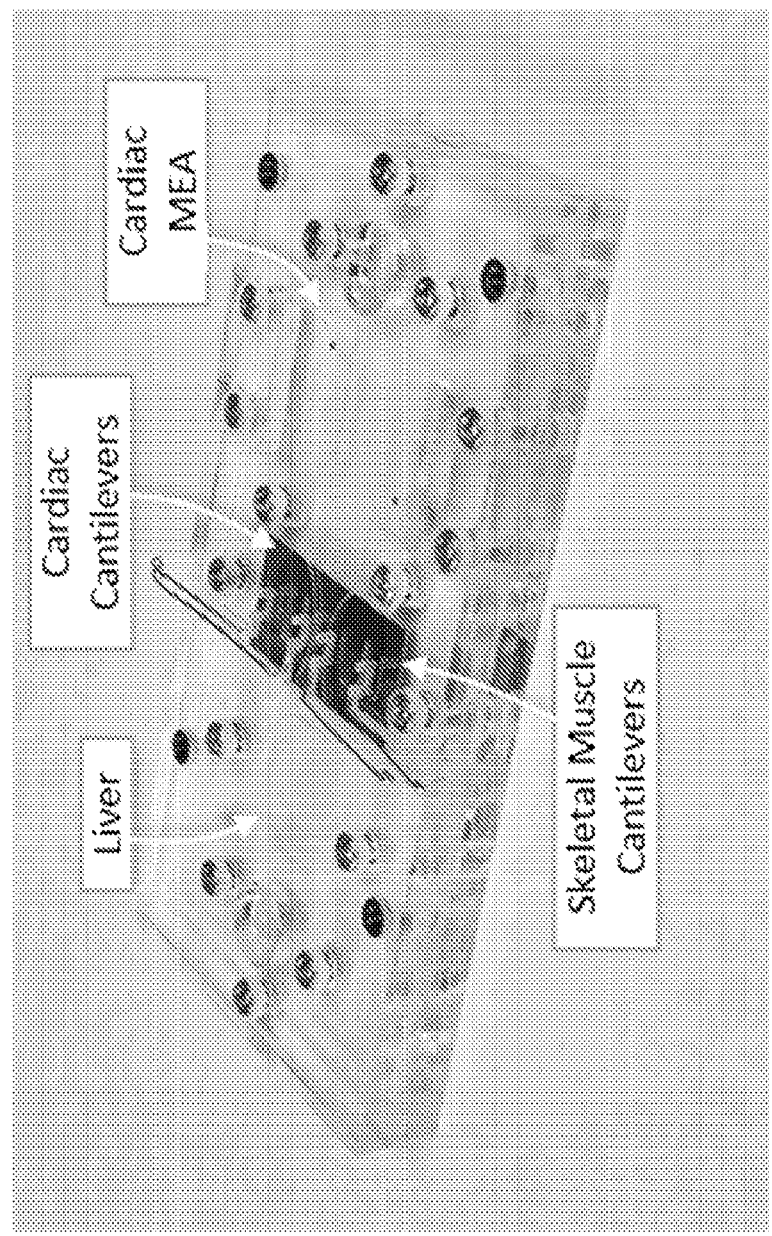
FIG. 2D is a photograph of such a system.
Figure 2E:
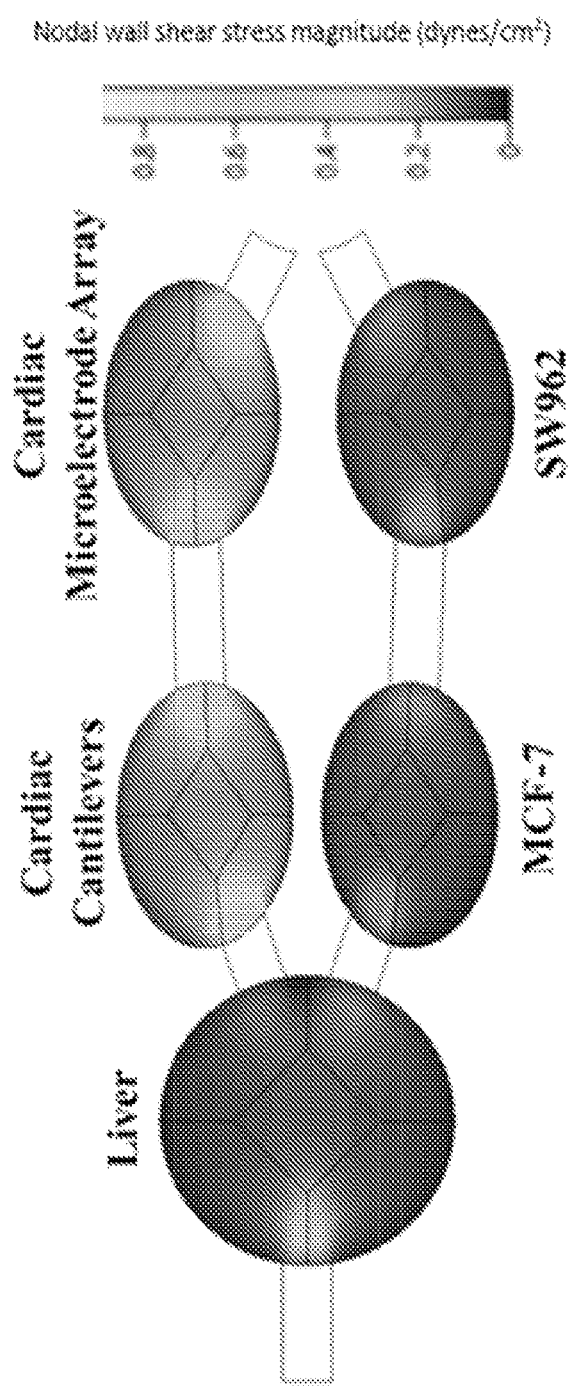
FIG. 2E is a heat map of the shear stress experienced at the system walls in the system shown in FIG. 2D.

FIGS. 2A and 2B illustrate reconfigurable system gaskets for an example pumpless microfluidic organ-on-a-chip system. FIG. 2C shows phase images of organs in this system. FIG. 2D is a photograph of such a system. FIG. 2E is a heat map of the shear stress experienced at the system walls in the system shown in FIG. 2D.

Example 2: Body-On-a-Chip with Immune Cell Component

In this example, a body-on-a-chip system containing an immune cell component in the form of a macrophage cell line was developed. The system is used to investigate the role immunomodulatory molecules play in macrophage activation in the presence of other functional tissues in vitro. The introduction of a recirculating immune system cell type to a body-on-a-chip platform allows this system to monitor more complex cell behavior and cell-cell interactions in response to drug treatment. This device supports the interrogation of complex, integrated immune system responses to tissue-level effects caused by drug compounds as well as by compounds that directly activate macrophages along the classical, pro-inflammatory pathway. This system's engineering parameters, namely its gravity-driven medium recirculation and reconfigurable nature, facilitate the integration and analysis of other of immune tissues in isolation or combination. The bio-MEMS chips facilitate noninvasive testing of functional parameters and the low system volume supports analysis of cytokines and other molecules produced in small amount by tissues in the system. Taken together, this system provides an ideal platform to study innate and adaptive as well as cell-based and humoral immune responses in a self-contained system.

Below, the effects of two different compound treatment programs are described. The first (amiodarone treatment) is aimed at damaging a specifically targeted tissue, and the second (LPS/IFN-γ treatment) is aimed at general immune cell activation to study the differences in the system's function readouts, cytokine production and THP-1 cell activation.

Materials & Methods
System Configuration—3-O and 4-O Systems:

A four-organ system (4-O) was developed to contain a liver compartment, recirculating THP-1 cells, and three separate bioMEMs devices to measure the cardiomyocytes' electrical and mechanical functionality, as well as the mechanical function of the skeletal muscle. Three organ systems (3-0) were also developed to serve as a monocyte-free control for the 4-O systems. These contained the same liver coverslips and bioMEMs devices as the 4-O platform, but did not have the added recirculating THP-1 cells. Cardiac and skeletal muscle mechanical function was evaluated by seeding the cardiomyocytes and skeletal muscle onto their own respective custom arrays of microscale cantilevers. Contractile force of the cardiac and skeletal muscle was calculated from laser-based measurements of cantilever bending resulting from contractile muscle (Stancescu et al 2015). Cardiac electrical function was measured via a microelectrode array amplifier system by incorporating and patterning cardiomyocytes onto custom microelectrode arrays with chemical patterning to produce a defined conduction path along a series of surface embedded microelectrodes (Nataraj an et al 2011, Stancescu et al 2015). Electrical stimulation for skeletal muscle force was generated inside the system with housing-embedded electrodes for cantilevers.

In this configuration, the effects each drug had on cardiac and skeletal muscle function, in addition to the effect of the induced immune response, was evaluated in a single device. The systems were run for a total of 7 days with THP-1 cell addition on day 0, and administration of drugs as a single dose at day 3. Details on the cell culture conditions, material preparation, bioMEMs fabrication and design, and measurements are described in more detail separately.

System Fabrication:

A multi-chamber flow system was designed to allow for the incorporation of multiple organ tissues in a pumpless, recirculating system with integrated measurements for mechanical function of cardiomyocytes and skeletal muscle, and electrical function of cardiomyocytes. The design was adapted from a larger system with chambers to accommodate up to 5 organs without a recirculating immune component (Oleaga, 2016). The footprint of the system was minimized, media volumes were reduced, and capabilities to record in situ functional measurements were added. The design of the flow chambers and microfluidic device was aided by computational fluid dynamics modeling to establish shear stresses near the cell layers within physiological ranges. This system uses a VWR Signature™ rocking platform shaker to produce a defined rocking profile of 1 oscillation per minute at an amplitude of 1°. This rocking action produces recirculating flow in the system, with medium flowing between the two reservoirs through the organ chambers. Housings were fabricated from 6 mm thick clear cast acrylic sheets (McMaster-Carr), and gaskets were made from 0.5 mm thick poly(dimethyl siloxane) (PDMS) elastomer sheet material (Grace BioLabs). Following computational fluid dynamics modeling, two-dimensional drawings were created in Autodesk Inventor to define the laser cutting paths for creating the acrylic housing tops and bottoms as well as the two PDMS gaskets: a bottom gasket for defining the location of each organ chip, and a top gasket to define the fluidic flow paths and fluidic chambers above the chips. Housings and gaskets were laser cut on a Universal Laser Systems Versalaser PLS 75 W laser cutter, with additional post processing performed for counterboring screw holes and inserting brass screw inserts (McMaster-Carr, 93465A107) for improving contact pressure uniformity throughout the system.

Cell Culture
Primary Human Hepatocyte Culture:

Primary human hepatocytes were sourced from Massachusetts General Hospital (MGH) from patient biopsies, and thawed and cultured in specific media on 60 ug/mL rat tail collagen type I coated surfaces according to previously published protocols (Oleaga, 2016).

Cardiomyocyte Culture:

Custom patterned MEA chips and cantilevers were coated with human plasma fibronectin (Millipore) diluted in 1× phosphate buffered saline (PBS) (Thermo Scientific) to concentrations of 10 ug/mL for cMEAs and 50 ug/mL for cantilevers, then incubated at 37° C. for 30 minutes. cMEAs were then washed once and cantilevers washed three times with 1×PBS. IPSC derived cardiomyocytes (Cellular Dynamics) were thawed and seeded directly onto the surfaces according to Oleaga et al at 50,000 cells per cMEA and 500,000 cells per cantilever (Oleaga, 2016).

Skeletal Muscle Culture:

Human skeletal muscle myoblast, or satellite cells, were isolated using a needle biopsy of adult muscle and were purchased commercially from Lonza (Lonza, Allendale, N.J., USA). Cells were expanded through one passaging and cryopreserved. These cells were seeded at 500 cells/mm$^2$ on patterned cantilever chips and grown to confluency (24-48 hours) in a custom serum-free myoblast proliferation medium (McAleer, Rumsey et al. 2015). At confluency, this medium was replaced with a commercial neuronal base medium, NBActiv4 (Brain Bits LLC, Springfield, Ill., USA) to induce myoblast fusion. The cultures were maintained in NBActiv4 for 11 days before being assembled in the 3-O and 4-O systems.

THP-1 Cell Culture:

THP-1 monocytes (ATCC, TIB-202) were cultured in T-75 flasks according to the protocol recommended by ATCC. Cell culture density was maintained in the density range that was found to be optimal for logarithmic growth (350,000-500,000 cells/mL). THP-1 cells show a proclivity towards forming large aggregates of loosely joined cells. These clumps were broken down back into single cells through the addition of deoxyribonuclease 1 (DNase 1, dissolved in 0.85% NaCl in water) (Sigma-Aldrich, D4513)

at a concentration of 0.1 mg/mL. When cells had reached their optimal density, they were harvested and pelleted via centrifugation at 150×g for 5 min, resuspended in multi-organ system medium (MOSM) and added to the systems at a physiologically relevant concentration of 250,000 cells/mL. THP-1 cell adhesion to the inside surfaces of the housings was minimized by passivating the inside surfaces with bovine serum albumin (BSA, 0.5 mg/mL dissolved in PBS). 10 uL of medium was removed from each system daily to determine the number of freely recirculating cells present. Initial THP-1 culture medium consisted of RPMI 1640 base medium (ThermoFisher, 11875135) with 10% fetal bovine serum (ThermoFisher, 16000044) and 1× GlutaMAX (ThermoFisher, 35050061).

Phase Contrast Cell Imaging:

Hepatocyte, cardiomyocyte, myocyte, and THP-1 cell morphology was studied via phase microscopy on days 3, 5, and 7 after assembly using an inverted phase contrast microscope (Nikon, Eclipse TS100). Images were collected with a stand-alone microscope camera controller (Nikon, DS-L3).

Custom Patterned Microelectrode Array (cMEA) and Cantilever Preparation:

Cantilever array chips for force measurements were fabricated following protocols previously described (McAleer, 2014; Pirozzi, 2013; Smith, 2014; Smith, 2014; Stancescu, 2015; Wilson, 2010). Briefly, cantilever chips containing cantilevers 4 μm thick, 100 μm wide, and 737 μm long were fabricated from silicon-on-insulator wafers with a 4 μm device layer and 1 μm buried oxide. The cantilever devices were created in the device layer and a window underneath the cantilevers were produced using standard photolithographic patterning techniques and deep reactive ion etching (DRIE).

Custom patterned microelectrode array chips were custom designed with ten 200 μm diameter recording/stimulating electrodes and one 2000 μm diameter ground electrode, and fabricated with standard microfabrication procedures. The wires and electrodes were composed of electron beam evaporated 10 nm titanium and 50 nm platinum and deposited on a fused silica substrate and patterned via a liftoff process. The titanium/platinum wires were insulated with a three-layer stack of 150 nm layers of silicon oxide, silicon nitride, and silicon oxide produced via PECVD and etched using reactive ion etching (RIE) with gas mixtures of $CHF_3$ and $O_2$.

After fabrication, the surfaces of the cantilever chips and microelectrode array chips were surface modified using silane chemistry. The surfaces of the cantilever chips were modified with 3-(Trimethoxysilyl)propyl)diethylenetriamine silane (DETA) in toluene followed by adsorption of fibronectin to the surface to produce an amine-containing surface. The surfaces of the microelectrode array chips were surface patterned with a combination of poly(ethylene glycol) (PEG)-containing silane and fibronectin. In this method, the surfaces were modified with 2-[Methoxypoly(ethyleneoxy)propyl]trimethoxysilane, a PEG-containing silane in distilled toluene to produce a cytophobic surface. This layer was patterned using a 193 nm ArF excimer laser (Lambda Physik, Santa Clara, Calif.) through a quartz photomask to remove areas of the PEG chemistry, and allowing the deposition of fibronectin as described in the cell culture procedures.

Immunocytochemistry:

At the end of each experiment, cardiac cMEAs and hepatocyte coverslips were fixed with 4% paraformaldehyde in 1×PBS for 5 minutes. Cells were rinsed twice with 1×PBS and Cells were permeabilized with a solution of 0.1% Triton X-100 in 1×PBS for 15 minutes then blocked with 5% donkey serum in 1×PBS for 20 minutes. Cells were then incubated overnight at 4° C. with primary antibody in blocking solution. Primary antibodies used were anti-CD14, anti-CD16, anti-CD69, anti-CD11b, anti-CD86, and anti-CCR5. Following three, five-minute washes with 1×PBS, cells were incubated for 2 hours at room temperature in the dark with a secondary antibody conjugated to Alexa-488 fluorophore, or Alexa-568 fluorophore. Following the secondary antibody incubation, surfaces were washed 3× in PBS and incubated with 3 mM 4'-6-Diamidino-2-Phenylindole (DAPI) in 1×PBS for 10 min, in the dark and at RT for nuclei staining. DAPI solution was removed and the cells were washed 3× with PBS. Finally, coverslips were mounted on glass slides using a Hard Set Mounting with DAPI (Vector laboratories, Inc.). Alternatively, MEAs were left in the final 1×PBS rinse and imaged using a water immersion lens.

Nonadherent THP-1 cells were fixed by adding 4% formaldehyde in 1×PBS to the culture media and incubating at room temperature for 20 minutes. Cells were pelleted, rinsed once with DI water, and resuspended in 200 uL of DI water. 5 uL of the cell suspension was transferred to the center of a collagen-coated coverslip and gently smeared using a micropipette tip bent at 90°. Cells were allowed to dry at room temperature for 12 hours, then stored at 4° until imaging.

Fluorescence images were collected using 10× or 40× objectives and 10× magnification of an Axioskop 2 mot plus upright spinning disk confocal microscope (Carl Zeiss), connected to XCite 120 Fluorescence Illumination system (EXFO) beam, a multi-spectral laser scanning and Volocity software (Perkin Elmer).

Cell Tracker Studies:

THP-1 cells were collected in a 15 mL conical tube and centrifuged to a pellet at 300 g for 5 minutes. The cells were resuspended and counted and the volume adjusted to $1 \times 10^6$ cells/mL. Then cells were then incubated with Cell Tracker Red CMTPX Dye (ThermoFisher C34552) following the manufacturer's protocol. The dye loaded cells were then used for infiltration studies in 4-O systems as described.

Cytochrome p450 1A1 and 3A4 Enzymatic Activities:

Cytochrome p450 1A1 and 3A4 isoforms from the hepatic cultures were assessed with a luciferin based method in two reactions. Basal activities were compared to induced activities upon incubations with 10 nM TCDD (Sigma, 48599) and 20 μM Rifampicin (Sigma, R3501) for 48 h, prior to the analysis. At 7, 14, 21 and 28 DIV, cells were rinsed 3 times with 1×PBS and incubated with 1A1 specific substrate, Luciferin-CEE (120 μM) (Promega, V8752) in phenol red-free 1×DMEM (Thermo Fisher Scientific, A1443001) for 3 h at 37° C. The enzymatic product (D-Luciferin) of the first reaction was collected and stored at −80° C. until further analysis. After one rinse with 1×PBS, surfaces were incubated with 3A4 specific substrate, Luciferin-IPA (12 μM) (Promega, V9002) for 1 hour at 37° C. The enzymatic products (D-Luciferin ester) of the first reaction were collected as previously described. At this point cells were either returned to culture or fixed for immunostaining. The luciferin detection reaction was performed by mixing 50 μL of the collected samples, D-Luciferin standard curve or pro-luciferins (CEE or IPA) (negative controls) with 50 μL of the Luciferin Detection Reagent (LDR) in a white opaque 96-well plate (Cellstar, 655083). Twenty minutes after incubation at room temperature in the dark, luminescence was measured using a Synergy HT plate reader with KC4 software. The instrument was set to measure each sample 10 times with a starting delay of 250 msec between samples and 1 msec delay in the same sample. The software was programmed to adjust sensitivity to the strongest signal well, and scaled subsequently to obtain relative light units (RLU). 3A4 samples were measured separately from 1A1 samples due to high differences in luminescence emission. Similarly, induced and uninduced samples were measured separately. Each plate was measured a minimum of 5 times to ensure the photomultiplier detector was stabilized, and the average of all readings was taken for the final RLU values. A regression line with the standards (0.5-500 nM diluted in 1×DMEM), subtracting intrinsic DMEM luminescence from values, was obtained for each analysis. D-luciferin concentration (nM) was obtained for samples (minus the intrinsic pro-luciferin luminescence value) by clearing the equation. Enzymatic activities were finally represented as D-Luciferin picomoles produced in one hour by $1 \times 10^6$ cells. The induced activity is plotted as absolute activity (pmol D-Luc/h/$10^6$ cells), as well as, fold-change compared to the basal activity. Because not all the induced values were paired with the basal values, we calculated the standard error using an approximate formula from Fieller's theorem;

$$\sqrt{\{(ib)2([SEi2i2]+[SEb2b2])\}} \qquad 1.$$

Where b is mean of basal activity, i is mean of induced activity, SEb is ±standard error from basal activity values and SEi is ±standard error from induced activity values.

Drug Treatment:

Drug addition to the 3-O and 4-O systems was performed on D3 post-assembly. On the day of addition, 3× concentrations of each drug in the serum-free, multi-organ system medium (MOSM) were prepared in advance. ⅓ of the media in each system was removed and replaced with an equal volume of the concentrated drug solution. This facilitated for rapid mixing and complete diffusion of the drugs in the systems without requiring a full media change. Amiodarone hydrochloride (Sigma-Aldrich, A8423,) was dissolved in DMSO at a stock concentration of 40 mM and administered at a final dose of 50 uM. Lipopolysaccharide (LPS, Sigma-Aldrich, L2630) was dissolved in PBS 1× at a concentration of 1 µg/mL and interferon-γ (IFN-γ) (Sigma-Aldrich, 11040596001) was dissolved in DI water at a concentration of 100,000 units/mL. LPS and IFN-γ were administered as a single cocktail at final concentrations of 10 ng/mL and 100 units/mL, respectively.

HPLC and MS:

Medium samples collected from the systems were spiked with a tamoxifen internal standard (10 nM final measured concentration) and combined with acetonitrile at a 1:3 ratio to extract proteins. The mixtures were then centrifuged at 100×G for 5 minutes and supernatants were collected and diluted 1 to 51 in the initial mobile phase. A gradient elution method was run over 5.5 minutes beginning at a ratio of 60:40 and ending at 5:95 of 0.1% formic acid in water:0.1% formic acid in acetonitrile through a 4.6 mm ID×100 mm, 3.5 micron Agilent Zorbax C18 column installed in a 1260 Infinity Agilent LC system with a 6490 triple quadrupole MS detector. Monitored amiodarone transitions were 646.03→58.2 with a 48 eV collision energy for the quantification ion and 646.03→100.2 with a 36 eV collision energy for the qualification ion. Quantification and qualification ions for tamoxifen were 372.2→72.1 (28 eV CE) and 372.2→44 (48 eV), respectively. A calibration curve for amiodarone was prepared using standards ranging from 0.5 nM to 500 nM. Regression lines were linear with a 1/x weighting applied.

Cardiac and Skeletal Muscle Force Measurements:

Cardiac and skeletal muscle contractions were measured using a cantilever deflection system that has been described previously (McAleer, 2014; Oleaga, 2016; Oleaga, 2017; Pirozzi, 2013). In summary, a Helium Neon laser beam was directed from the bottom to the tip of each cantilever, and reflected onto a 2D Lateral Effect Position Sensor (Thorlabs, Newton, N.J.). Longitudinal deflection of the cantilever due to muscle contractions results in changes in position of the reflected beam on the lateral effect sensor. Contraction strength was analyzed via a manually-directed peak detection program written in Python 2.7 that measures and computes the average maximum peak amplitude and contraction frequency for each cantilever recording. The voltage output from the position sensor was converted directly to force using a modified form of Stoney's equation.

Cardiac Electrical Activity Measurements:

Custom patterned multielectrode arrays (cMEAs) were fabricated to simultaneously stimulate and record electrical activity of cardiomyocytes cultured on the surface (100 µm diameter electrodes, 1000 µm between electrodes). Before culturing, the surfaces were modified to promote cell adhesion in an unbroken "U" pattern that connected multiple electrodes, allowing conduction velocity of the cells to be recorded at different points (14 mm total path length). Patterned cMEAs were introduced to the housings during system assembly on day 0 of the experiment.

Printed circuit boards (PCBs) and flexible elastomeric connectors (zebra connectors, FUJIPOLY, 1 mm wide×18.2 mm long×9 mm tall) were incorporated into each system to create an interface between the cMEA and a commercially available 60 electrode amplifier (MEA1060, Multichannelsystems). This amplifier was used to both record spontaneous and stimulated electrical activity of the cardiomyocytes. A stimulus generator (STG 1002, Multichannel Systems) was used to stimulate the cells (800 mV rectangular pulse, 0.5 Hz to 3.0 Hz in 0.25 Hz increments). The multichannel systems software suite was used to control both the amplifier and stimulator, and was used to record action potentials.

Drug additions were performed on day 3 of the experiment, immediately after baseline recordings of spontaneous and stimulated cell activity were taken. Cell activity was recorded again 48 and 96 hours after drug exposure. Conduction velocity (CV), spontaneous beat frequency and minimum interspike interval (MIST) were extracted from the data using Clampfit (Axon Instruments).

Spontaneous beat frequency was obtained from spontaneous recordings of cardiac activity 20 seconds in length. For each recording, the frequency was calculated as the number of measured action potentials divided by the length of time between the first and last action potential during the recording interval. The number of action potentials used in the calculation was decreased by 1 to account for the distances between beats $$BF\ (Hz) = (\text{\# of peaks in interval} - 1)/\text{time between first and last peaks (s)}$$

Conduction velocity was measured by determining the length of time for an action potential to travel from an electrically stimulated electrode along the patterned cardiomyocyte path to various electrodes at specific distances along the path, following the method described in Stancescu et al [26]. Stimulation of cardiomyocytes on a single electrode along with the pattern of cardiomyocytes allowed for a defined conduction path of aligned cardiomyocytes. From the recording of stimulated conduction, the conduction velocity was determined by averaging several measurements of the length of time for the action potential to travel along the defined path between two defined electrodes and dividing the physical distance between those two electrodes by that average propagation time.

CV (m/s)=distance between electrodes (m)/average signal propagation time (s)

Urea and Albumin Quantification:

Human serum albumin (HSA) and urea production was quantified by following a previously described protocol (Oleaga, 2016). Briefly, aliquots of media drawn from the systems on days 1, 3, 5, and 7 were stored frozen at −20° C. These were run through commercially available ELISA kits to detect HSA (Bethyl Laboratories Inc, Cat #: E101) and urea (QuantiChrom™ Urea Assay Kit) (BioAssay Systems, Cat #: DIUR-500). Data was processed and graphed using Microsoft Excel.

Viability:

Cell viability was evaluated in one of three ways depending on the surface the cells were grown on. Hepatocytes plated on coverslips were removed from the systems on the day of disassembly and their viability was determined via a standard MTT assay. Briefly, MTT powder was dissolved in a common growth medium to final concentration 5 mg/ml. Cells were incubated in 500 µL of the solution for 90 minutes at 37° C., 5% CO2. The medium was removed and resultant crystals were dissolved in a lysis buffer consisting of 10% SDS with 0.5% acetic acid in dimethyl sulfoxide (DMSO). 100 µL of the solution was placed into a 96 well plate and absorbance read at 570 nm using a BioTek Synergy HT plate reader. The viability of cardiac and skeletal muscle cells plated on BioMEMs devices was assessed using an alamar blue solution (Thermofisher, DAL1025). Surfaces were incubated in 500 µL of a 10% solution (v:v) of alamar blue in growth medium at 37° C., 5% $CO_2$ for 24 hours. 100 µL of the solution was placed into a 96 well plate and read at fluorescence excitation wavelength 570 nm and emission at 590 nm using the BioTeK Synergy HT plate reader.

Statistical Methods:

Values are expressed as the mean±SE of a minimum of three independent experiments. Data was evaluated with unpaired Student's t-Test when analyzing the overall change between two conditions, 2D and 3D, serum-containing and serum-free, or drug treatment and control. Student's t-Test analysis was run with a two-tail distribution and homo- or heteroscedastic variances. A one-way ANOVA test was used to study changes upon one parameter (time). Both analyses were run with Microsoft Excel Statistical tool, and differences with p-values<0.05

Results

Key:
- 3-O System=Cardiac CL, cardiac cMEA, SkM CL, liver coverslip
- 4-O System=Cardiac CL, cardiac cMEA, SkM CL, liver coverslip, THP-1 cells ("4-O" is used interchangeably with "3-0+THP")
- 4-O+Amiod=4-O system with added 50 uM amiodarone
- 4-O+LPS/IFN-γ=4-O system with added LPS/IFN-γ

System Design & Modeling:

A five-compartment microfluidic device used in this example is shown in FIG. 2D. This system was designed to be reconfigurable, meaning that different organ modules can be substituted in and out of the device, depending on the project at hand. The flow of media through the system is gravity-driven, generated through the use of a sinusoidal rocking platform. Computational fluid dynamics modeling was used to define which parameters needed to be altered to effectively model physiological flow in the system, while maintaining an optimal amount of fluid mixing. These flow parameters include tilt angle, oscillation rate, dimensions of the channels and chambers, and permissible levels of shear stress. Issues such as bubble formation and adhesion of cells to the surfaces of the system were minimized through BSA passivation of the systems prior to their assembly. FIG. 2E shows a heat map of the wall shear stress experienced during the flow of fluid through the system.

Figure 3B:
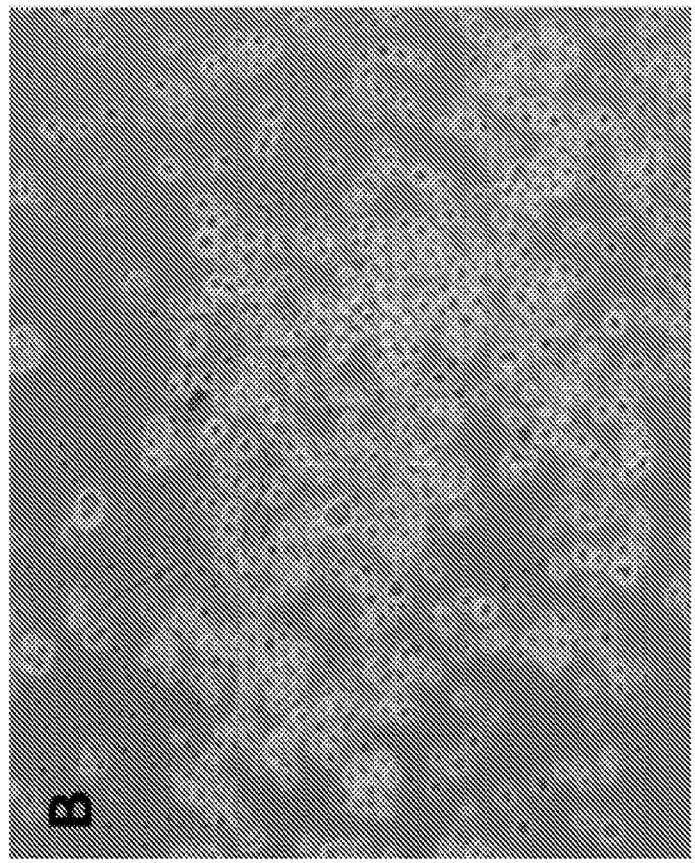
FIGS. 3A-3F depict various results of experiments performed with THP-1 cells.
Figure 3A:
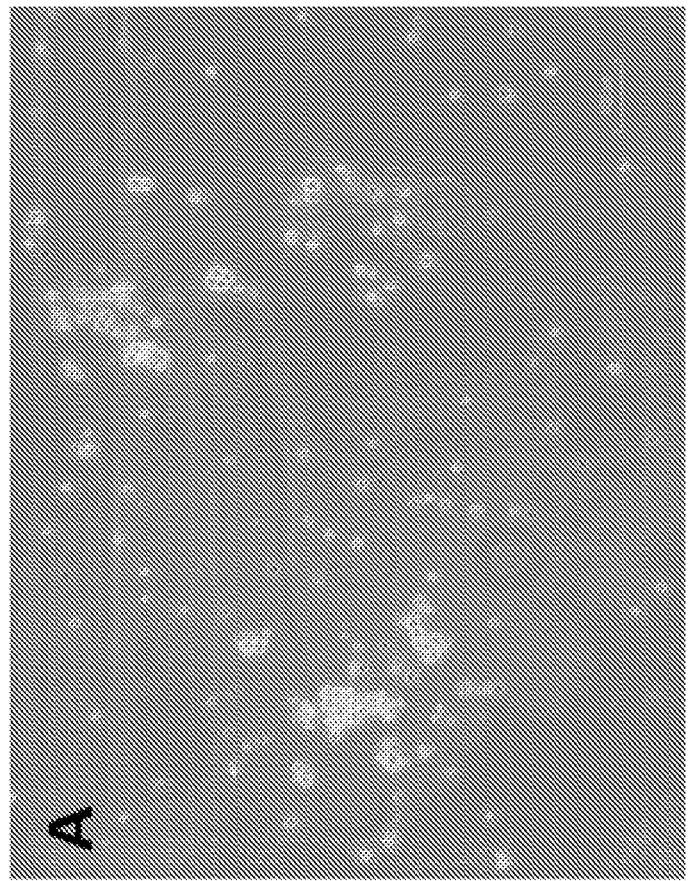
Figure 3C:
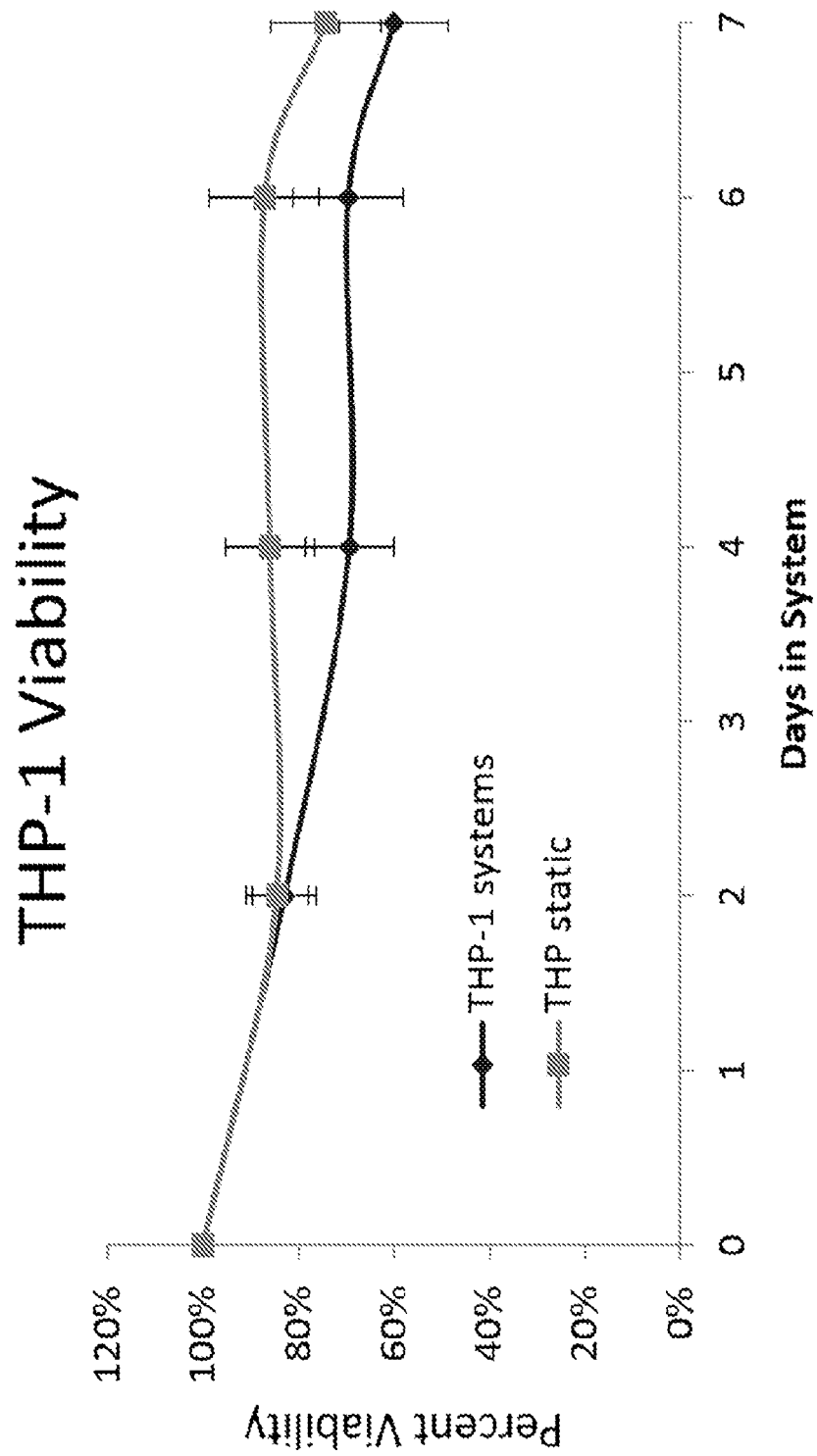
Figure 3D:
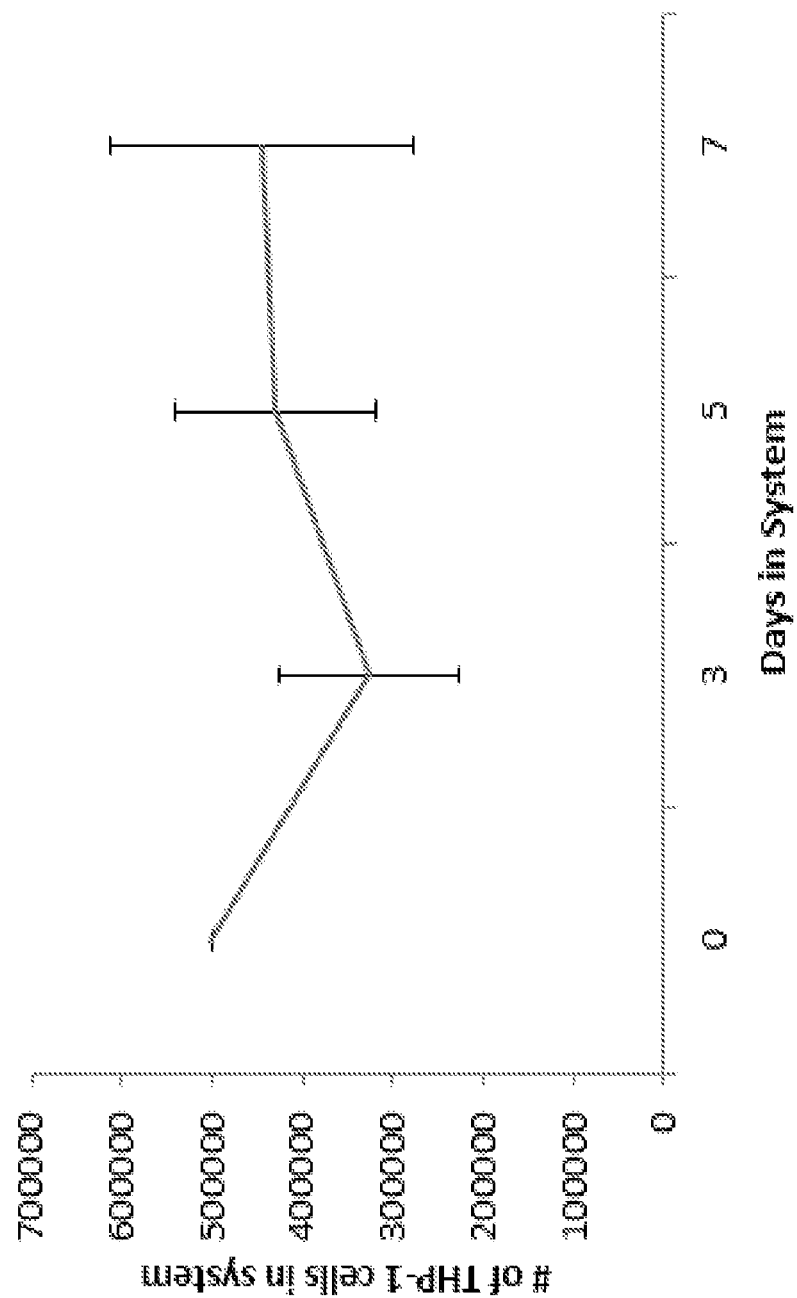

Characterization of the 4-Organ Immune Body-On-A-Chip System:

THP-1 cells, a macrophage cell line, were selected as the immune cell component due to their physiological properties, being critically involved in immunomodulation, pathogen clearance, wound repair and tissue remodeling after injury. FIGS. 3A and 3B are phase contrast images showing these cells in culture. THP-1 cells exhibited many desirable characteristics in the system. For example, they displayed prolonged viability in the housings, up to 7 days in the systems post-addition (FIG. 3C). THP-1 cells also maintained their ability to proliferate, allowing concentrations of recirculating cells to stay constant even though 30% media changes were conducted daily (FIG. 3D). The THP-1 cells were introduced to the systems immediately after assembly on day 0. Due to their non-adherent properties, coupled with the BSA passivation step, THP-1 cells could be observed recirculating freely for the duration of the experiments in control systems. 7).

Figure 3E:
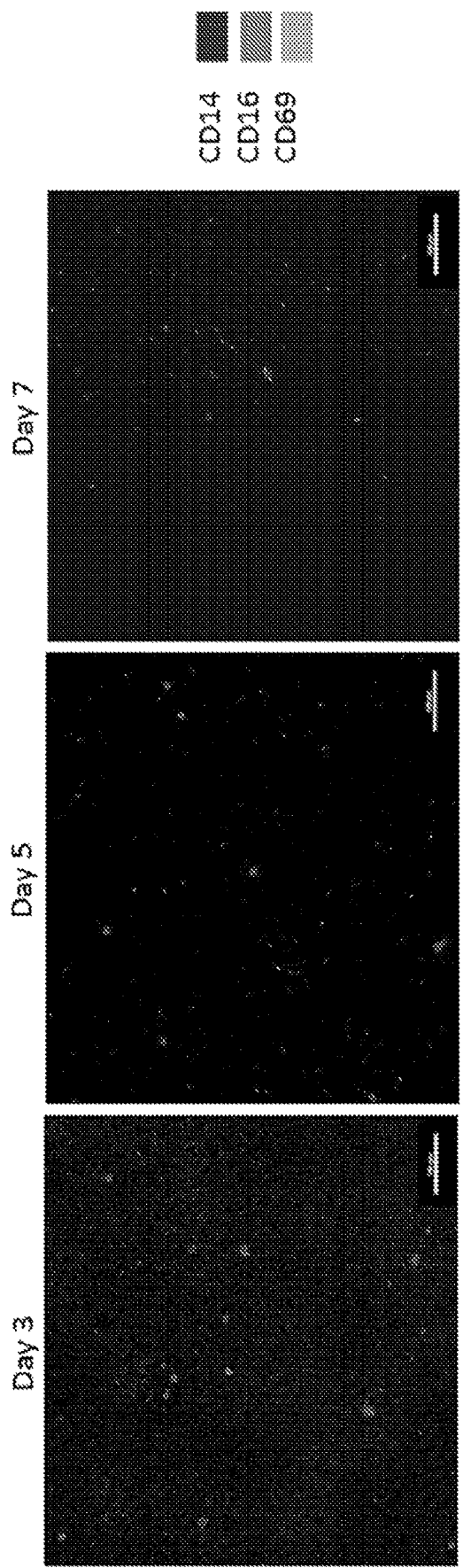
Figure 3F:
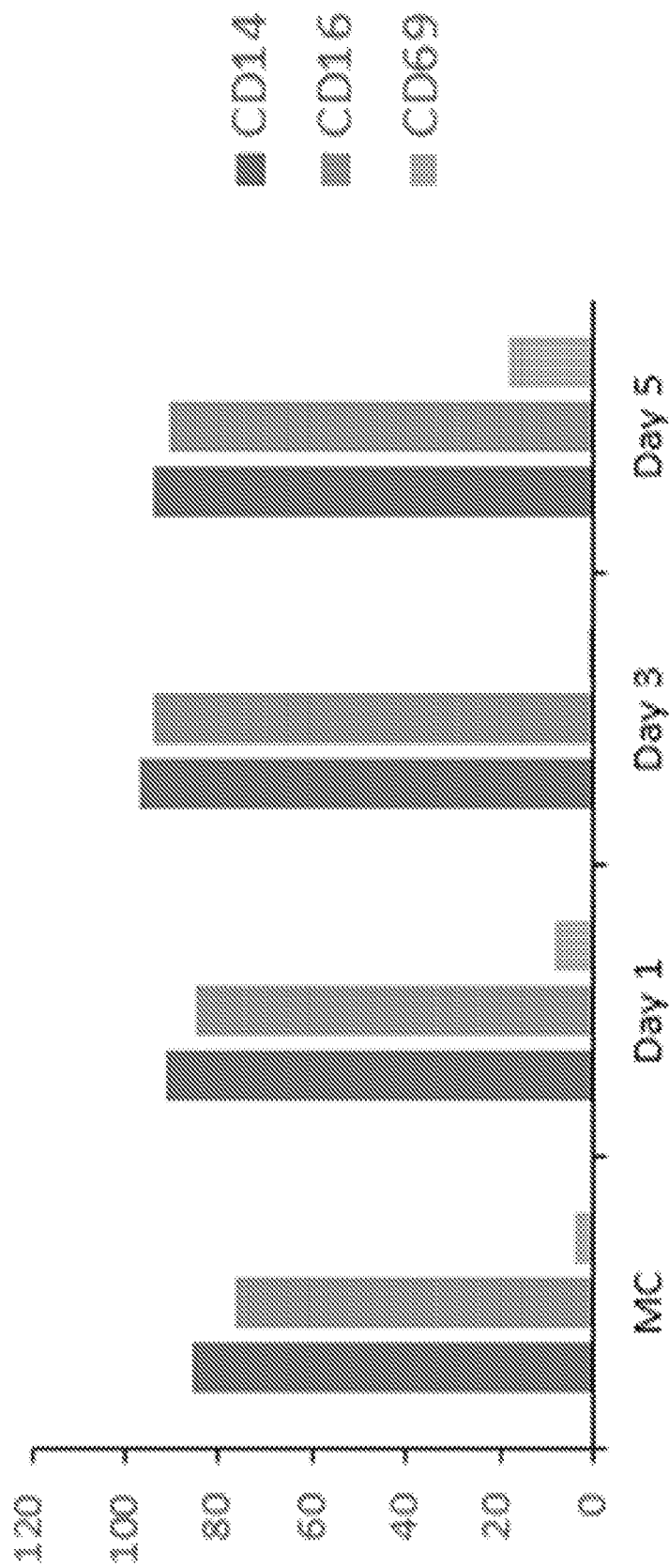

THP-1 cell basal activation levels were evaluated by immunocytochemistry on D3-D7 and flow cytometry on D0-D7 to confirm that THP-1 cells do not activate due recirculation in the housings, or any other intrinsic quality of the system. CD14 and CD16 are general markers for monocytes/macrophages, and CD69 is a general activation marker that is expressed by activated lymphocytes and monocytes. ICC data indicates that activation was low in THP-1 cells removed from the housings, as they were consistently positive for CD14 and CD16, while not expressing CD69 (FIG. 3E). Further phenotypic analysis of THP-1 cells removed from the systems by flow cytometry revealed that they maintain high expression levels of CD14 and CD16 from D0-D5, and 0-10% of these THP-1 cells were found to be CD69 positive from D0 to D3, with an increase to 20% on D5. (FIG. 3F).

Functional datasets for cardiac and skeletal muscle physiology as well as biomarker data for liver physiology were collected and analyzed to set a baseline for comparison to future experiments.

Figure 4A:
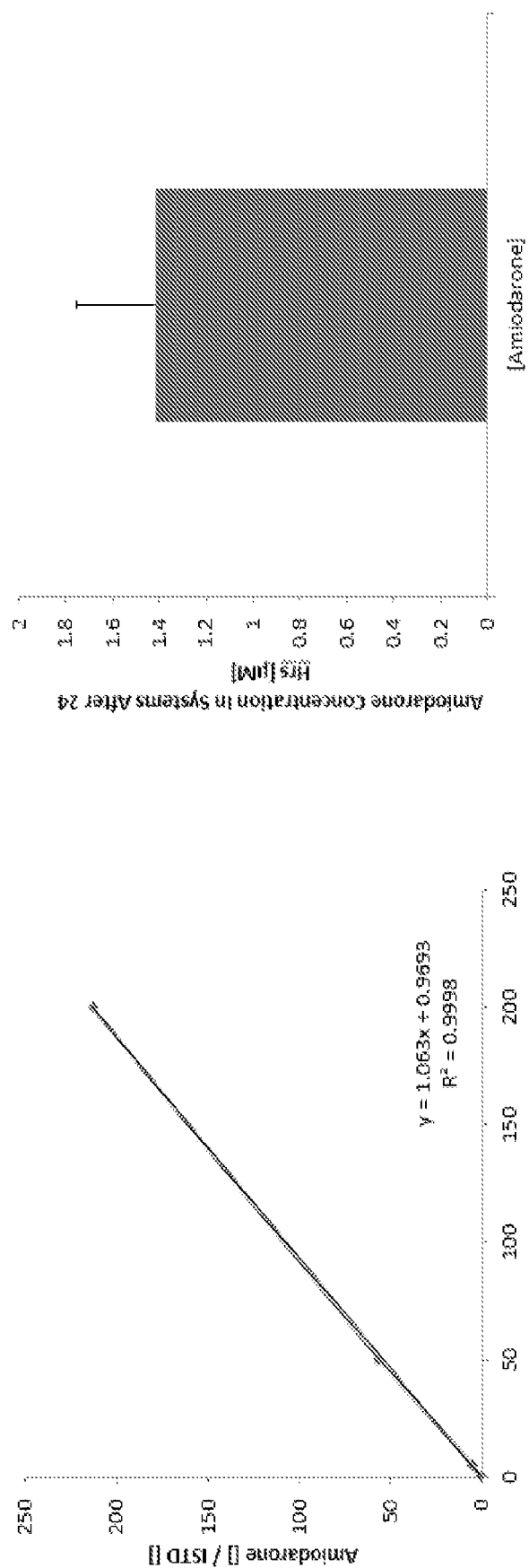
FIGS. 4A-4F show effects of amiodarone on organs in an example pumpless microfluidic organ-on-a-chip system.

Site-Directed Immune Response:

In these experiments, the objective was to introduce a test compound that would induce toxicity and tissue damage in one of the organs present in the 4-O system and determine the level of monocyte activation and infiltration that occurred as a result. Amiodarone was chosen for these purposes because it is known to have cardiotoxic effects. Medium samples were drawn from the systems 24 hours post-dose and analyzed by HPLC to determine the amount of amiodarone still present in the systems. A reduction of 97% (50 µM to 1.41 µM mean concentration) was observed, indicating that nearly all the drug was metabolized by the liver or ad/absorbed after one day (FIG. 4A).

Figure 4B:
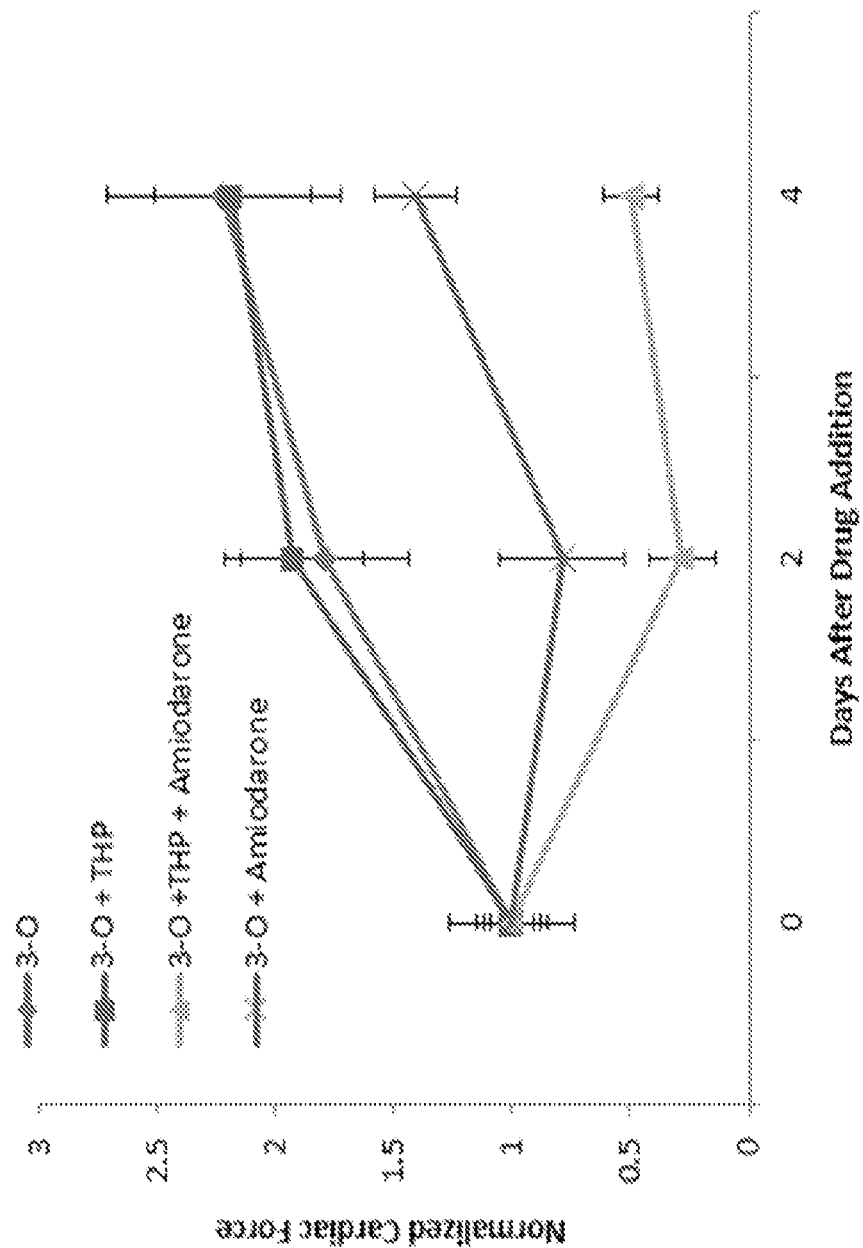
Figure 4C:
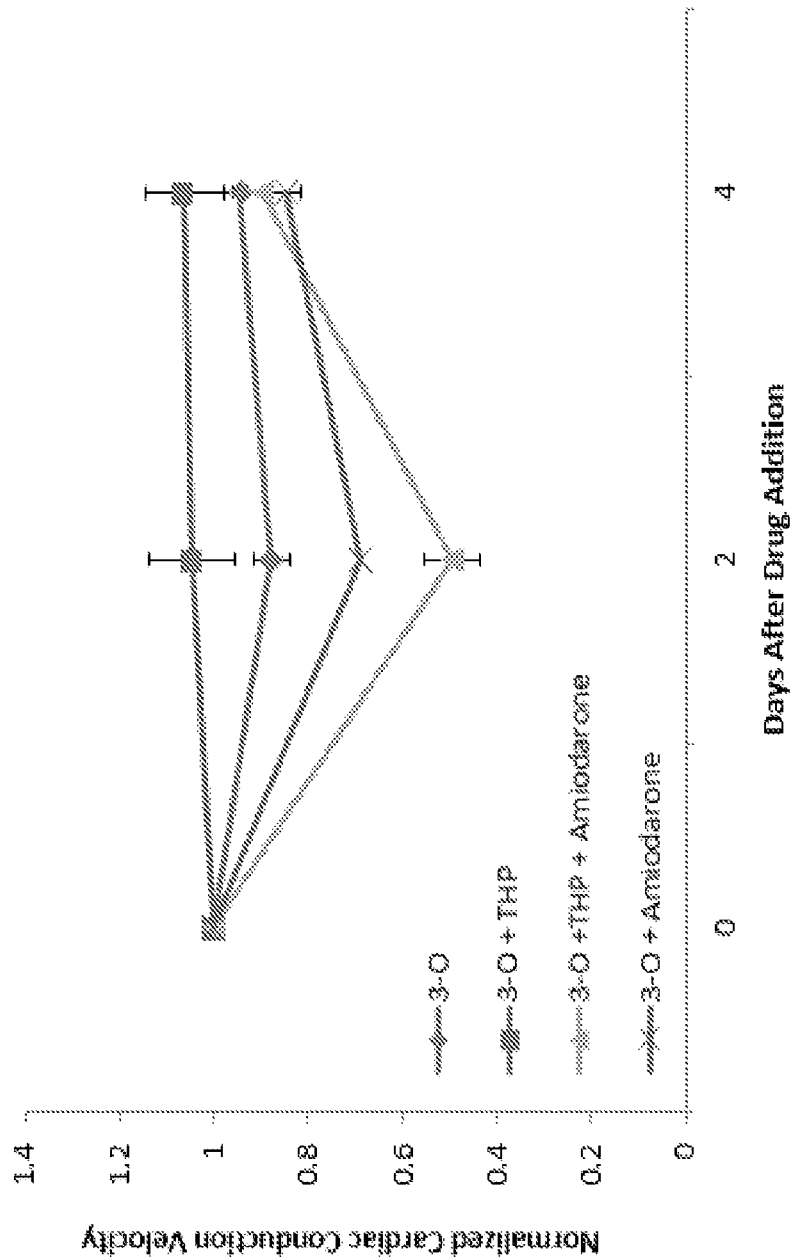
Figure 4D:
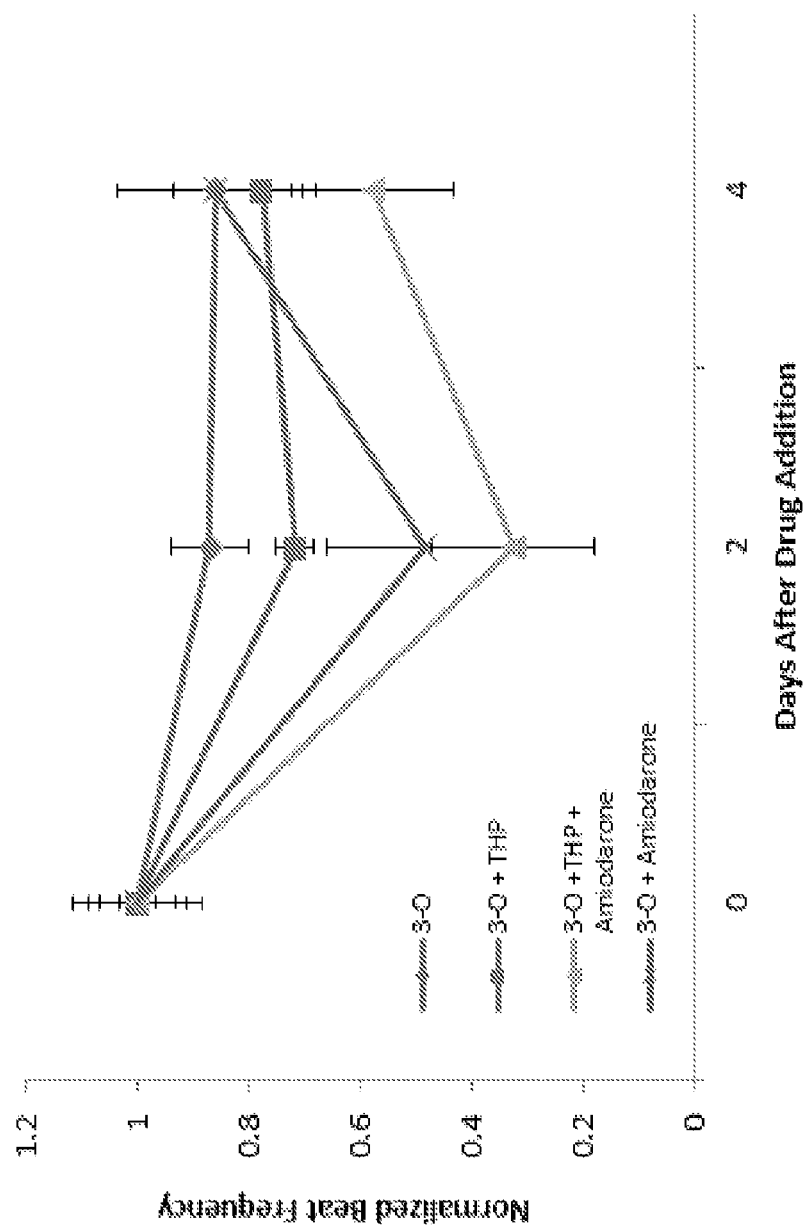
Figure 4E:
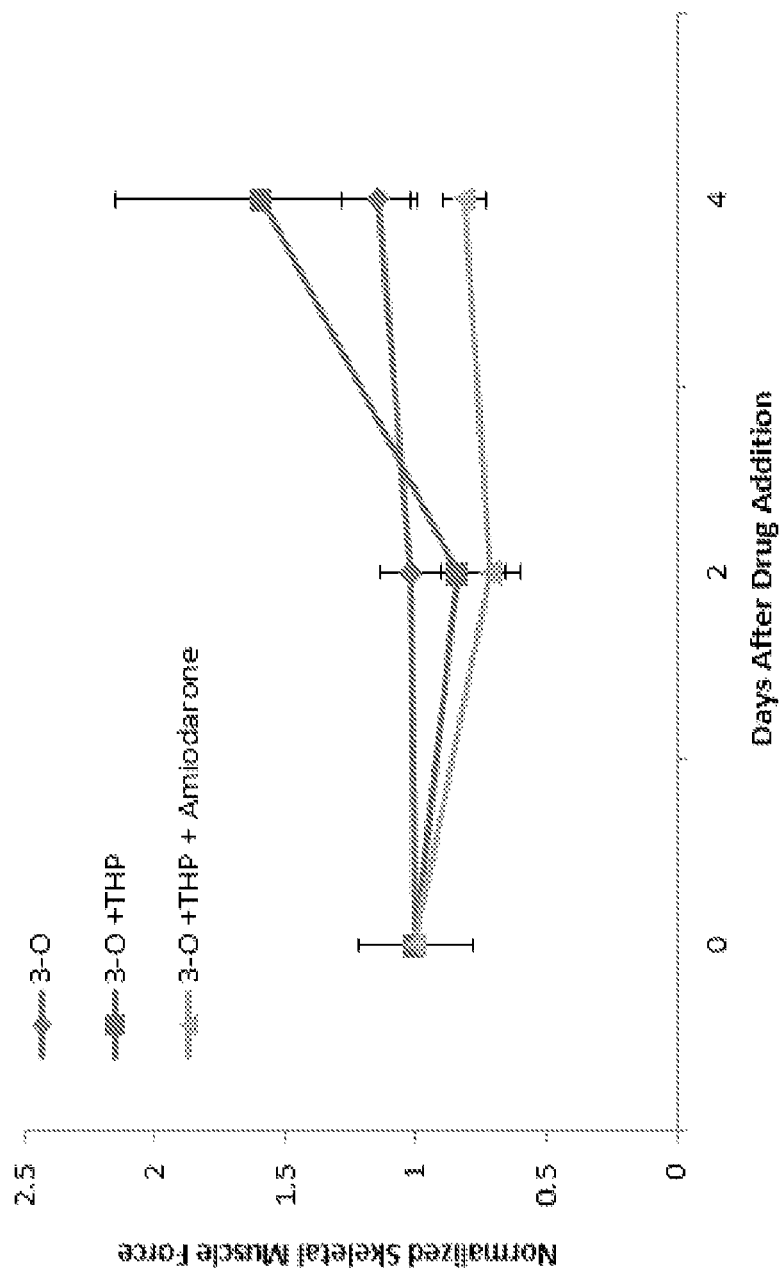
Figure 4F:
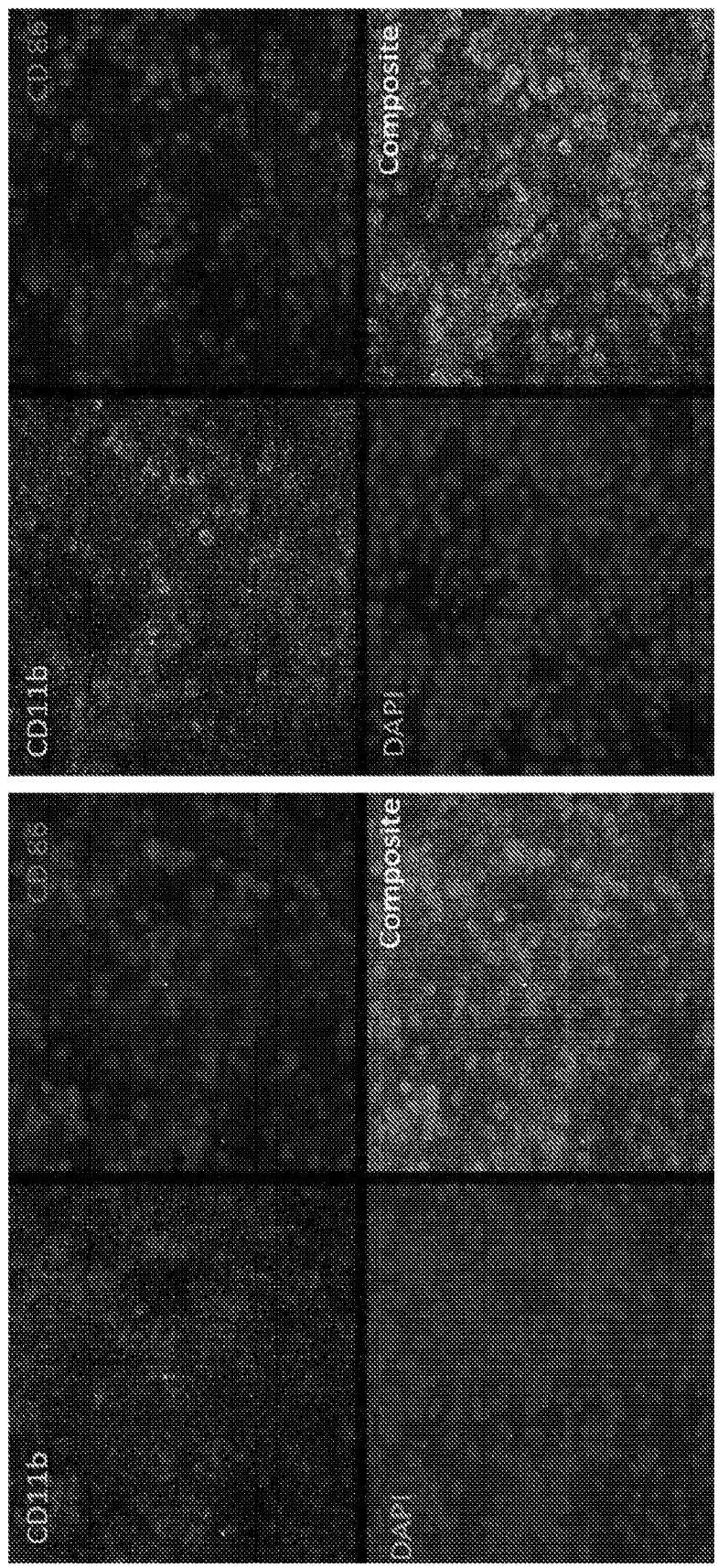

Amiodarone was shown to decrease cardiac force output by 50% in 4-O systems treated with amiodarone compared to untreated systems when added at an acute dose (50 uM) (FIG. 4B). Furthermore, addition of amiodarone reduced cardiac conduction velocity by 20% (FIG. 4C) and cardiac beat frequency by 45% (FIG. 4D) compared to untreated 3-O systems. This negative effect was exacerbated in all cases with the addition of THP-1 cells suggesting additional effects by these cells. Dosing 4-O systems acutely with amiodarone decreased force output by 80%, cardiac conduction velocity by 50%, and cardiac beat frequency by 60%. However, a recovery in conduction velocity and beat frequency was observed at D4 (FIG. 4B-D). FIG. 4E shows changes in skeletal muscle force (measurements from myotubes grown on cantilevers). The line graph shows changes to force over several days after dosing with amiodarone, compared to +THP cells only or untreated controls without THP cells. Amiodarone has no significant effect on skeletal muscle force (FIG. 4E). FIG. 4F shows immunocytochemistry of liver cells in systems with recirculating THP macrophages and treated with amiodarone. The increase in CD11b and CD86 staining compared to controls indicates infiltration of THP macrophages into the liver tissue module.

Figure 5A:
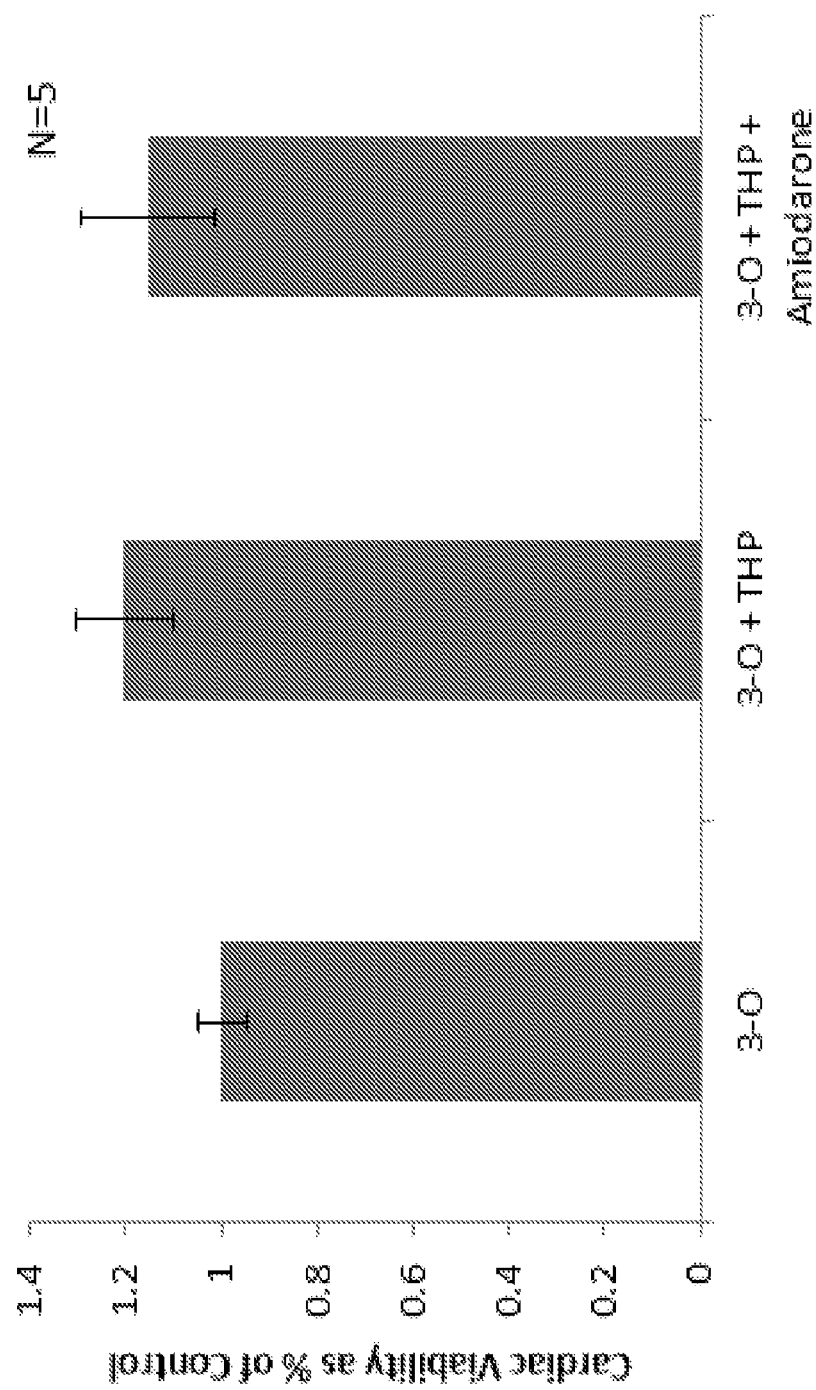
FIGS. 5A-5D show the THP-1 cell infiltration of the cardiac and skeletal cultures during treatment and resulting effects.
Figure 5B:
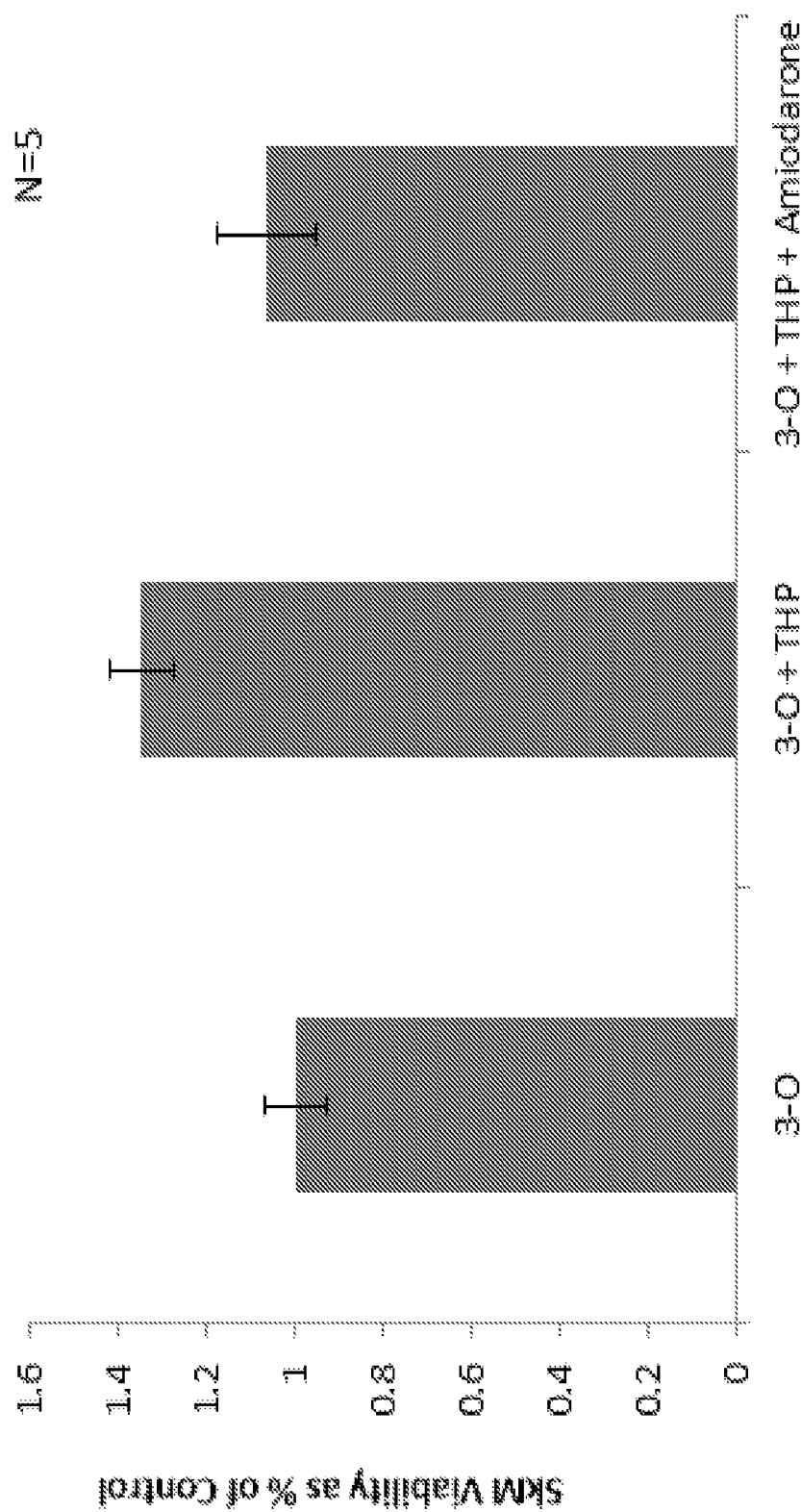
Figure 5C:
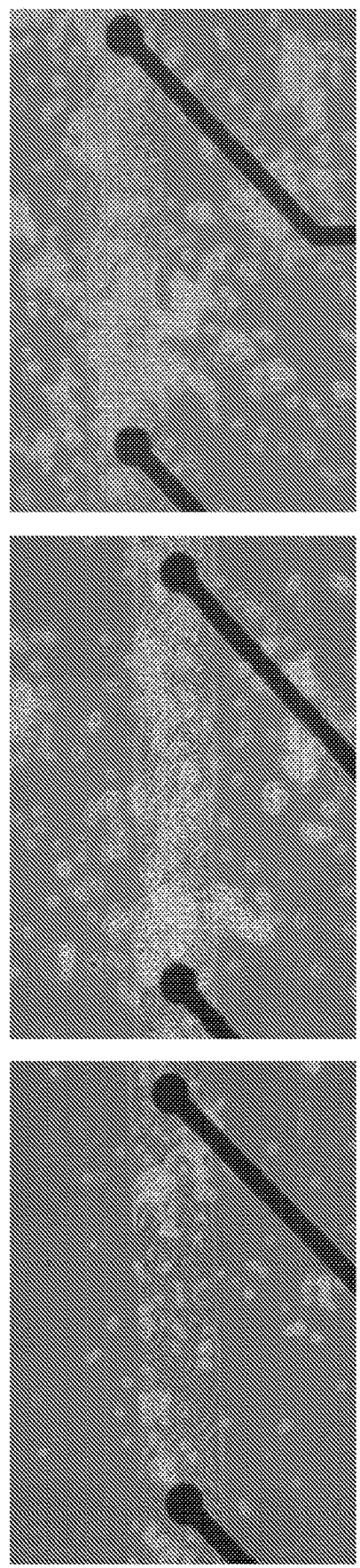
Figure 5D:
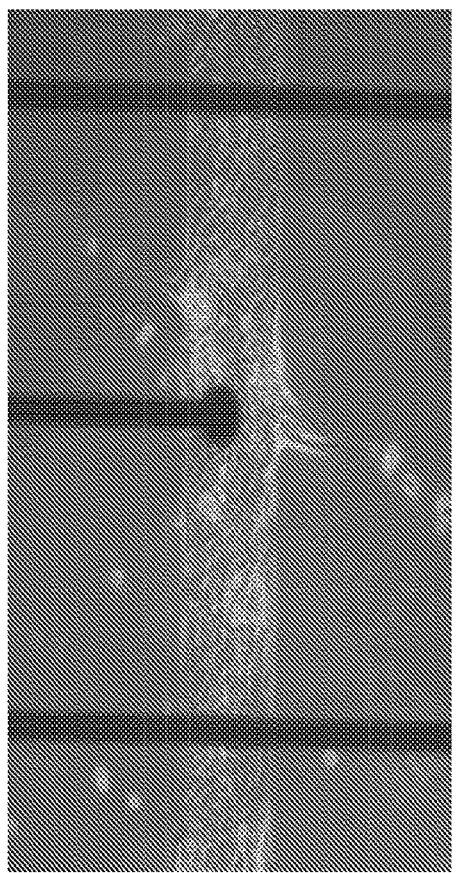
Figure 5D:
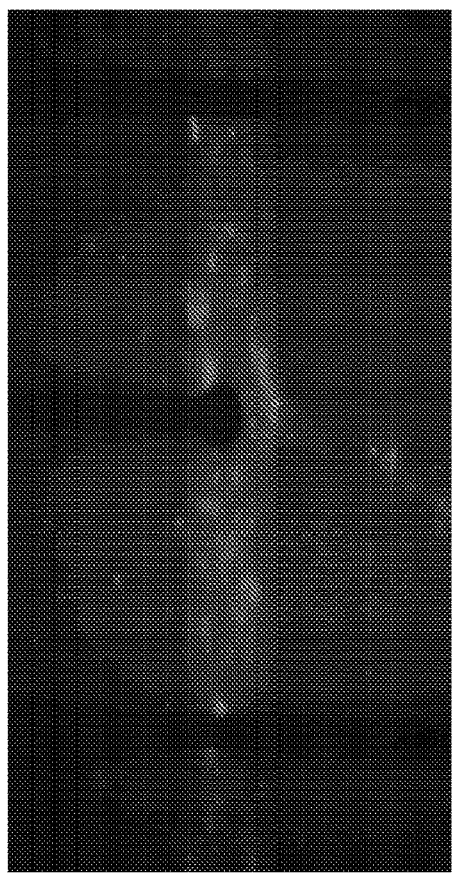

Endpoint viability assays run on the cardiac and skeletal muscle chips indicate that addition of amiodarone does not significantly reduce viability in any of the aforementioned organ modules, although small insignificant increases in skeletal muscle viability were observed when co-cultured with THP-1 cells (FIG. 5A-B). This may have been a result of THP-1 cell infiltration, as Alamar Blue utilizes colorimetric changes to determine viability compared to the control. The infiltration was evident in phase contrast images taken over the 7-day course of the experiment (FIG. 5C), which show THP-1 cell infiltration into cardiac tissue after amiodarone administration. To confirm THP-1 cell infiltration into the cardiac tissue, a culture of THP-1 cells were loaded with CellTracker Red CMTPX dye and added to a 4-O system and dosed with amiodarone. After three days, this system was imaged using epifluorescence microscopy. THP-1 cells were visibly infiltrated into the cardiac tissue (FIG. 5D).

The dose response analysis described above determined a concentration that amiodarone caused physiological dysfunction without inducing cell death (FIGS. 4B-E and FIG. 5A-5B). This allowed the study of the effects of cell damage, and the cytokines produced by the damaged cardiomyocytes, without the confounding variability of the release of necrotic debris recirculating in the system. As indicated by the functional readouts in FIGS. 4B-4E, amiodarone treatment impaired cardiac physiology while sparing skeletal muscle function two days post-treatment, and resulted in selective THP-1 cell infiltration into the cardiac tissue chips (FIGS. 5C and 5D).

Figure 6A:
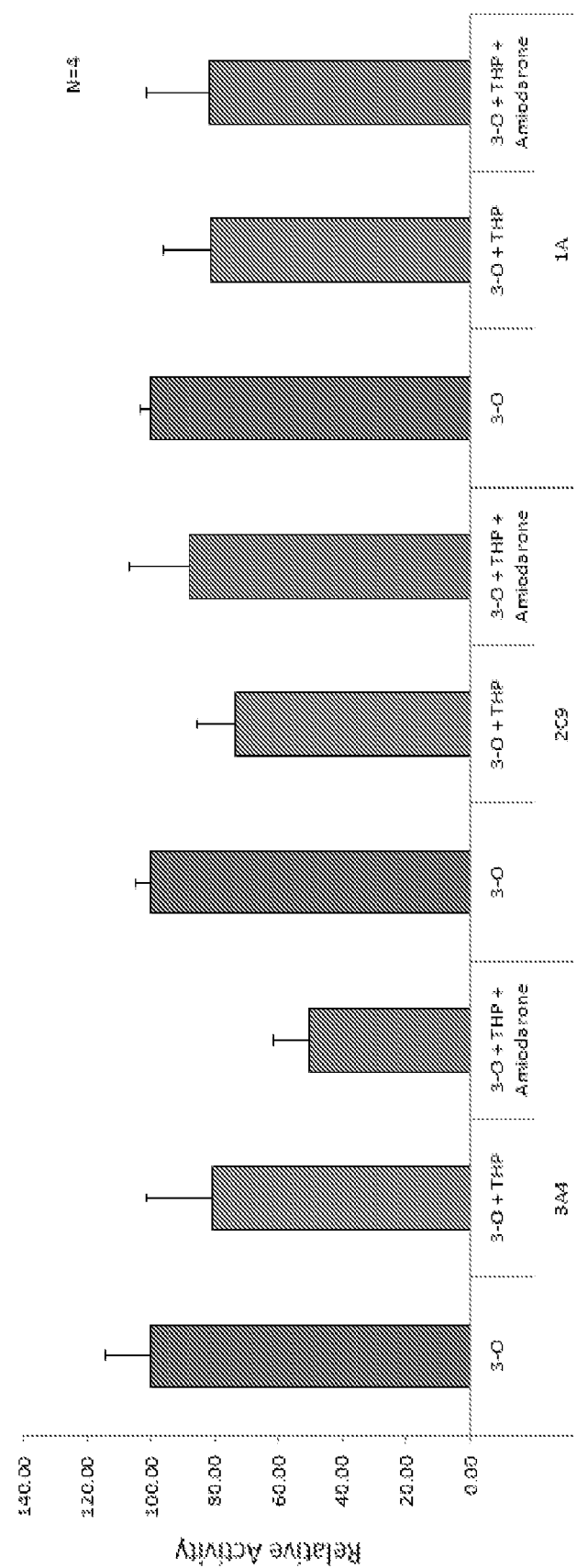
FIGS. 6A-D show liver physiology in multi-organ systems treated with amiodarone.
Figure 6B:
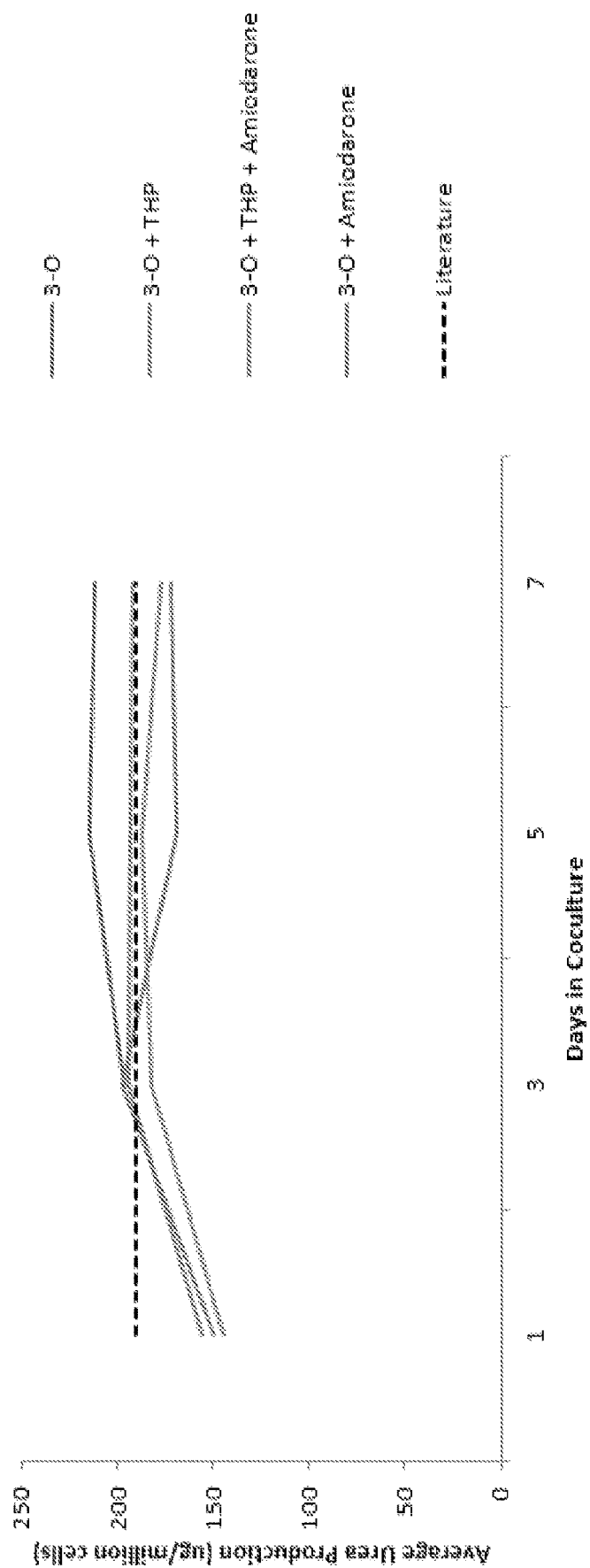
Figure 6C:
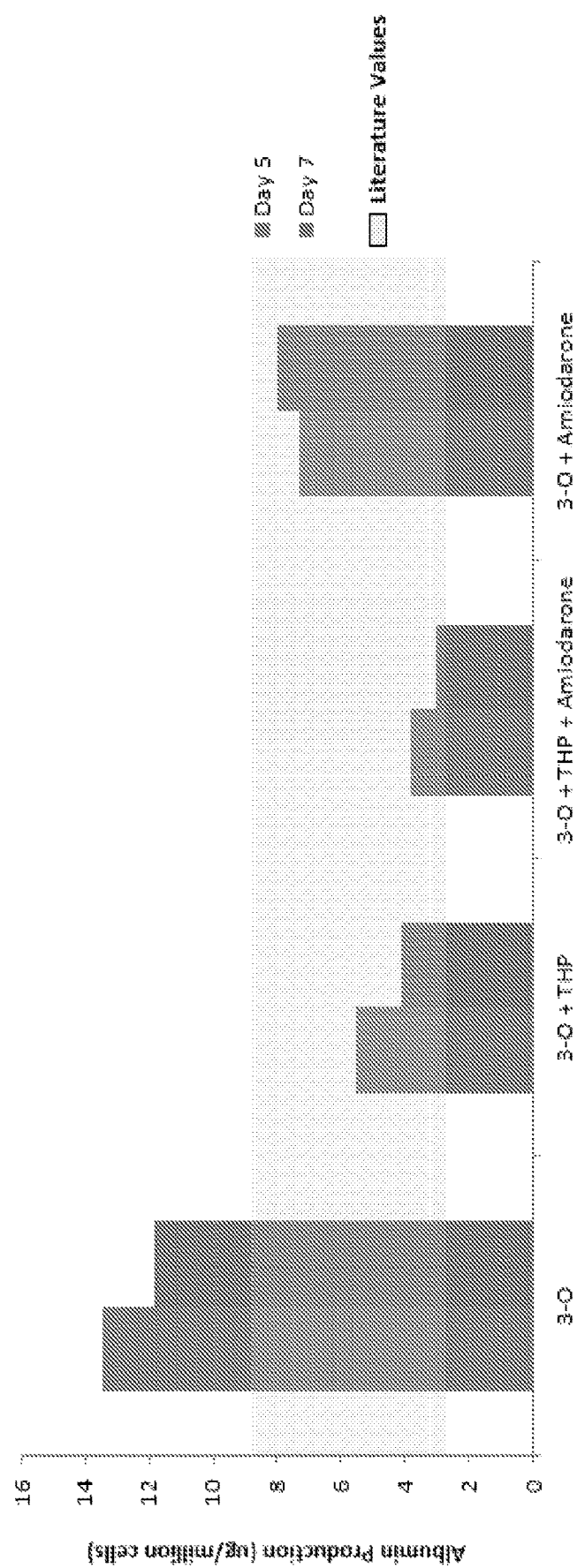
Figure 6D:
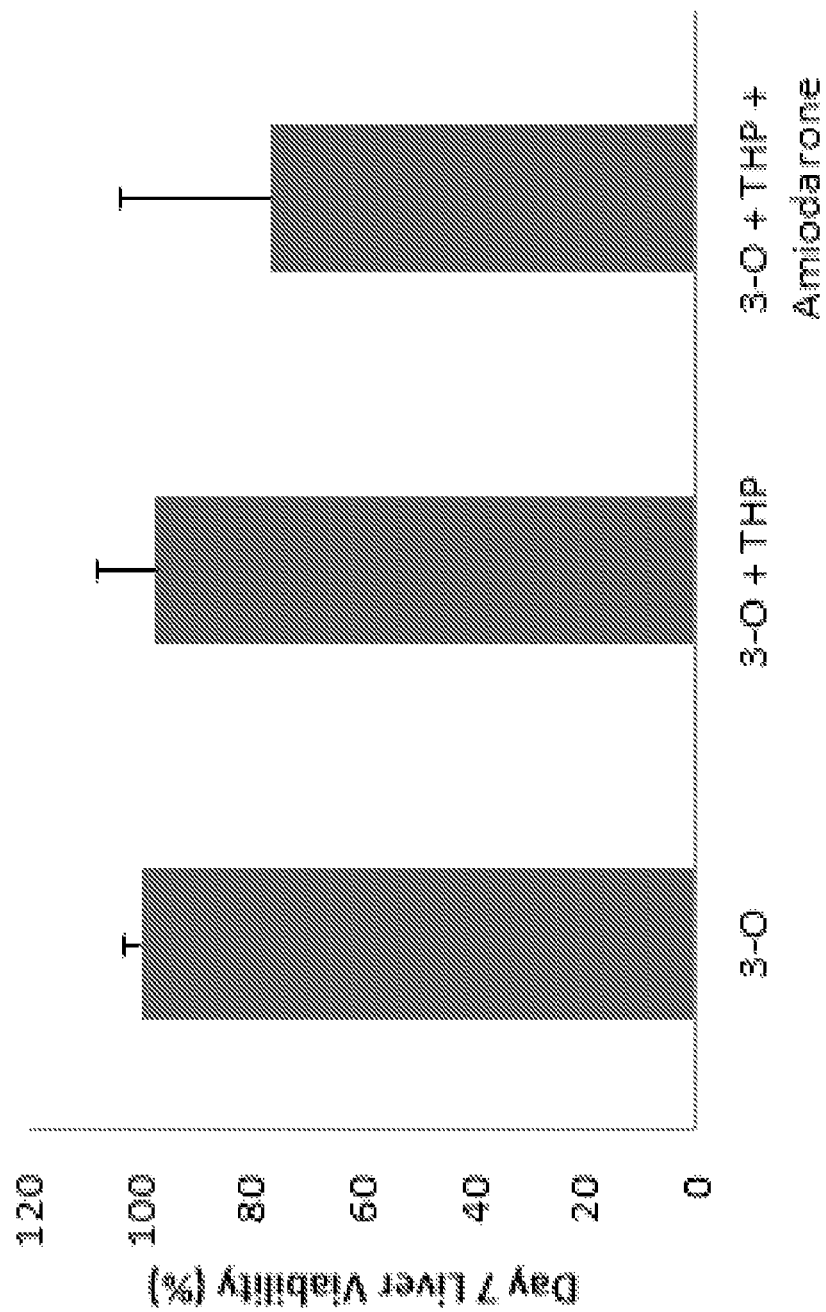

Liver cytochrome p450 activity was analyzed as an endpoint assay at D7. Activity levels of Cytochrome P (Cyp) 3A4, 2C9, and 1A were quantified and CYP3A4 activity was found to be significantly reduced in 4-O systems that were dosed with amiodarone vs. the untreated controls. As expected, CYP2C9 and CYP1A were not affected (FIG. 6A). The systems were fed daily with a 30% media change, removed media was frozen and stored for analysis. ELISA kits for liver urea and albumin production were run on these samples. Urea production was unaffected by the addition of amiodarone during the time course of the experiment (FIG. 6B). However, albumin production was negatively affected by the addition of amiodarone, and this effect was more pronounced with the addition of THP-1 cells (FIG. 6C). Endpoint viability assays indicate that amiodarone addition significantly reduces liver viability in the presence of THP-1 cells (FIG. 6D).

Figure 7A:
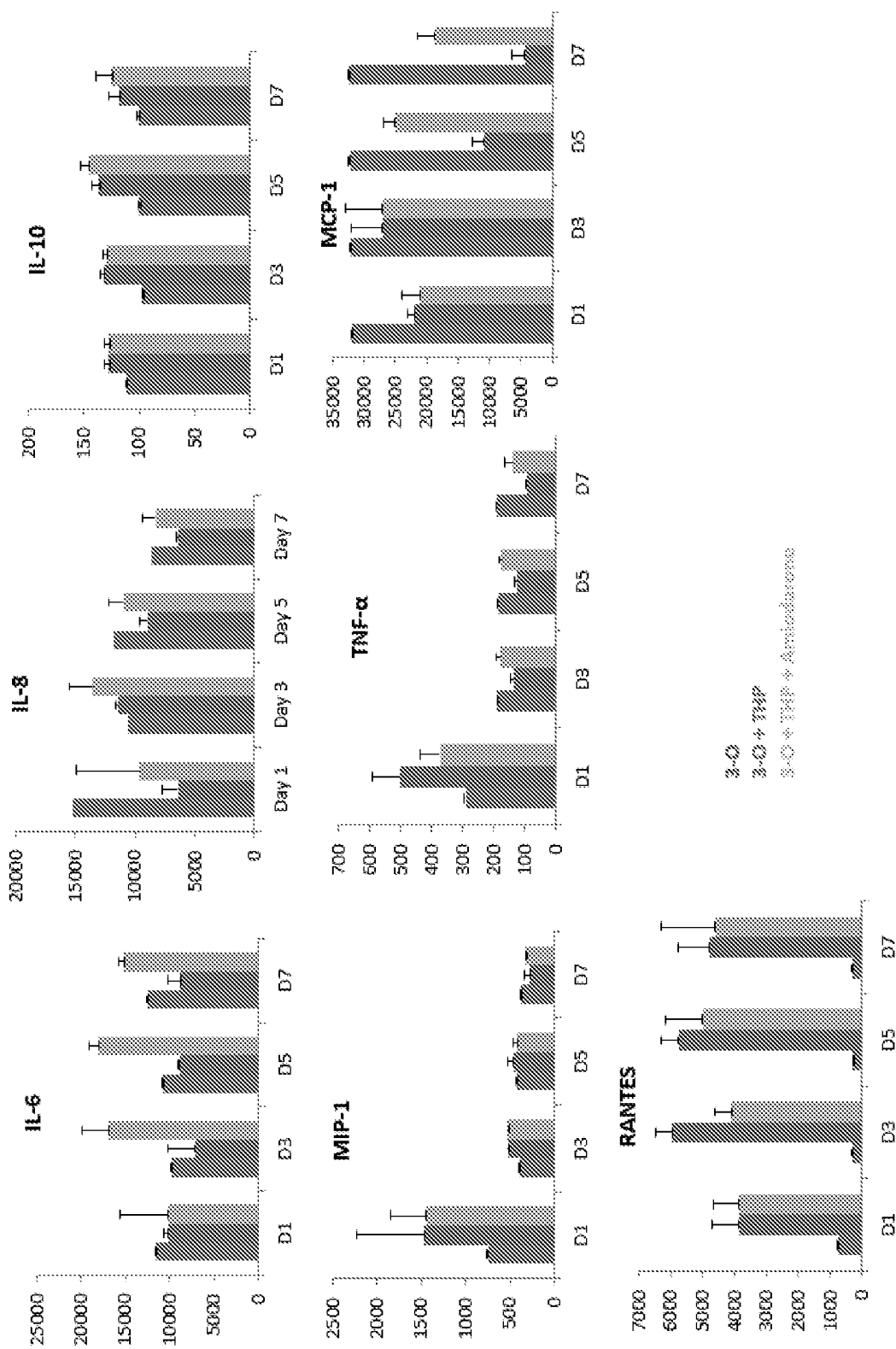
FIGS. 7A-C show cytokine release profiles and THP-1 cell activation levels in systems.

Release of cytokines IL-6, IL-8, IL-10, MIP-1, TFN-α, MCP-1, and RANTES were tracked throughout the time course of the experiment. TNF-α, RANTES and MIP-1 release were found to be increased by the addition of THP-1 cells, while addition of amiodarone increased levels of MCP-1, IL-6, and IL-8 (FIG. 7A).

Figure 7B:
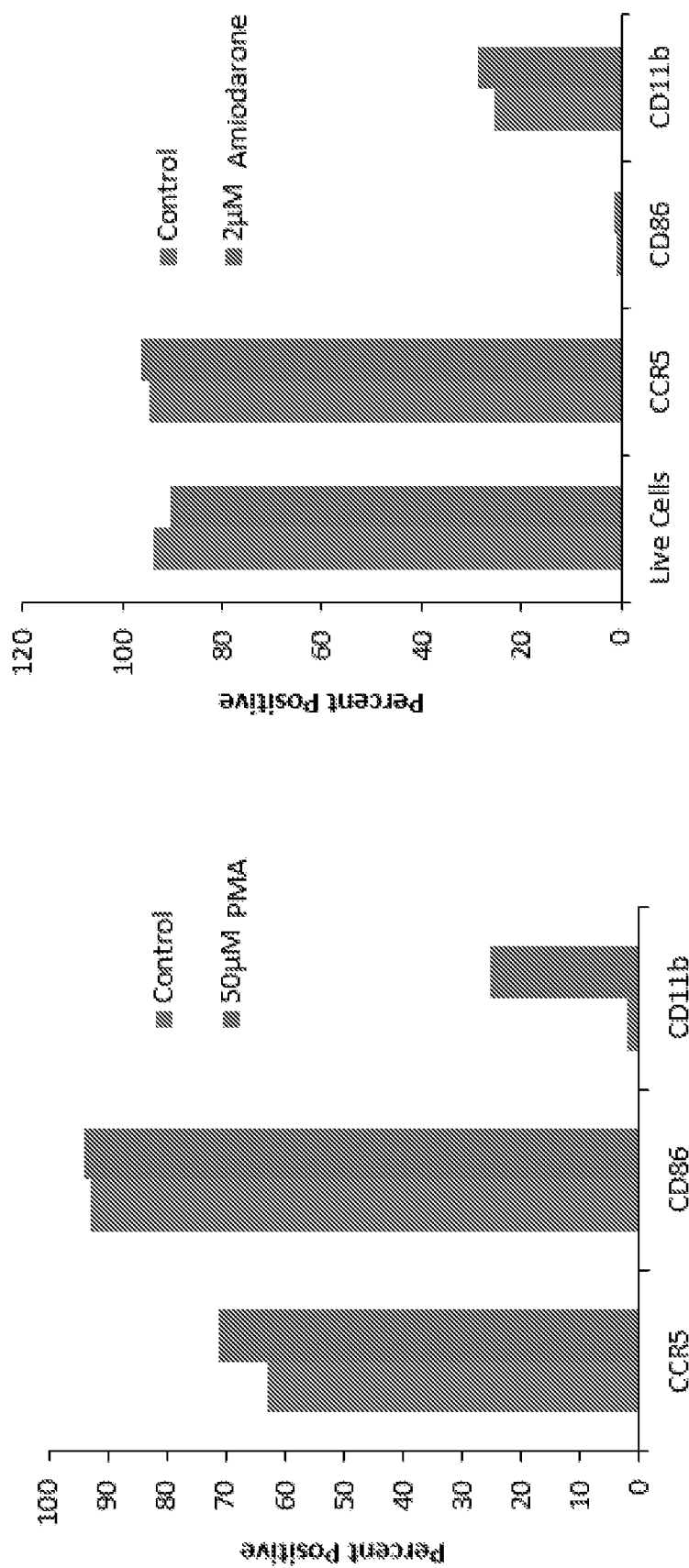
Figure 7C:
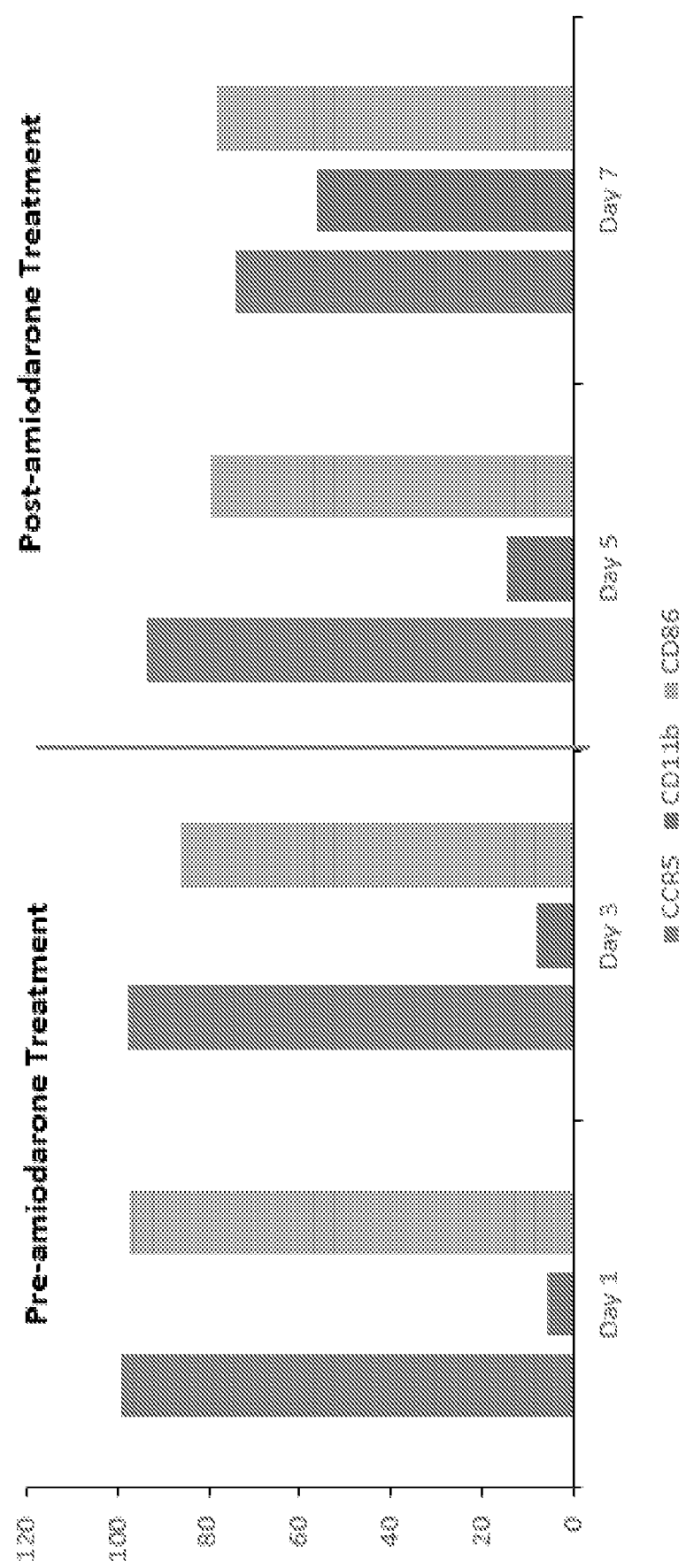

THP-1 cell activation levels were monitored by flow cytometry during the course of amiodarone treatment. A positive control for activation was run by dosing a culture of THP-1 cells with 50 µM phorbol myristate acetate (PMA), which has been shown to drive the differentiation of THP-1 monocytes into macrophages. This differentiation was evidenced by an 8% and 23% increase in CCR5 and CD11b expression respectively, both of which are commonly used as markers for monocyte differentiation. C86, a marker for macrophage proinflammatory activation, remained relatively unchanged (FIG. 7B). Amiodarone treatment of THP-1 cells alone did not significantly alter their viability or levels of CCR5, CD86, or CD11b expression (FIG. 7B). Taken together these data indicate that unlike PMA, amiodarone does not directly activate THP-1 macrophages. Freely recirculating THP-1 cells were drawn from the 4-O & 4-O+Amiodarone systems on days 1, 3, 5, 7 and analyzed by flow cytometry for their expression of CCR5, CD11b, and CD86 receptors. Expression of CCR5 and CD86 remained largely stable over the six-day window, while CD11b increased. These data indicate that CD11b is an important indicator of THP-1 cell activation in response to amiodarone treatment and subsequent cardiac cell damage (FIG. 7C).

As outlined above, amiodarone had no direct effect on THP cell activation, however, when systems containing recirculating THP cells were dosed with amiodarone there was a delayed, but pronounced induction of CD11b suggesting cytokines produced by damaged cardiomyocytes caused THP activation (FIGS. 7B&C). From the cytokine data collected the exact program driving THP cell activation is unclear, however, the increasing and sustained levels of IL-6 from day 3 through day 7 suggests it played a role in the increased expression of CD11b on THP macrophages (FIG. 7A).

Global/Holistic/Immune Response (LPS+IFN-γ Data Set):

Expanding on the amiodarone data, where a single organ was targeted in the systems, compounds known to directly stimulate recirculating monocytes were tested and monocyte activation and organ infiltration levels were measured. Lipopolysaccharide (LPS) and interferon gamma (IFN-γ) were selected for the robust effects they elicit on monocyte differentiation and activation in vivo and in vitro. This treatment regime mimics a cytokine-storm/sepsis-like scenario and, facilitates an investigation into the effects of "classical" macrophage activation on cardiac, skeletal muscle and liver function. Furthermore, when compared to amiodarone treated systems, these two divergent approaches to macrophage activation allow the dissection of these programs and can be used to predict unknown compound behavior. Specifically, does compound X have site-directed immune effects, or does it directly activate recirculating macrophages.

Figure 8A:
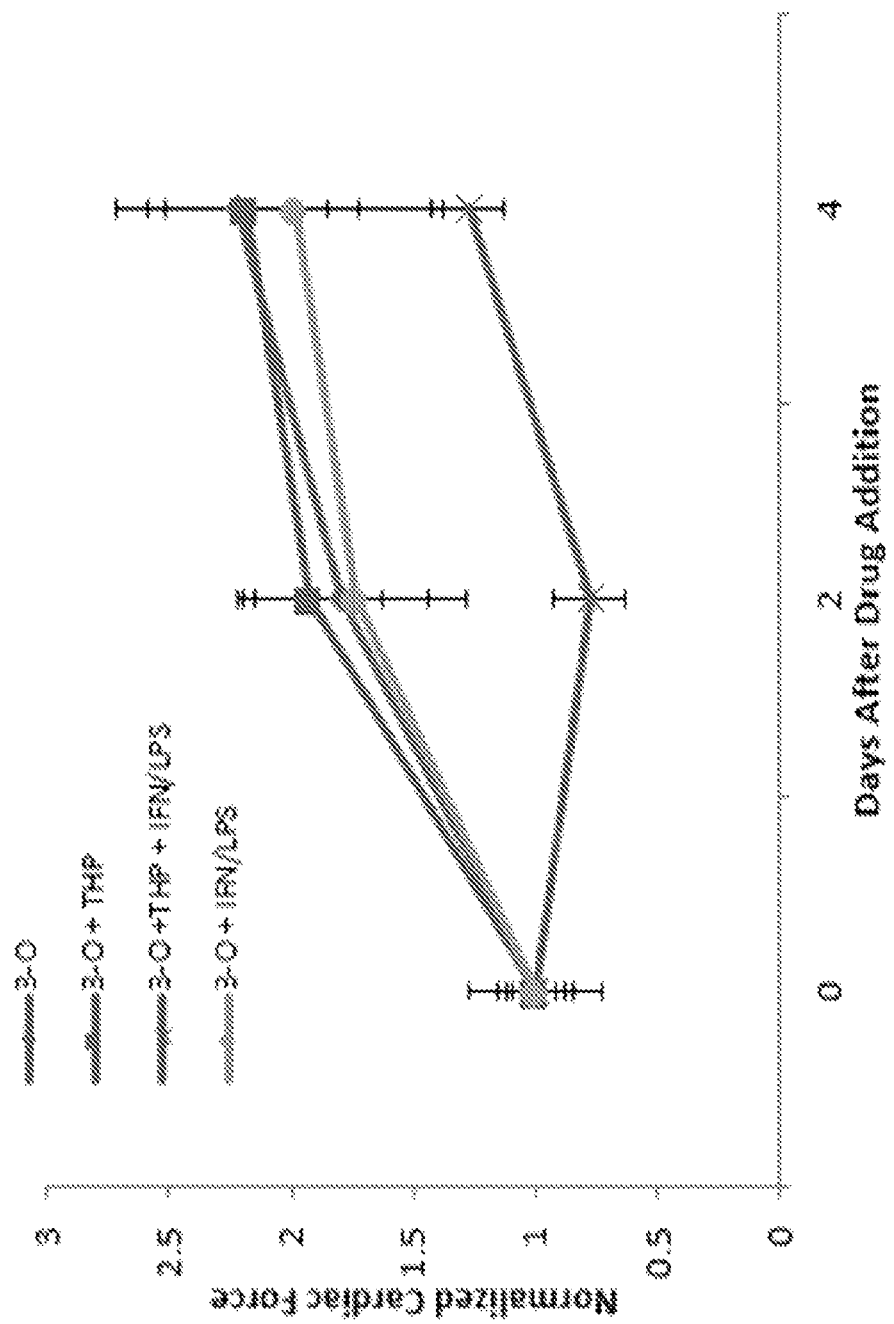
FIGS. 8A-D show results from the functional evaluation of cardiomyocytes and skeletal muscle myotubes in LPS and IFN-γ treated 3-O systems+THP-1 cells.
Figure 8B:
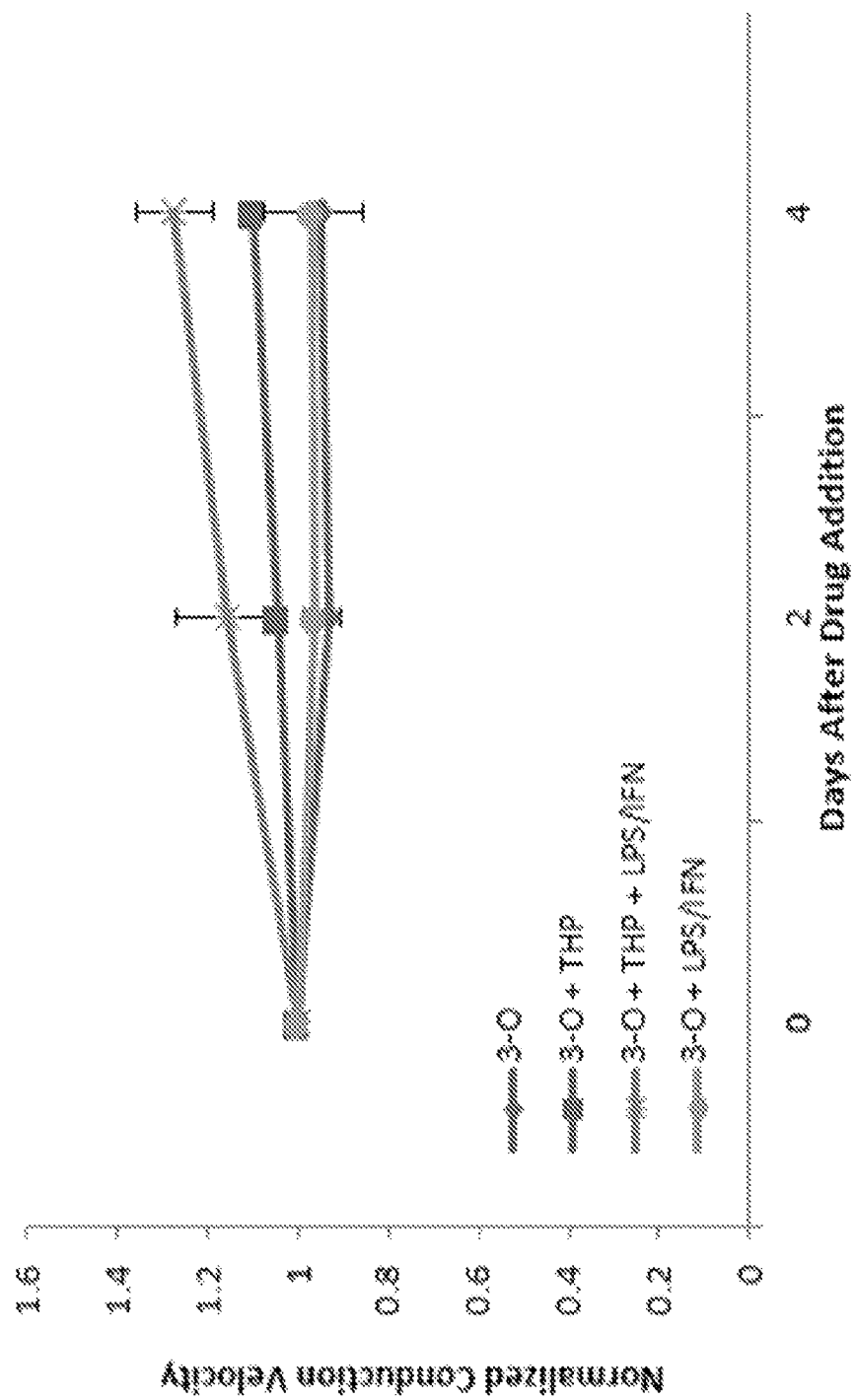
Figure 8C:
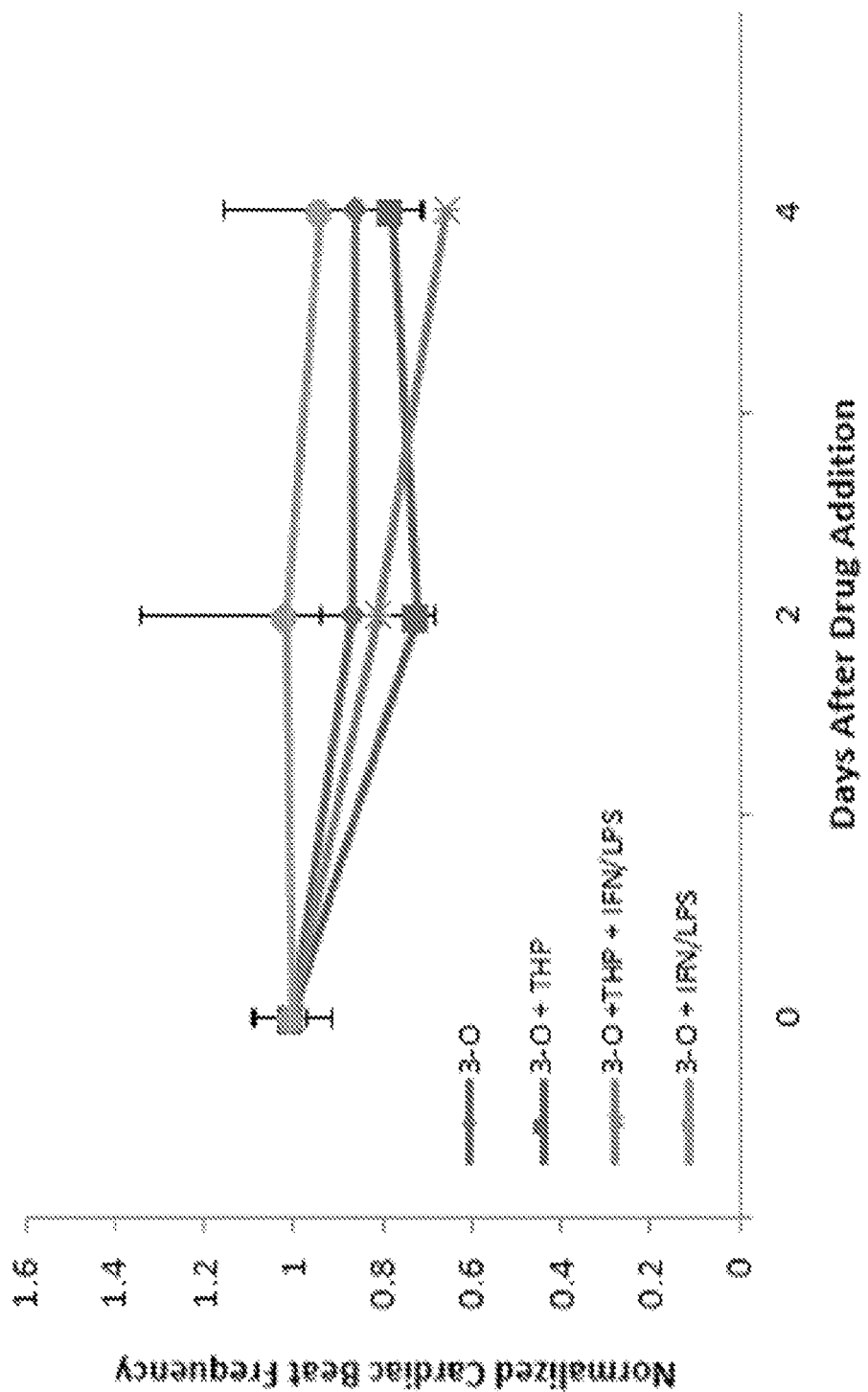
Figure 8D:
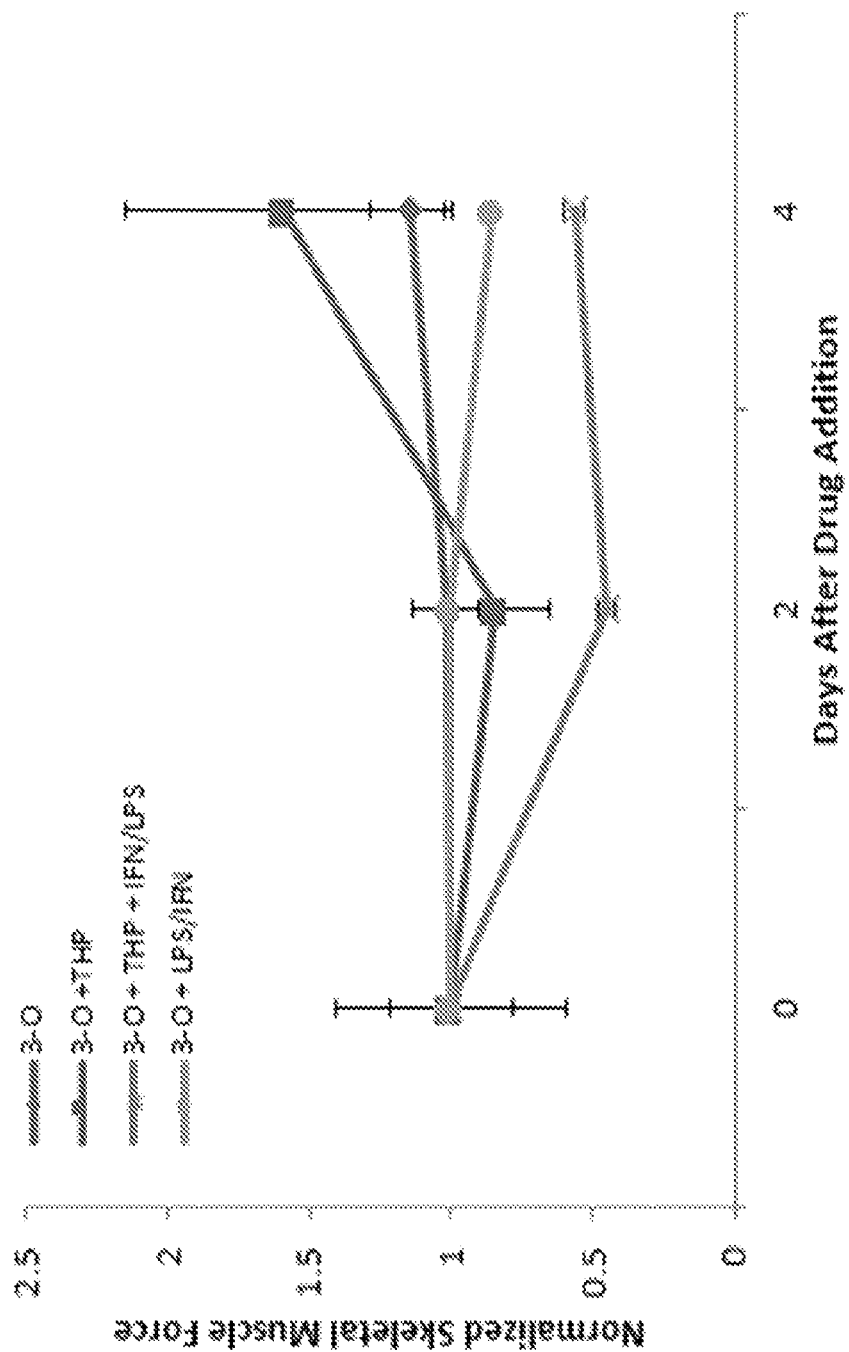

A cocktail of LPS (long/mL) and IFN-γ (100 U/mL) was added to our systems on D3 after assembly. Cardiac and skeletal muscle functionality was evaluated on D3, D5, and D7; immediately before dose, 2 days after, and 4 days after dose administration, respectively. LPS/IFN-γ addition in the absence of THP-1 had no effect on cardiac force, cardiac spontaneous beat frequency, or skeletal muscle contractile force (FIG. 8A, C, D). It did, however, negatively affect cardiac conduction velocity, resulting in a 17% decrease compared to the control systems (FIG. 8B). THP-1 cell containing 4-O systems dosed with the LPS/IFN-γ cocktail exhibited a 40% reduction in cardiac contractile force, a 15% increase in cardiac conduction velocity by day 4, and a 40% reduction in skeletal muscle force compared to control 4-O systems. Cardiac spontaneous beat frequency in 4-O systems remained unaffected by the addition of the LPS/IFN-γ cocktail (FIG. 8C). Interestingly, skeletal muscle force generation was impaired in systems treated with LPS+IFN-γ in contrast to amiodarone treated systems (FIG. 8D).

Figure 9A:
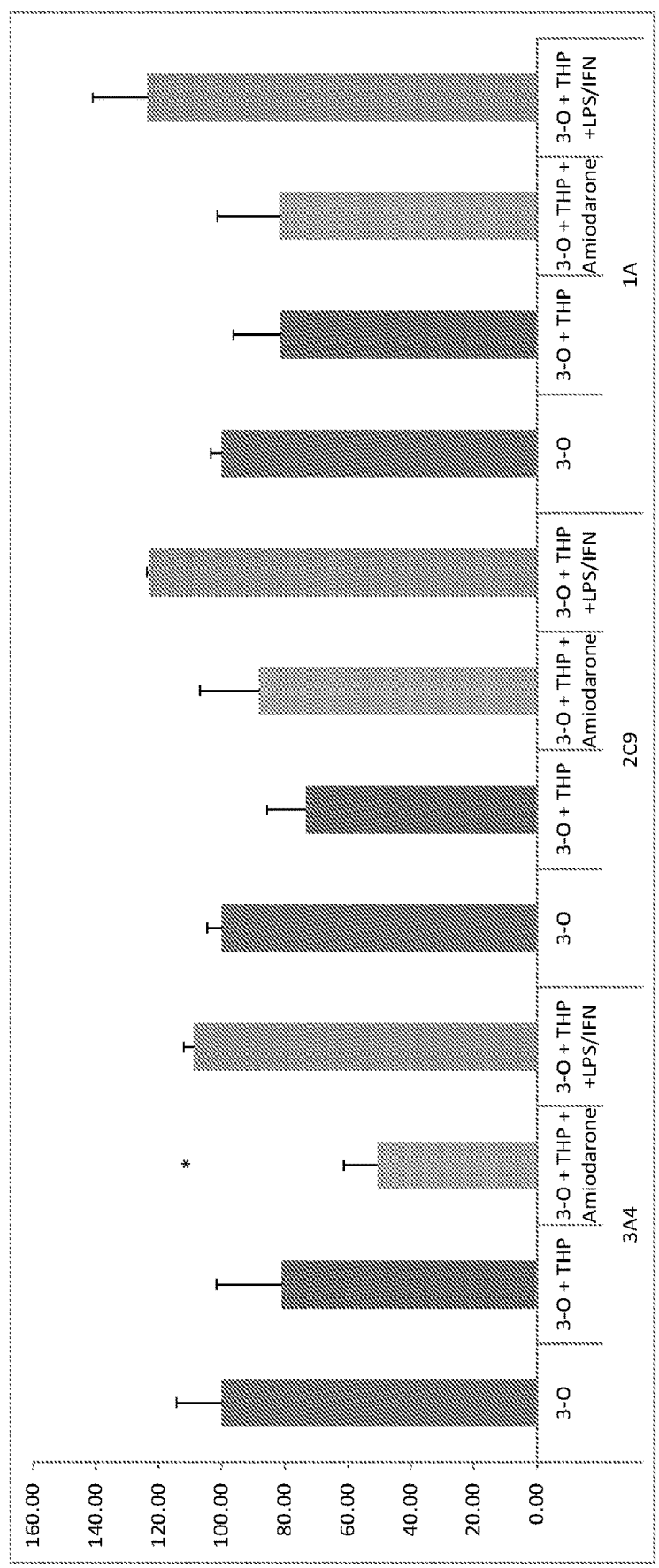
FIGS. 9A-D show liver cell function in multi-organ systems treated with LPS+ IFNγ.
Figure 9B:
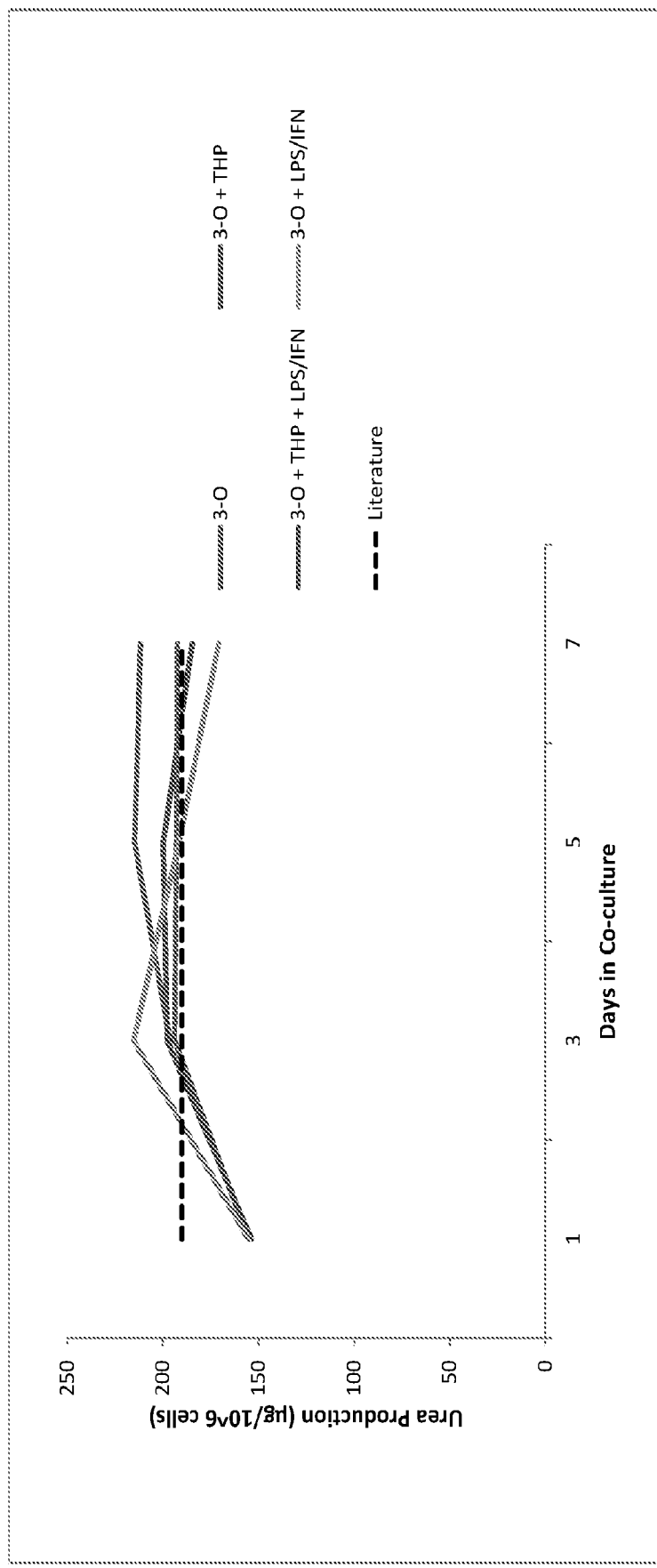
Figure 9C:
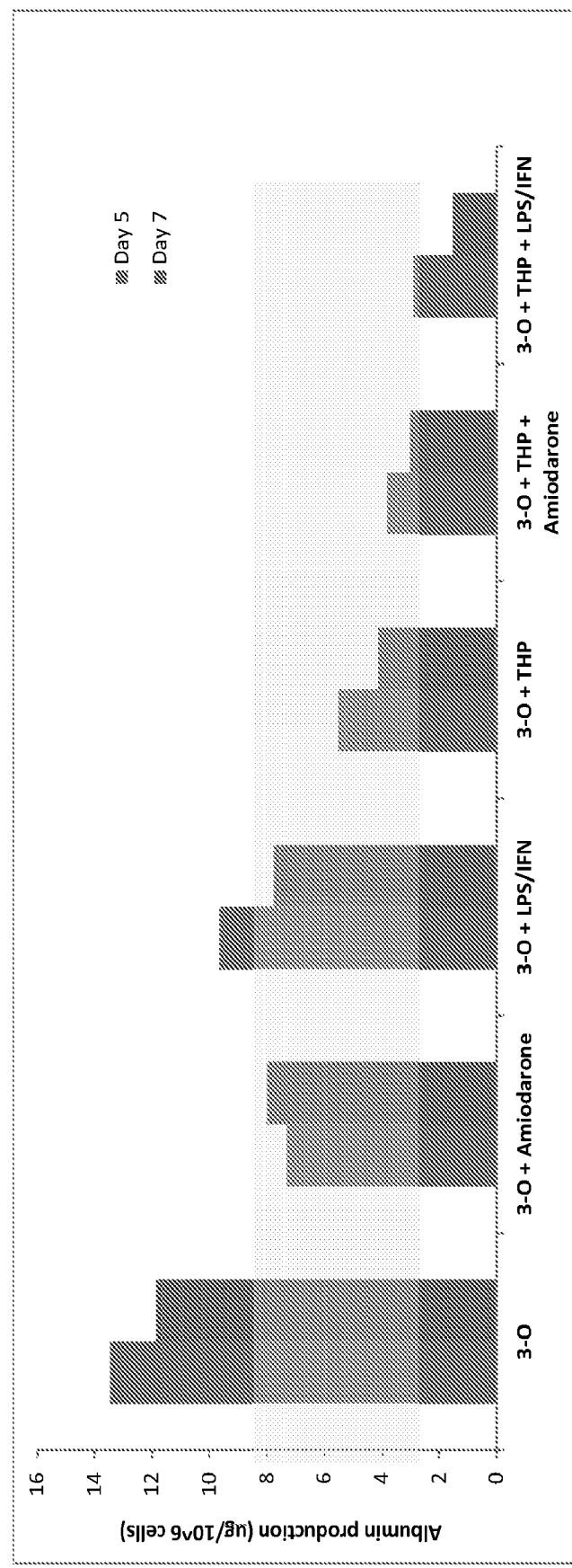
Figure 9D:
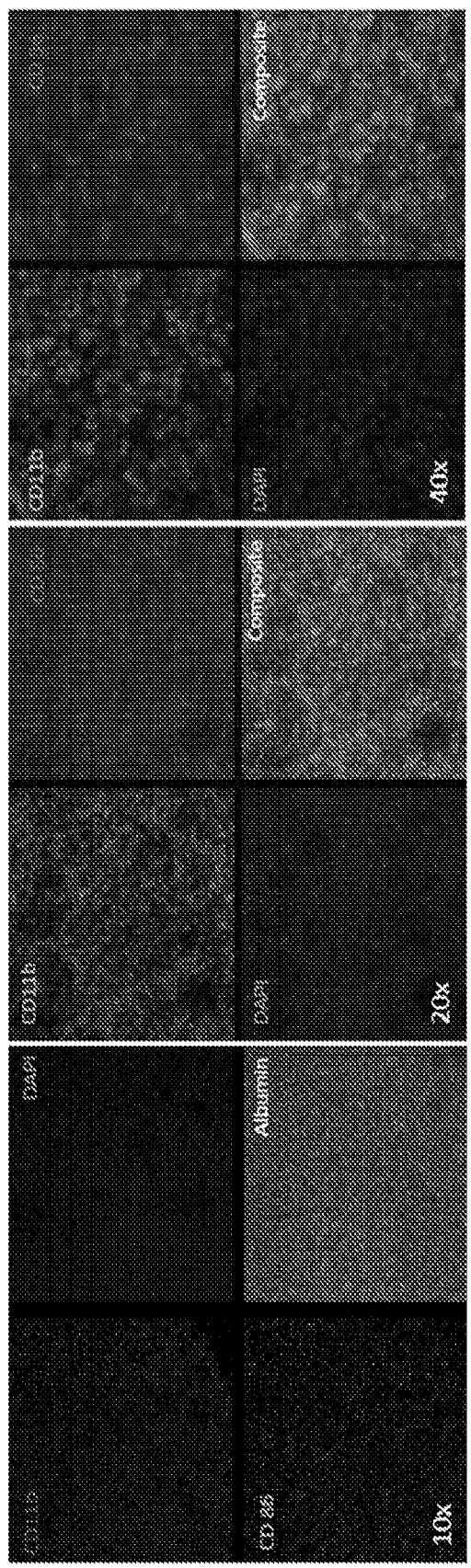

Cyp 3A4, 2C9, and 1A activities in the liver were evaluated at D7. LPS/IFN-γ addition had no effect on Cyp 3A4 activity, but elevated 2C9 and 1A activities slightly in comparison to the standard activity in untreated 4-O systems (FIG. 9A). Hepatocyte functionality was evaluated by measuring their levels of urea and albumin production. 4-O+ LPS/IFN-γ hepatocytes exhibited a decrease in albumin production when exposed to LPS/IFN-γ, by 45% at day 5 and 63% at day 7 in comparison to the liver modules in control 4-O systems. Urea production by the hepatocytes was unaffected by the addition of the LPS/IFN-γ cocktail (FIG. 9B-C). Immune cell infiltration was evident in the liver module, and this infiltration was confirmed by immunocytochemistry. Liver coverslips from 4-O systems and 4-O+LPS/IFN-g systems were stained for CD11b, CD86, and DAPI. CD11b staining in liver tissue was increased in the LPS/IFN-g systems compared to the controls, indicating THP-1 cell infiltration (FIG. 9D).

While the data described above suggest a healthy liver module in the presence of recirculating THP-1 cells treated with LPS+IFN-γ, albumin production was significantly decreased in these conditions compared to systems treated with LPS+IFN-γ alone or with recirculating THP-1 cells alone (FIG. 9C). Taken together, these data indicate liver albumin production's sensitivity to compound treatment and THP-1 cell infiltration. Moreover, the stratification of the results obtained make this a useful test for assessing liver function in presence of compounds with unknown effects.

Figure 10A:
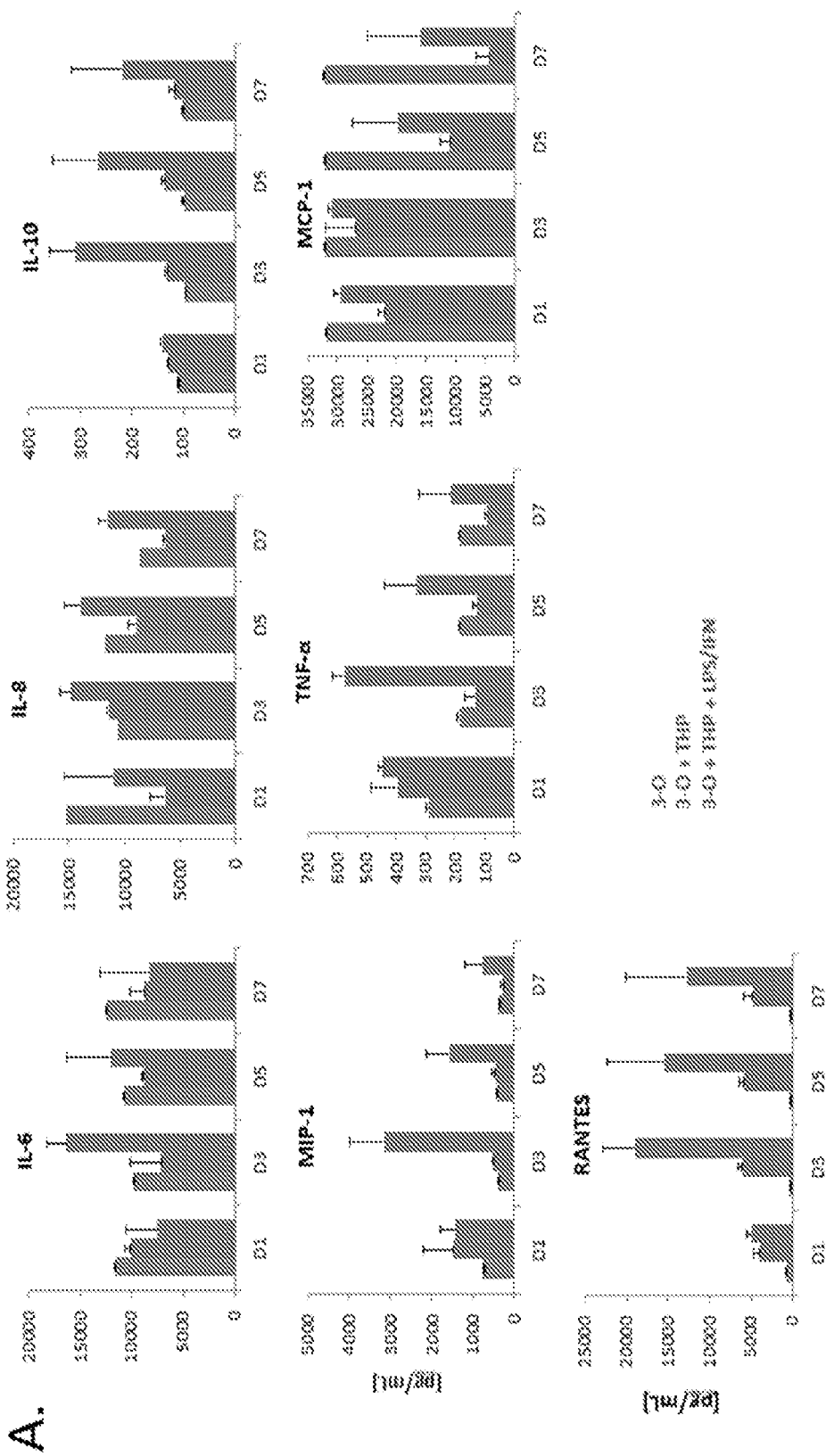
FIG. 10A shows cytokine release profiles and THP-1 cell activation 1, 3, 5, and 7 days after LPS+ IFNγ treatment of 3-O systems+THP-1 cells.
Figure 10B:
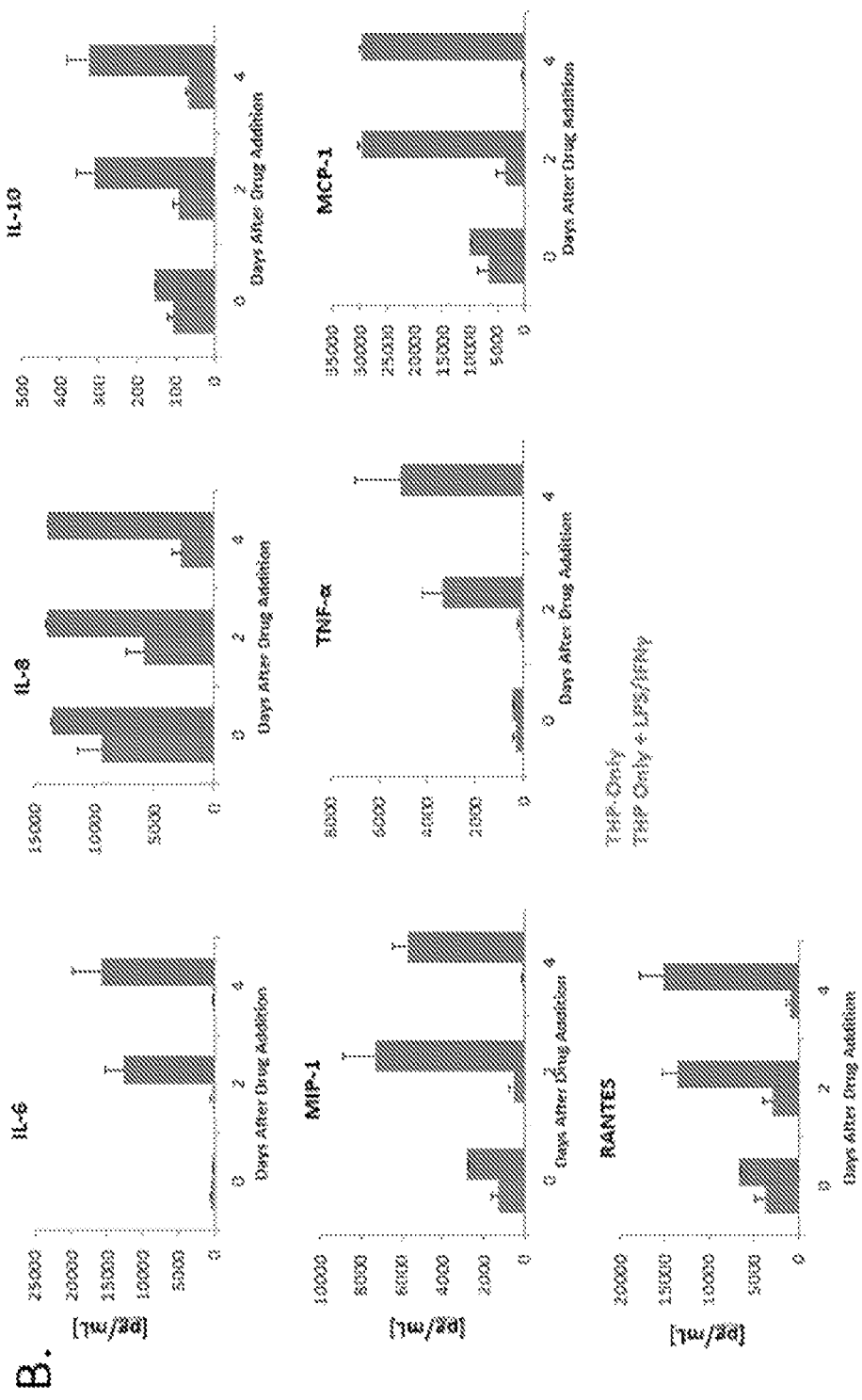
FIG. 10B shows cytokine levels in LPS+ IFNγ dosed systems that only contained recirculating THP-1 cells.
Figure 10C:
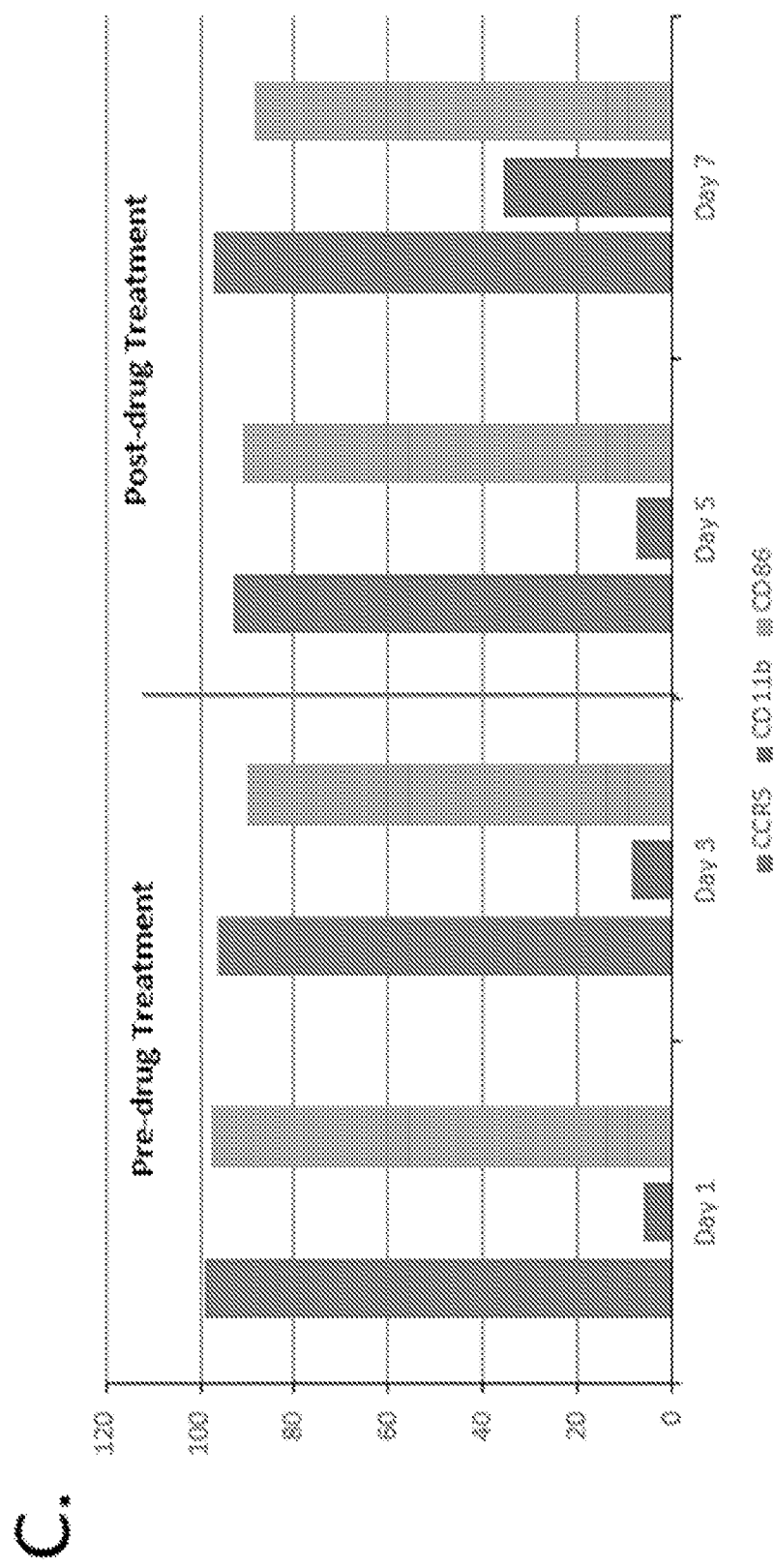
FIG. 10C shows CCR5, CD11b, and CD86 expression before and after dosing with LPS/IFN-γ. CD11b expression increased at day 7.

Release of cytokines IL-6, IL-8, IL-10, MIP-1, TFN-α, MCP-1, and RANTES was tracked on D1, D3, D5, and D7 after assembly. LPS/IFN-γ addition was shown to significantly increase levels of RANTES, TNF-α, MIP-1, IL-8 and IL-10 in 4-O+LPS/IFN-γ systems (FIG. 10A). Levels of each one of these cytokines were also elevated in LPS/IFN-γ dosed systems that only contained recirculating THP-1 cells, indicating that THP-1 cell activation was primarily induced by the LPS/IFN-γ activation cocktail (FIG. 10B). THP-1 CCR5, CD11b, and CD86 receptor expression was evaluated at D1, D3, D5 and D7 of recirculation with the LPS/IFN-γ being added on D3 after THP-1 cells were drawn from the systems. No significant changes in receptor expression were observed until D7, at which point CD11b expression was elevated 7-fold (FIG. 10C).

Figure 11B:
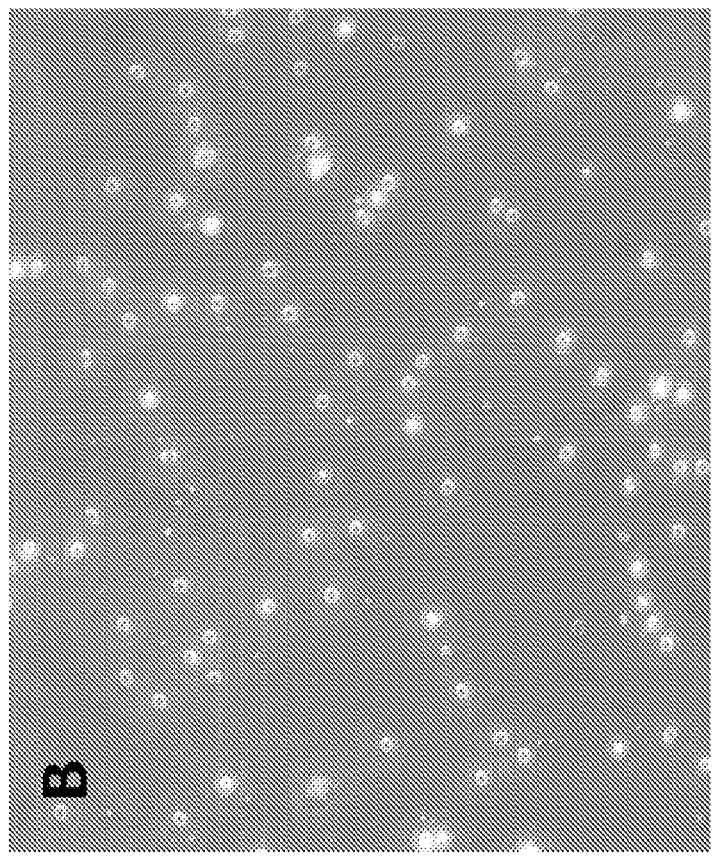
FIGS. 11A to 11F show results from experiments with peripheral blood mononuclear cells (PBMCs) at day 2.
Figure 11A:
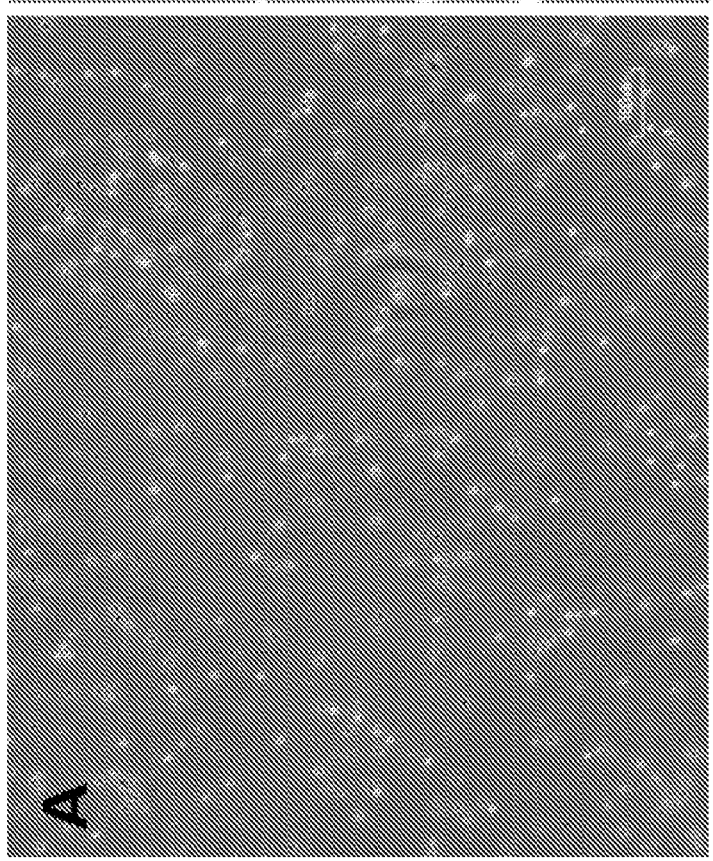
Figure 11C:
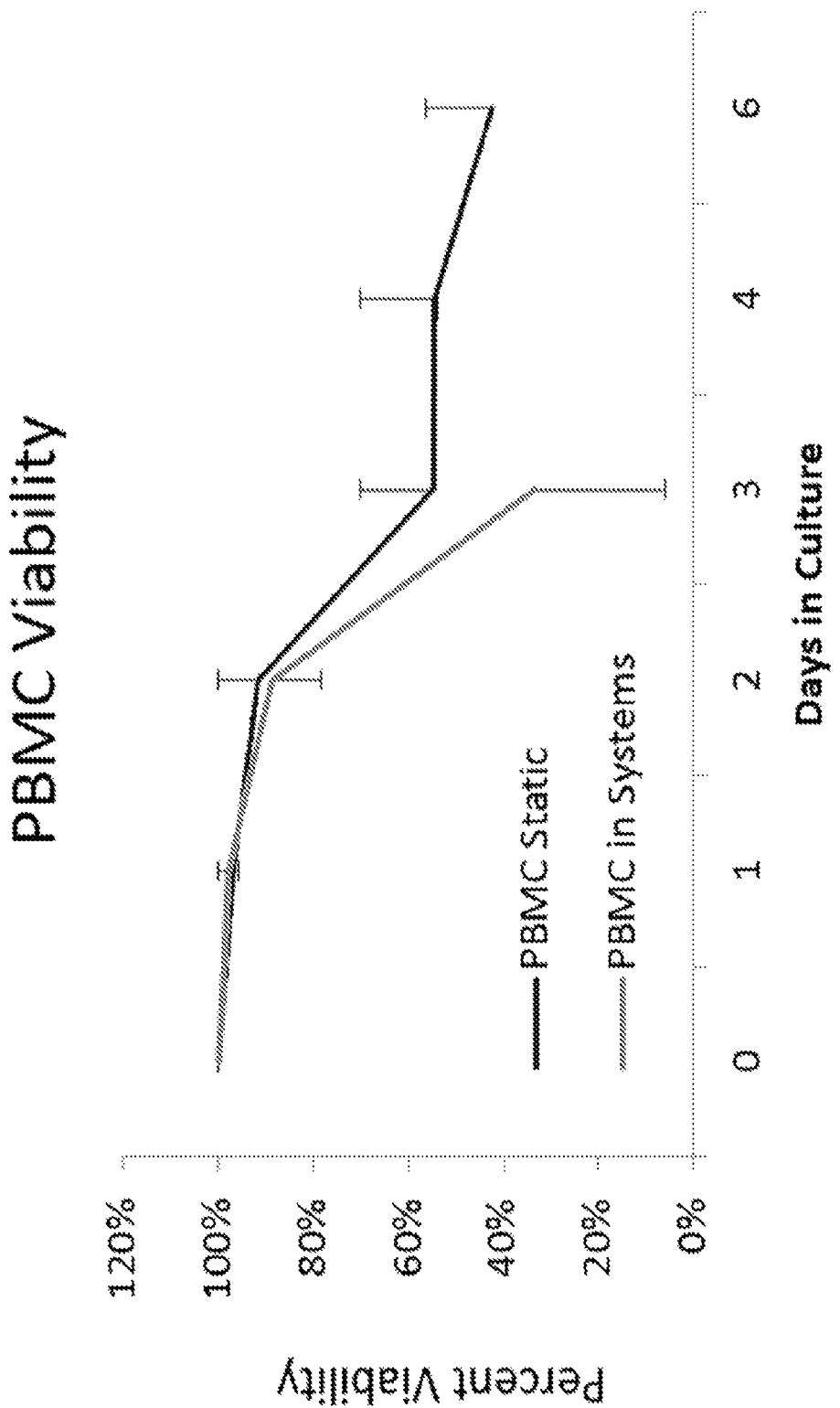
Figures 11D, 11E:
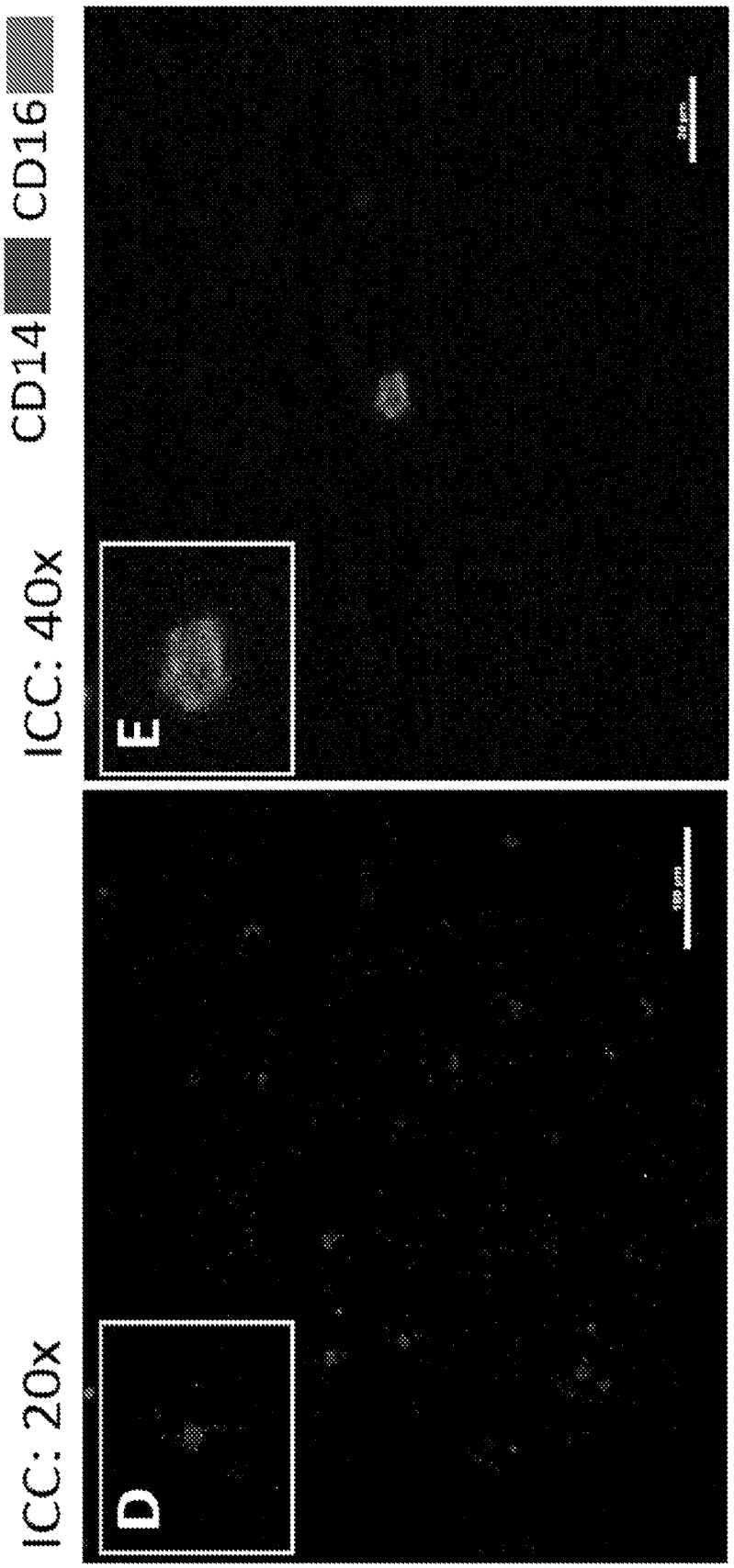
Figure 11F:
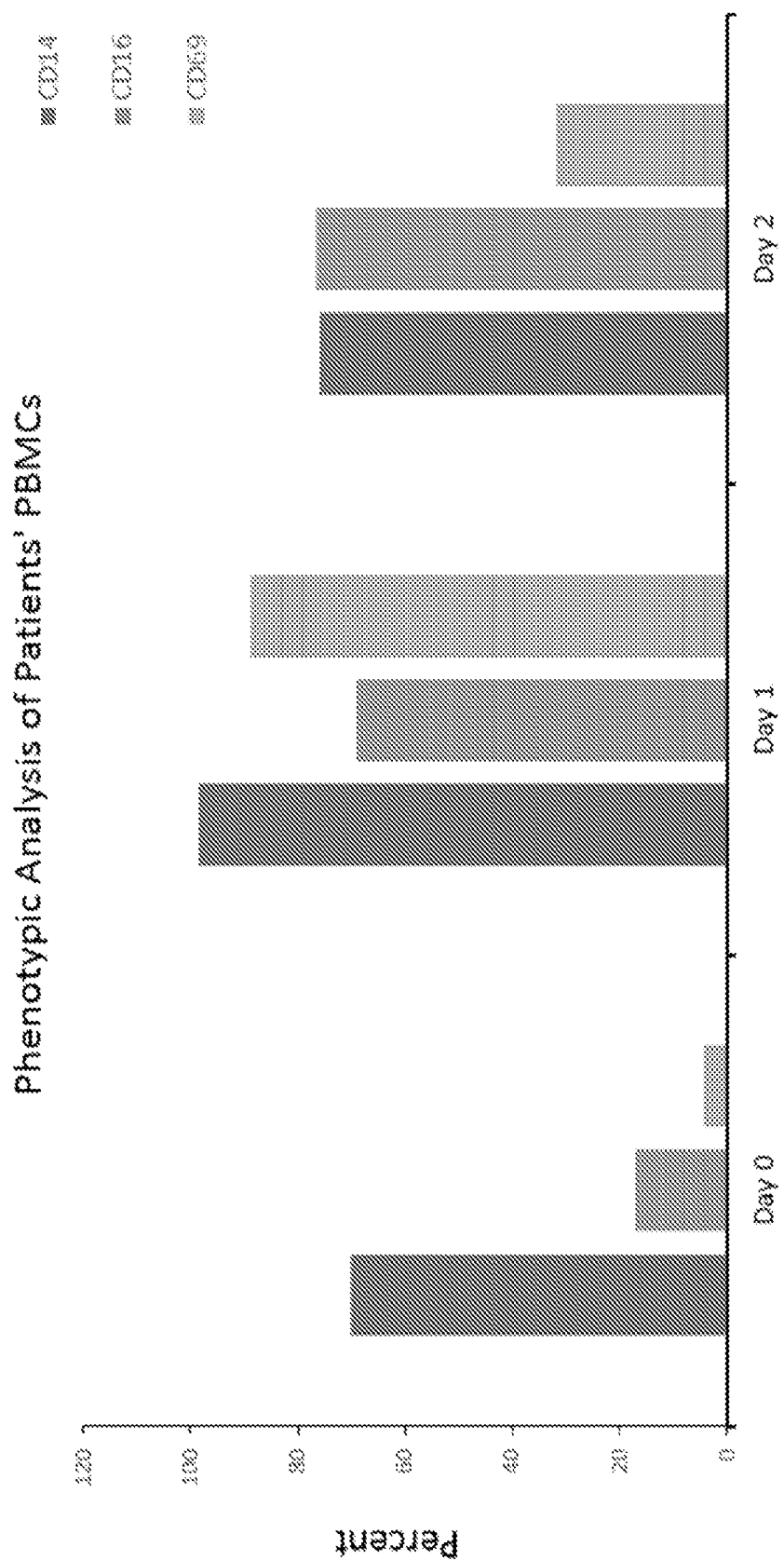

FIGS. 11A to 11F show results from experiments with peripheral blood mononuclear cells (PBMCs) at day 2. FIGS. 11A and 11B show phase contrast images of PBMCs. FIG. 11C demonstrates that cell viability in the systems is similar to that found under static conditions on days 1 and 2. FIGS. 11D and 11E show that the PBMCs stain positively for the surface marker CD14. Further analysis of patient PBMCs by flow cytometry (FIG. 11F) indicates populations of cells express the CD14, CD16, and CD69. These data indicate the intrinsic population variability in patient-derived PBMCs, and illustrate the system's ability to evaluate patient-specific treatment programs, as indicated by FIG. 11F.

REFERENCES

Agarwal A, et al. Microfluidic heart on a chip for higher throughput pharmacological studies. Lab on a chip, d (2013).

Bellas E, et al. In vitro 3D full-thickness skin-equivalent tissue model using silk and collagen biomaterials. Macromolecular bioscience 12, 1627-1636 (2012).

Bers D M. Cardiac excitation-contraction coupling. Nature 2002; 415(6868): 198-205.

Carlsson L. In vitro and in vivo models for testing arrhythmogenesis in drugs. Journal of Internal Medicine 2006; 259(1): 70-80.

Dakhel Y, et al. Erythomycin potentiates pr interval prolonging effect of verapamil in the rat: A pharmacodynamic drug interaction. Toxicol Appl Phamacol 2006; 214: 24-29.

Das M, et al. A defined long-term in vitro tissue engineered model of neuromuscular junctions. Biomaterials 2010; 31: 4880-4888.

Das M, et al. Differentiation of skeletal muscle and integration of myotubes with silicon microstructures using serum-free medium and a synthetic silane substrate. Nature Protocols 2007; 2(7): 1795-1801.

Das M, et al. Embryonic motor neuron-skeletal muscle co-culture in a defined system. Neuroscience 2007; 146: 481-488

Das M, et al. Long-term culture of embyonic rat cardiomyocytes on an organosilane surface in a serum free medium. Biomaterials 2004; 25(25): 5643-5647.

Das M, et al. Skeletal muscle tissue engineering: A maturation model promoting long-term survival of myotubes, structural development of the excitation-contraction coupling apparatus and neonatal myosin heavy chain expression. Biomaterials 30, 5392-5402 (2009).

Das M, et al. Skeletal muscle tissue engineering: An improved model promoting long term survival of myotubes, structural development of e-c coupling apparatus and neonatal myosin heavy chain (mhc) expression. Biomaterials 2009; 30: 5392-5402.

Das M, et al. Temporal neurotransmitter conditioning restores the functional activity of adult spinal cord neurons in long-term culture. Experimental Neurology 2008; 209: 171-180

Das M, et al. A defined long-term in vitro tissue engineered model of neuromuscular junctions. Biomaterials 31, 4880-4888 (2010).

Das, M. et al. A defined system to allow skeletal muscle differentiation and subsequent integration with silicon microstructures. Biomaterials 27, 4374-4380 (2006).

Das M, et al. Electrophysiological and morphological characterization of rat embryonic motoneurons in a defined system. Biotechnology progress 19, 1756-1761, (2003).

Davis, H. et al. Rat Cortical Oligodendrocyte-Embryonic Motoneuron Co-Culture: An Axon-Oligodendrocyte Interaction Model. Journal biomaterials tissue engin 2, 206-214 (2012).

Dhir V, et al. Patterning of diverse mammalian cell types in serum free medium with photoablation. Biotechnol Prog 2009; 25(2): 594-603.

Edwards D, et al. Addition of glutamate to serum-free culture promotes recovery of electrical activity in adult hippocampal neurons in vitro. J Neuroscience meth 190, 155-163 (2010).

Guo X F, et al. Characterization of a human fetal spinal cord stem cell line nsi-566rsc and its induction to functional motoneurons. Tissue Engineering and Regenerative Medicine 2010; 4: 181-193.

Guo X F, et al. Nmj formation between human stem cell derived motoneurons and rat skeletal muscle in a defined system. Tissue Engineering: Part C 2010; 16(6): 1347-1355.

Guo X, et al. Neuromuscular junction formation between human stem cell-derived motoneurons and human skeletal muscle in a defined system. Biomaterials 32, 9602-9611 (2011).

Guo X, et al. Characterization of a human fetal spinal cord stem cell line, NSI-566RSC, and its induction to functional motoneurons. Journal of Tissue Engineering and Regenerative Medicine 4, 181-193 (2010).

Guo X, et al. Derivation of sensory neurons and neural crest stem cells from human neural progenitor hNP1. Biomaterials 34, 4418-4427 (2013).

Hughes B. 2007 fda drug approvals: A year of flux specialty products dominate innovative drug approvals—a trend that looks set to continue. Nature Reviews Drug Discovery 2008; 7: 107-109.

Huh, D. et al. Reconstituting organ-level lung functions on a chip. Science 328, 1662-1668 (2010).

Jung D R, et al. Cell-based sensor microelectrode array characterized by imaging x-ray photoelectron spectroscopy, scanning electron microscopy, impedance measurements, and extracellular recordings. J VacSciTechnol A 1998; 16(3): 1183-1188.

Kang J H, et al. In vitro 3D model for human vascularized adipose tissue. Tissue Eng Part A 15, 2227-2236 (2009).

Kim C, et al. Non-cardiomyocytes influence the electrophysiological maturation of human embryonic stem cell-derived cardiomyocytes during differentiation. Stem cells and development 2010; 19(6): 783-795.

Kita-Matsuo H, et al. Lentiviral vectors and protocols for creation of stable hesc lines for fluorescent tracking and drug resistance selection of cardiomyocytes. PLoS ONE 2009; 4(4): e5046.

Lawrence C L, et al. Nonclinical proarrhythmia models: Predicting torsades de pointes. Journal of Pharmacological and Toxicological Methods 2005; 52(1): 46-59.

Lipsett M A, et al. Acinar plasticity: development of a novel in vitro model to study human acinar-to-duct-to-islet differentiation. Pancreas 34, 452-457 (2007).

Liu W P, et al. Enantioselectivity in environmental safety of current chiral insecticides. Proc Natl Acad Sci USA 2005; 102(3): 701-706.

Lund A E, et al. Dose-dependent interaction of the pyrethroid isomers with sodium-channels of squid axon-membranes. Neurotoxicology 1982; 3(1): 11-24.

Maduell F. Hemodiafiltration. Hemodial Int 2005; 9(1): 47-55.

Mahler G J, et al. Characterization of a gastrointestinal tract microscale cell culture analog used to predict drug toxicity. Biotechnol Bioeng 2009; 104(1): 193-205.

Mahler G J, et al. Characterization of caco-2 and ht29-mtx co-cultures in an in vitro digestion/cell culture model used to predict iron bioavailability. J Nutr Biochem 2009; 20(7): 494-502.

Marona H R N, et al. Determination of sparfloxcin and its degradation products by hplc-pda. J Antimicrob Chemother 1999; 44: 301-302.

McAleer C W, et al. Functional myotube formation from adult rat satellite cells in a defined serum-free system. Biotechnol Prog. 2015; 31(4):997-1003.

McAleer C W, et al. Mechanistic investigation of adult myotube response to exercise and drug treatment in vitro using a multiplexed functional assay system. J Appl Physiol (1985). 2014; 117(11):1398-405

McAuliffe G J, et al. Development of a gastrointestinal tract microscale cell culture analog to predict drug transport. Mol Cell Bioenrg 2008; 5(2): 119-132.

Meyer T, et al. Qt-screen: High-throughput cardiac safety pharmacology by extracellular electrophysiology on primary cardiac myocytes. Assay and Drug Development Technologies 2004; 2(5): 507-514.

Mohan D K, et al. Toxin detection based on action potential shape analysis using a realistic mathematical model of differentiated ng108-15 cells. Biosens Bioelectron 2006; 21: 1804-1811.

Molnar P, et al. Photolithographic patterning of c2c12 myotubes using vitronectin as growth substrate in serum-free medium. Biotechnol Prog 2007; 23(1): 265-268.

Molnar P, et al. Synaptic connectivity in engineered neuronal networks, in Patch-clamp methods and protocols, Molnar P and Hickman J J, Editors. 2007, Humana Press: New York.

Mufti N A, et al. Different in vitro systems affect cyp1a1 activity in response to 2,3,7,8-tetrachlorodibenzo-p-dioxin. Toxicol in vitro 1998; 12: 259-272.

Nakamura Y, et al. The in vitro metabolism of a pyrethroid insecticide, permethrin, and its hydrolysis products in rats. Toxicol Appl Pharmacol 2007; 235: 176-184.

Natarajan A, et al. Engineered In Vitro Feed-Forward Networks. J Biotechnol Biomater 3, 2 (2013).

Nataraj an A, et al. Multielectrode recordings of cardiac action potentials as a high throughput method to evaluate pesticide toxicity. Toxicol In Vitro 2006; 20(3): 375-381.

Natarajan A, et al. Patterned cardiomyocytes on microelectrode arrays as a functional, high information content drug screening platform. Biomaterials 2011; in press.

Natarajan, A. et al. Patterned cardiomyocytes on microelectrode arrays as a functional, high information content drug screening platform. Biomaterials 32, 4267-4274 (2011).

Oh T-i, et al. Real-time fluorescence detection of multiple microscale cell culture analog devices in situ. Cytometry Part A 2007; 71A: 857-865.

Oleaga C, et al. Multi-Organ toxicity demonstration in a functional human in vitro system composed of four organs. Sci Rep. 2016; 6:20030

Pirozzi K L, et al. Correlation of embryonic skeletal muscle myotube physical characteristics with contractile force generation on an atomic force microscope-based bio-microelectromechanical systems device. Appl Phys Lett. 2013; 103(8):83108

Pointer C, P et al. Ht29-mtx and caco-21tc7 monolayers as predictive models for human intestinal absorption: Role of mucus layer. J Pharm Sci 2001; 90: 1608-1619.

Rumsey J W, et al. Node of ranvier formation on motoneurons in vitro. Biomaterials 2009; 30: 3567-3572.

Rumsey J W, et al. Tissue engineering the mechanosensory circuit of the stretch reflex arc: Sensory neuron innervation of intrafusal muscle fibers. Biomaterials 31, 8218-8227 (2010).

Schaffner A E, et al. Investigation of the factors necessary for growth of hippocampal neurons in a defined system. J Neurosci Methods 1995; 62(1-2): 111-9.

Schaffner A E, et al. Investigation of the factors necessary for growth of hippocampal neurons in a defined system. Journal of neuroscience methods 62, 111-119 (1995).

Scollon E J, et al. In vitro metabolism of pyrethroid pesticides by rat and human hepatic microsomes and cytochrome p450 isoforms. Drug Metabolism and Disposition 2009; 37(1): 221-228.

Selivanova O M, et al. Compact globular structure of thermos *Thermophilus* ribosomal protein s1 in solution. J Biol Chem 2003; 278(38): 36311-36314.

Sin A, et al. The design and fabrication of three-chamber microscale cell culture analog devices with integrated dissolved oxygen sensors. Biotechnol Prog 2004; 20: 338-345.

Smith A S, et al. A multiplexed chip-based assay system for investigating the functional development of human skeletal myotubes in vitro. J Biotechnol. 2014; 185:15-8.

Smith A S, et al. Utilization of microscale silicon cantilevers to assess cellular contractile function in vitro. J Vis Exp. 2014; (92):e51866

Stancescu M, et al. A phenotypic in vitro model for the main determinants of human whole heart function. Biomaterials. 2015; 60:20-30

Subramanian, B. et al. Tissue-engineered three-dimensional in vitro models for normal and diseased kidney. Tissue Eng Part A 16, 2821-2831 (2010).

Sung J H, et al. A micro cell culture analog with 3-d hydrogel culture of multiple cell lines to assess metabolism-dependent cytotoxicity of anti-cancer drugs. Lab Chip 2009; 9(10): 1385-1394.

Sung J H, et al. A microfluidic device for a pharmacokinetic-pharmacodynamic (pk-pd) model on a chip. Lab Chip 2010; 10: 446-455.

Sung J H, et al. Fluorescence optical detection in situ for real time monitoring of enzymatic activity of liver cells in multiple microfludic devices. Biotechnol Bioeng 2009; 104: 516-525.

Sung J H, et al. Prevention of air bubble formation in a microfluidic perfusion cell culture system using a microscale bubble trap. Biomed Microdevices 2009; 11: 731-738.

Sung J H, et al. Microfabricated mammalian organ systems and their integration into models of whole animals and humans. Lab on a chip 13, 1201-1212 (2013).

Suter W. Predictive value of in vitro safety studies. Current Opinion in Chemical Biology 2006; 10(4): 362-366.

Sutton N M, et al Clinical effects and outcome of feline permethrin spot-on poisonings reported to the veterinary poisons information service (vpis), london. J Feline Med & Surgery 2007; 9: 335-339.

Swynghedauw B. Molecular mechanisms of myocardial remodeling. Physiol Rev 1999; 79(1): 215-262.

Takagishi Y, et al. Species-specific difference in distribution of voltage-gated 1-type ca2+ channels of cardiac myocytes. Am J Physiol Cell Physiol 2000; 279(6): C1963-1969.

Tatosian D A, et al. A novel system for evaluation of drug mixtures for potential efficacy in treating multidrug resistant cancers. Biotechnol Bioeng 2009; 103(1): 187-198.

van der Valk J, et al. Optimization of chemically defined cell culture media—replacing fetal bovine serum in mammalian in vitro methods. Toxicology in vitro: an international journal published in association with BIBRA 24, 1053-1063 (2010).

Varghese K, et al. A new target for amyloid beta toxicity validated by standard and high-throughput electrophysiology. PLoS One 2010; 5(1): e8643.

Varghese K, et al. Regeneration and characterization of adult mouse hippocampal neurons in a defined in vitro system. J Neurosci Methods 2009; 177: 51-59.

Viravaidya K, et al. Incorporation of 3t3-I1 cells to mimic bioaccumulation in a microscale cell culture analog device for toxicity studies. Biotechnol Prog 2004; 20: 590-597.

Wagner I, et al. A dynamic multi-organ-chip for long-term cultivation and substance testing proven by 3D human liver and skin tissue co-culture. Lab on a chip (2013).

Wilson K, et al. Direct patterning of coplanar polyethylene glycol alkylsilane monolayers by deep-ultraviolet photolithography as a general method for high fidelity, long-term cell patterning and culture. JUST B 2011; in press.

Wilson K, et al. Integration of functional myotubes with a bio-mems device for non-invasive interrogation. Lab Chip 2007; 7: 920-922.

Wilson K, et al. Measurement of contractile stress generated by cultured muscle on silicon cantilevers. PLoS One 2010; 5(6): e11042.

Wilson K, et al. Measurement of contractile stress generated by cultured rat muscle on silicon cantilevers for toxin detection and muscle performance enhancement. PLoS One. 2010; 5(6):e11042

Xu H, et al. Development of a stable dual cell-line gfp expression system to study estrogenic endocrine disruptors. Biotechnol Bioeng 2008; 101(6): 1276-1287.

Zimmermann W H, et al. Tissue engineering of a differentiated cardiac muscle construct. Circulation Research 2002; 90(2): 223-230.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A gravity driven pumpless microfluidic system, comprising:
 a first chamber containing a first plurality of organ cells attached to at least a portion of a cell attachment surface of the first chamber, wherein the first plurality of organ cells mimics a function of a first organ;
 a microcantilever sensor to non-invasively measure a function of the first plurality of organ cells; and
 at least one population of living immune cells, including at least one population of leukocytes, recirculating through the first chamber in a serum free culture medium for at least two days without activation,
 wherein the serum free medium comprises GDNF, BDNF, CNTF, NT3, NT4, vitronectin, agrin, sonic hedgehog, laminin, cAMP, retinoic acid, IGF-1, and NaCl.

2. The pumpless microfluidic system of claim 1, further comprising a second chamber in fluid connection with the first chamber containing a second plurality of organ cells attached to at least a portion of a cell attachment surface of the second chamber, wherein the second plurality of organ cells mimic a function of a second organ.

3. The pumpless microfluidic system of claim 2, further comprising a third chamber in fluid connection with the first and second chambers containing a third plurality of organ cells attached to at least a portion of a cell attachment surface of the third chamber, wherein the third plurality of organ cells mimic a function of a third organ.

4. The pumpless microfluidic system of claim 1, wherein the organ cells are selected from the group consisting of: cardiomyocytes, skeletal muscle myotubes, hepatocytes, kidney cells, neurons, epithelial cells, astrocytes, Schwann cells, bone marrow cells, cancer cells lines (drug-resistant and non-drug resistant), blood vessel endothelial cells, pancreatic islet cells, oligodendrocytes, synoviocytes, and fibroblasts.

5. The pumpless microfluidic system of claim 1, wherein first chamber and the microcantilever sensor are arranged on a chip.

6. The pumpless microfluidic system of claim 1, further comprising a recording device operably connected to the microcantilever sensor, wherein the recording device is configured to record data from the microcantilever sensor.

7. The pumpless microfluidic system of claim 6, wherein the first chamber is one of a plurality of chambers, and the system further comprises one or more microfluidic channels interconnecting the plurality of chambers.

8. The pumpless microfluidic system of claim 1, wherein the at least one population of immune cells comprise at least one of: peripheral blood mononuclear cells (PBMCs); granulocytes selected from the group consisting of neutrophils, eosinophils, basophils, and mast cells; or agranulocytes selected from the group consisting of monocytes, macrophages, lymphocytes, and natural killer (NK) cells.

9. The pumpless microfluidic system of claim 1, further comprising at least one agonist or antagonist of an innate immune response.

10. The pumpless microfluidic system of claim 9, wherein agonist or antagonist of the innate immune response comprises a complement protein or an interferon and/or activates a complement cascade.

11. The pumpless microfluidic system of claim 1, further comprising at least one agonist or antagonist of an adaptive immune response.

12. The pumpless microfluidic system of claim 11, wherein agonist or antagonist of the adaptive immune response comprises an antibody or a cytokine.

13. A method for mimicking an immune system, the method comprising;
    attaching a first plurality of organ cells to at least a portion of a cell attachment surface in a first chamber of a gravity driven pumpless microfluidic system;
    measuring a function of the first plurality of organ cells with a microcantilever sensor;
    recirculating at least one population of immune cells, including at least one population of leukocytes, through the first chamber in a serum free culture medium comprising GDNF, BDNF, CNTF, NT3, NT4, vitronectin, agrin, sonic hedgehog, laminin, cAMP, retinoic acid, IGF-1, and NaCl; and
    maintaining viability of the at least one population of leukocytes for at least two days without activation.

14. The method of claim 13, further comprising evaluating the system for an immune response.

15. The method of claim 14, wherein the immune response is evaluated by monitoring the first plurality of organ cells for immune cell infiltration.

16. The method of claim 14, further comprising activating an immune reaction in the pumpless microfluidic system and continuing the culture for a defined period prior to evaluating the system for an immune response.

17. The method of claim 16, wherein the immune reaction is activated by a physical insult to the first plurality of organ cells or by adding one or more chemical or biological agents to the culture medium.

18. The method of claim 13, further comprising measuring a functional readout of tissue damage.

* * * * *